United States Patent
Chaki et al.

[11] Patent Number: 5,783,564
[45] Date of Patent: Jul. 21, 1998

[54] SIALIC ACID DERIVATIVES

[75] Inventors: Haruyuki Chaki; Naoko Ando; Yasuhiro Morinaka; Ken-ichi Saito; Tomoko Yugami; Rie Yoshida, all of Yokohama, Japan

[73] Assignee: Mitsubishi Chemical Corporation, Tokyo, Japan

[21] Appl. No.: 669,219

[22] Filed: Jun. 24, 1996

Related U.S. Application Data

[63] Continuation-in-part of Ser. No. 362,947, Dec. 23, 1994.

[30] Foreign Application Priority Data

Dec. 24, 1993 [JP] Japan ................... 5-328454

[51] Int. Cl.⁶ .................. A61K 31/70; A61K 31/58
[52] U.S. Cl. ........................... 514/42; 514/172
[58] Field of Search ............. 514/42, 172; 536/29.1; 549/417

[56] References Cited

U.S. PATENT DOCUMENTS

| | | | |
|---|---|---|---|
| Re. 34,091 | 10/1992 | Yoshimura et al. | 514/42 |
| 4,663,443 | 5/1987 | Shibayama et al. | 536/4.1 |
| 4,730,058 | 3/1988 | Ogawa et al. | 549/214 |
| 5,023,239 | 6/1991 | Ogura et al. | 514/26 |
| 5,104,856 | 4/1992 | Esko et al. | 514/26 |
| 5,177,062 | 1/1993 | Miyata et al. | 514/23 |
| 5,438,125 | 8/1995 | Okamoto et al. | 536/4.1 |
| 5,506,221 | 4/1996 | Andersen et al. | 514/172 |

FOREIGN PATENT DOCUMENTS

| | | |
|---|---|---|
| 0 502 827 | 9/1992 | European Pat. Off. |
| WO94/03469 | 2/1994 | WIPO |

OTHER PUBLICATIONS

Chaki et al., Chemical Abstracts, vol. 119, No. 15, 11 Oct., 1993, Columbus, Ohio Abstract No. 160725.
Mitsubishi Kasei Corp., Database WPI, Section CH, Week 9321, Derwent Publications Ltd., London GB AN 93-162 124 JP-A-05 092 991, 26 Mar. 1992.
Ito et al., Chemical Abstracts, vol. 115, No. 19, 11 Nov., 1991, Columbus, Ohio U.S. Abstract No. 198537 JP-A-09 181 287.
Nippon Zoki, Patent Abstracts of Japan, vol. 017, No. 4523 (C-1099) 19 Aug. 1993 JP-A-05 105694.

*Primary Examiner*—José G. Dees
*Assistant Examiner*—Barbara Badio
*Attorney, Agent, or Firm*—Wenderoth, Lind & Ponack

[57] ABSTRACT

Sialic acid derivatives represented by the general formula (I):

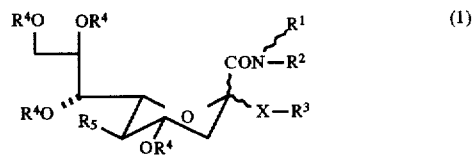

wherein $R^1$ is a steroidal compound residue;
$R^2$ is H or alkyl;
$R^3$ is alkyl;

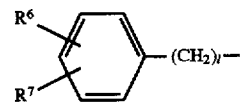

wherein each of $R^6$ and $R^7$ is H, alkyl or the like and I is an integer of 0 to 6; or the like;

X is O or S;
$R^4$ is H or acyl; and $R^5$ is $R^{14}O$—($R^{14}$ is H or acyl) or $R^{15}NH$—($R^{15}$ is acyl or the like);
their salts, hydrates or solvates are provided.

Sialic acid derivatives of the present invention are expected to be effective medicines for the prevention and therapy of senile dementia including Alzheimer's disease and the like, because they increase ChAT activity in cholinergic neurons.

5 Claims, 2 Drawing Sheets

SIALIC ACID DERIVATIVES

This application is a Continuation-In-Part of application Ser. No. 08/362,947 filed Dec. 23, 1994.

BACKGROUND OF THE INVENTION

1. Field of the Invention

The present invention relates to novel sialic acid derivatives having a amido bond, or salts thereof, which are useful for treating various diseases such as caused by disorder of cholinergic neurons.

2. Description of the Prior Art

Glutamic acid is one of the main excitatory neurotransmitters in the central nervous system of vertebrata. However, it has been reported that this amino acid plays an important role in the neuronal death caused by various degenerative diseases in the central nervous system [Trends Neurosci., 11, 465–469 (1988); Trends Pharmacol. Sci. 11, 379–387 (1990), etc.]. Namely, its association with neuronal death in ischemic dysfunction such as cerebrovascular disorder and others, amyotrophic lateral sclerosis, Huntington's disease, Parkinson's disease, Alzheimer's disease, cerebellar ataxia, trauma, and AIDS encephalopathy have been reported [Taisha 26(6), 55–63 (1989); The New England J. Medicine. 330 (9), 613–622 (1994), etc.]. In addition, the relation of inflammatory encephalopathy with glutamic acid induced neuronal dysfunction has been reported [Exp. Neurol., 125 (1), 119–124 (1994); Ann. Neurol., 35, 17–21 (1994); Pediatr. Res., 33 (5), 510–513 (1993), etc.]. Therefore, prevention of neuronal death due to glutamic acid is believed to provide a means for developing effective prophylactic and therapeutic drugs for these diseases. However, drugs exhibiting sufficient efficacy have not been discovered yet.

In the treatment of neuronal dysfunction, that is, diseases of the central and the peripheral nervous systems, studies on drugs for diseases in the central nervous system and their clinical application have been carried out extensively, whereas studies on drugs for diseases in the peripheral nervous system, particularly for peripheral neuropathy, have been modestly conducted. Lowered velocity of the nerve conduction in peripheral neuropathy has been reported [Disorders of Voluntary Muscle, Churchil/Livingstone, 973–1002 (1974); J Neurol, Neurosur. Psych., 58, 274–283 (1995), etc.], and protection of this lowering of the nerve conduction velocity appears to be an effective treatment of peripheral neuropathy. To date, natural glycolipids, ganglioside (Trade name: Cronassiai, Japanese Patent Publication (kokai) No. 52-34912), vitamins, mecobalamin (general name of a medicine) and inhibitors of aldose reductase (Japanese Patent Publication (kokai) No. 60-156387) have been used clinically, but their efficacy appears insufficient and further development of better drugs are expected.

Senile dementia including Alzheimer's disease is a disease which shows progressive amnesia and agnosia. In these diseases the salient disorder is found in cholinergic nervous system which projects from basal forebrain to cerebral cortex and hippocampus. Because these neurons show remarkable reduction of acetylcholine-synthesizing enzyme, choline acetyltransferase (referred to as "ChAT" hereinafter), drugs which activate ChAT activity are considered to be useful as therapeutic drugs for senile dementia including Alzheimer's disease. Further, it is expected that drugs having such activity are also useful as therapeutic drugs for peripheral neuropathy.

On the other hand, gangliosides i.e. glycosphingolipids including sialic acid are a component of biomembranes and contained in brains of higher animals in quantity. Because gangliosides, which have been recently reported on their various functions, are found preferentially in membranes of neurons, their role in neurons has been studied extensively. Sialic acid is an important component of gangliosides, and various sialic acid derivatives have been synthesized for the purpose of investigating the correlation between the sialic acid and ganglioside's function and its applications in medical field (Japanese patent publication (Kokai) Nos. 89298/1980, 243096/1986, 282390/1986, 41492/1988, 41494/1988, 63697/1988, 68526/1988, 52794/1989, 190693/1989 and 151398/1991; and PCT patent publication Nos. WO93/10134 and WO94/03469, etc.). Some reports have been made on the activity of the sialic acid derivatives (Japanese patent publication (Kokai) Nos. 265229/1987, 93529/1989, 77898/1991 and 81287/1991; and Brain Research, 438, 277–285 (1988)). However, derivatives which sufficiently increase ChAT activity have not been developed yet.

SUMMARY OF THE INVENTION

The inventors of the present invention have made extensive studies in order to provide a therapeutic drug for diseases of central nervous system such as senile dementia including Alzheimer's disease, and ischemic disorder, and peripheral nervous system. Consequently, they have discovered and found that sialic acid derivatives with a specific amido bond are useful as therapeutic drugs which alleviate diseases of central nervous system such as senile dementia including Alzheimer's disease and diseases of peripheral nervous system such as diabetic neuropathy, etc. The present invention is based on such findings.

Thus, the gist of the present invention exists in a sialic acid derivative represented by the general formula (1)

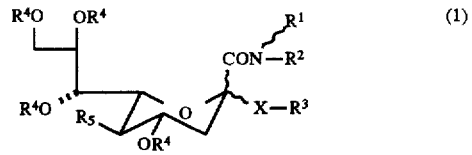 (1)

Wherein $R^1$ represents a steroidal compound residue:
$R^2$ represents hydrogen or $C_1$–$C_4$ alkyl:
$R^3$ represents $C_1$–$C_{15}$ alkyl;

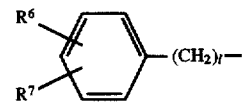

wherein each of $R^6$ and $R^7$ independently represents hydrogen, halogen, $C_1$–$C_4$ alkyl, hydroxyl, $R^8O$— wherein $R^8$ represents $C_1$–$C_4$ alkyl, phenyl or phenyl-($C_1$–$C_3$) alkyl, nitro, amino, $C_1$–$C_4$ alkylamino, $C_2$–$C_8$ dialkylamino, or

wherein $R^9$ represents hydrogen, $C_1$–$C_4$ alkyl, phenyl or phenyl-($C_1$–$C_3$) alkyl, and I represents an integer of 0 to 6; $R^{10}O$ $(CH_2)_m$— wherein $R^{10}$ represents hydrogen, $C_1$–$C_4$ alkyl, phenyl which may have one or more substitutents selected from a group consisting of $C_1$–$C_4$ alkyl, halogen, hydroxyl, nitro, amino and carboxyl, or phenyl-($C_1$–$C_3$) alkyl which may have one or more substitutents selected from a group consisting of $C_1$-$C_4$ alkyl, halogen, hydroxyl, nitro, amino and carboxyl, and m represents an integer of 2 to 6; or

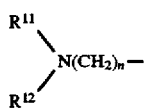

wherein $R^{11}$ represents hydrogen or $C_1$-$C_4$ alkyl, $R^{12}$ represents hydrogen, $C_1$-$C_4$ alkyl, $C_2$-$C_7$ acyl, $C_1$-$C_4$ alkylsulfonyl, phenylsulfonyl which may have one or more substituents selected from a group consisting of $C_1$-$C_4$ alkyl, halogen, hydroxyl, nitro, amino and carboxyl, or

wherein $R^{13}$ represents $C_1$-$C_4$ alkyl, phenyl or phenyl-$(C_1$-$C_3)$ alkyl, and n is an integer of 2 to 6:

$R^4$ represents hydrogen or $C_2$-$C_7$ acyl:

$R^5$ represents $R^{14}O$— wherein $R^{14}$ represents hydrogen or $C_2$-$C_7$ acyl; or $R^{15}NH$— wherein $R^{15}$ represents $C_2$-$C_7$ acyl.

wherein $R^{16}$ represents hydrogen, $C_1$-$C_6$ alkyl, phenyl or phenyl-$(C_1$-$C_3)$ alkyl and p is an integer of 0 to 4, $C_7$-$C_{11}$ aroyl which may have one or more substituents selected from a group consisting of $C_1$-$C_4$ alkyl, halogen, hydroxyl, nitro, amino and carboxyl, phenyl-$(C_1$-$C_3)$ alkylcarbonyl which may have one or more substituents selected from a group consisting of $C_1$-$C_4$ alkyl, halogen, hydroxyl, nitro, amino and carboxyl, $C_1$-$C_4$ alkylsulfonyl, or phenylsulfonyl which may have one or more substituents selected from a group consisting of $C_1$-$C_4$ alkyl, halogen, hydroxyl, nitro, amino and carboxyl: and X represents O or S:
salts, hydrates or solvates thereof.

DETAILED DESCRIPTION OF THE INVENTION

The present invention is explained in detail hereinafter. The sialic acid derivatives of the present invention are represented by the general formula (I).

The $C_1$-$C_4$ alkyl defined in said general formula (I) includes methyl, ethyl, n-propyl, i-propyl, n-butyl, t-butyl and the like, and the $C_1$-$C_{15}$ alkyl includes methyl, ethyl, n-propyl, i-propyl, n-butyl, t-butyl, n-pentyl, n-hexyl, n-heptyl, n-octyl, n-decyl, n-pentadecyl and the like. The $C_1$-$C_6$ alkyl includes the $C_1$-$C_6$ groups defined in said $C_1$-$C_{15}$ alkyl. The halogen includes fluorine, chlorine, bromine and the like, and the phenyl $(C_1$-$C_3)$ alkyl includes benzyl, phenethyl and the like. The $C_2$-$C_7$ acyl includes acetyl, propionyl, butyryl, valeryl, benzoyl and the like, and the $C_1$-$C_4$ alkylsulfonyl includes methylsulfonyl, ethylsulfonyl, n-propylsulfonyl, n-butylsulfonyl and the like. Further, $C_1$-$C_4$ alkylamino includes methylamino, ethylamino, butylamino and the like, and $C_2$-$C_8$ dialkylamino includes dimethylamino, diethylamino, dibutylamino and the like. The $C_7$-$C_{11}$ aroyl includes benzoyl, toluoyl, naphthoyl and the like, and the phenyl $(C_1$-$C_3)$ alkylcarbonyl includes benzylcarbonyl, phenylethylcarbonyl, phenylpropylcarbonyl and the like.

Other groups not specifically mentioned in the above definitions may be employed in the present invention, which can be derived from the combination of two or more of the above listed groups.

The steroid compound residues defined by $R^1$ specifically include groups represented by the following formula.

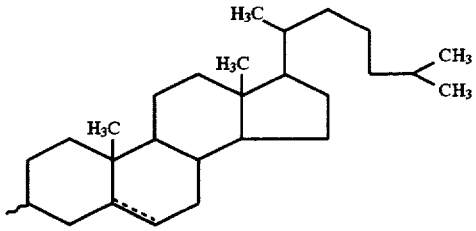

In the above formula, the dotted line represents a single bond or no bond, and the configuration at 3-position of the steroid skeleton may be α-type or β-type.

Preferred $R^1$ includes the group represented by the following formula.

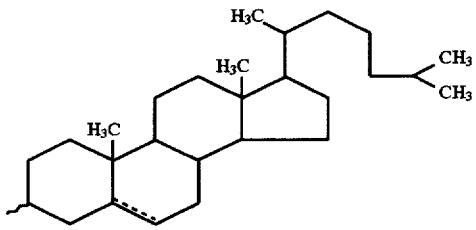

$R^2$ is preferably hydrogen or methyl, and most preferably hydrogen.

$R^3$ is preferably $C_1$-$C_8$ alkyl;

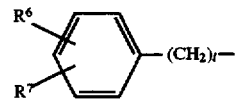

wherein each of $R^6$ and $R^7$ independently represents hydrogen, halogen or

wherein $R^9$ represents hydrogen or $C_1$-$C_4$ alkyl and l is an integer of 0 to 3; $R^{10}O(CH_2)_m$— wherein $R^{10}$ represents hydrogen, $C_1$-$C_4$ alkyl, phenyl or phenyl-$(C_1$-$C_3)$ alkyl, and m is an integer of 2 to 4; or

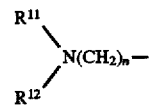

wherein $R^{11}$ represents hydrogen, $R^{12}$ represents hydrogen, $C_2$-$C_7$ acyl, $C_1$-$C_4$ alkylsulfonyl or

wherein $R^{13}$ represents phenyl-$(C_1$-$C_3)$ alkyl, and n is an integer of 2 to 4; and $R^3$ is more preferably $C_1$–$C_8$ alkyl or

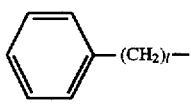

wherein I is an integer of 0 to 3, and most preferably $C_1$–$C_3$ alkyl.

$R^4$ is preferably hydrogen or acetyl, and most preferably hydrogen.

$R^5$ is preferably $C^{14}O$— wherein $R^{14}$ represents hydrogen or acetyl; or $R^{15}NH$— wherein $R^{15}$ represents $C_2$–$C_7$ acyl,

wherein $R^{16}$ represents hydrogen, $C_1$–$C_4$ alkyl or phenyl-($C_1$–$C_3$) alkyl and p is an integer of 0 to 4, $C_7$–$C_{11}$ aloyl, $C_1$–$C_3$ alkylsulfonyl or phenylsulfonyl; and $R^5$ is more preferably $R^{14}O$— wherein $R^{14}$ represents hydrogen, or $R^{15}NH$— wherein $R^{15}$ represents $C_2$–$C_5$ acyl or

wherein $R^{16}$ represents hydrogen and p is an integer of 1, and most preferably $R^{15}NH$— wherein $R^{15}$ represents acetyl.

X is most preferably oxygen.

Further, most preferable compounds include 3α-[N-(3-deoxy-2-O-methyl-α-D-glycero-D-galacto-2-nonulopyranosonyl) amino] cholestene (the α-isomer of compound No. 367 in Table 5);

3α-[N-(3-deoxy-2-O-methyl-α-D-glycero-D-galacto-2-nonulopyranosonyl) amino]-5-cholestane (the α-isomer of compound No. 507 in Table 7);

3α-[N-(5-acetamido-3,5-dideoxy-2-O-methyl-α-D-glycero-D-galacto-2-nonulopyranosonyl) amino] cholestane (the α-isomer of compound No. 4 in Table 1);

3α-[N-{5-acetamido-3,5-dideoxy-2-O-phenyl-α-D-glycero-D-galacto-2-nonulopyranosonyl} amino] cholestane (the α-isomer of compound No. 19 in Table 1);

3α-[N-(5-acetamido-3,5-dideoxy-2-O-benzyl-α-D-glycero-D-galacto-2-nonulopyranosonyl) amino] cholestane (the α-isomer of compound No. 21 in Table 1)

3α-[N-(5-acetamido-3,5-dideoxy-2-O-methyl-α-D-glycero-D-galacto-2-nonulopyranosonyl) amino]-5-cholestene (the α-isomer of compound No. 234 in Table 1);

3α-[N-(5-acetamido-3,5-dideoxy-2-S-phenyl-2-thio-α-glycero-D-galacto-2-nonulopyranosonyl) amino] cholestane (the α-isomer of compound No. 260 in Table 2);

3α-[N-(5-acetamido-3,5-dideoxy-2-O-methyl-β-D-glycero-D-galacto-2-nonulopyranosonyl) amino] cholestane (the α-isomer of compound No. 268 in Table 3); and 3α-[N-(5-acetamido-3,5-dideoxy-2-O-benzyl-β-D-glycero-D-galacto-2-nonulopyranosonyl) amino] cholestane (the α-isomer of compound No. 281 in Table 3).

Specific examples of preferable compounds represented by the general formula (I) mentioned above are shown in the following Tables 1, 2, 3, 4, 5, 6, 7 and 8.

TABLE 1

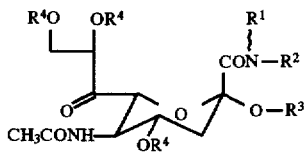

| Compound No. | $R^1$ | $R^2$ | $R^3$ | $R^4$ |
|---|---|---|---|---|
| 1 | (cholestane group) | H | —CH$_3$ | —COCH$_3$ |
| 2 | " | H | —CH$_3$ | —COCH$_2$CH$_3$ |
| 3 | " | H | —CH$_3$ | —CO—phenyl |
| 4 | " | H | —CH$_3$ | H |
| 5 | " | —CH$_3$ | —CH$_3$ | —COCH$_3$ |

TABLE 1-continued
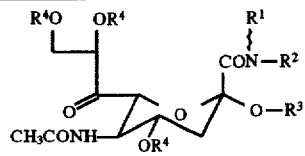
| Compound No. | R¹ | R² | R³ | R⁴ |
|---|---|---|---|---|
| 6 | " | —CH₃ | —CH₃ | H |
| 7 | " | —CH₂CH₃ | —CH₃ | H |
| 8 | " | ―(CH₂)₂CH₃ | —CH₃ | H |
| 9 | " | ―(CH₂)₃CH₃ | —CH₃ | H |
| 10 | " | H | —CH₂CH₃ | —COCH₃ |
| 11 | " | H | —CH₂CH₃ | H |
| 12 | " | 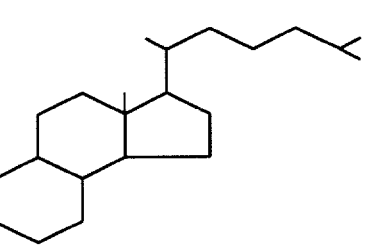 | ―(CH₂)₂CH₃ | H |
| 13 | " | H | ―(CH₂)₃CH₃ | H |
| 14 | " | H | ―(CH₂)₅CH₃ | —COCH₃ |
| 15 | " | H | ―(CH₂)₅CH₃ | H |
| 16 | " | H | ―(CH₂)₉CH₃ | H |
| 17 | " | H | ―(CH₂)₁₄CH₃ | H |
| 18 | " | H | 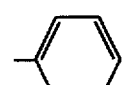 | —COCH₃ |
| 19 | " | H | 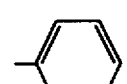 | H |
| 20 | " | H | 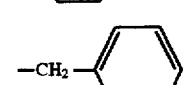 | —COCH₃ |
| 21 | " | H | 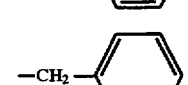 | H |
| 22 | " | H | 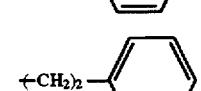 | H |
| 23 | " | H | 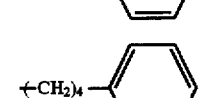 | H |
| 24 | " | H | 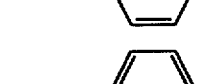 | H |

TABLE 1-continued
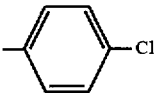
| Compound No. | R¹ | R² | R³ | R⁴ |
|---|---|---|---|---|
| 25 | " | H | 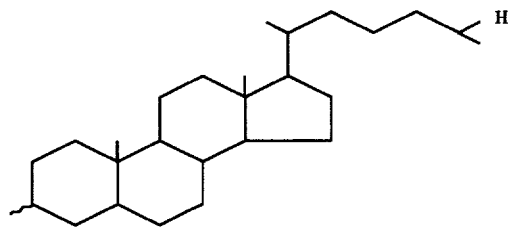 | —COCH₃ |
| 26 | 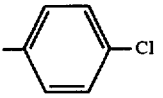 | H | 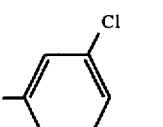 | H |
| 27 | " | H | 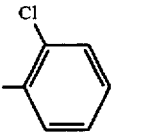 | H |
| 28 | " | H | 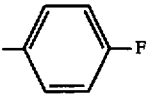 | H |
| 29 | " | H | 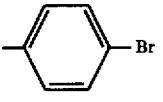 | H |
| 30 | " | H | 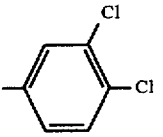 | H |
| 31 | " | H | 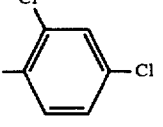 | H |
| 32 | " | H | 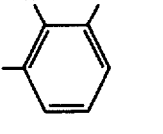 | H |
| 33 | " | H |  | H |

TABLE 1-continued
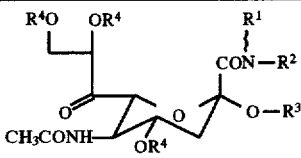
| Compound No. | R¹ | R² | R³ | R⁴ |
|---|---|---|---|---|
| 34 | " | H | 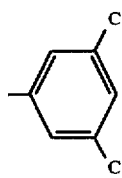 | H |
| 35 | " | H | 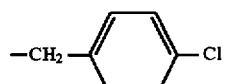 | H |
| 36 | " | H | 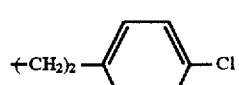 | H |
| 37 | " | H | 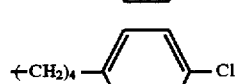 | H |
| 38 | 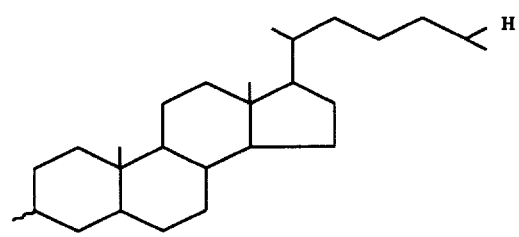 | H | 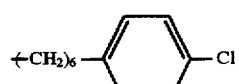 | H |
| 39 | " | H | 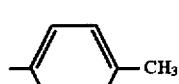 | H |
| 40 | " | H | 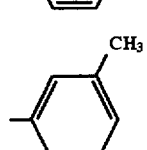 | H |
| 41 | " | H | 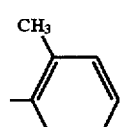 | H |
| 42 | " | H | 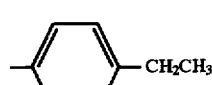 | H |
| 43 | " | H | 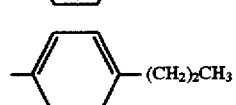 | H |

TABLE 1-continued
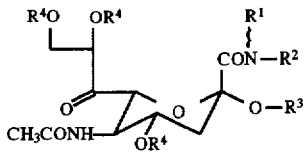
| Compound No. | R¹ | R² | R³ | R⁴ |
|---|---|---|---|---|
| 44 | " | H | 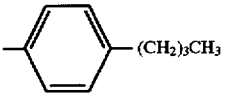 | H |
| 45 | " | H | 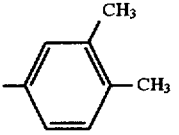 | H |
| 46 | " | H | 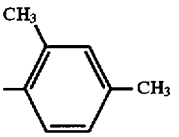 | H |
| 47 | " | H | 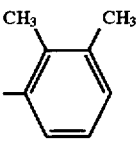 | H |
| 48 | " | H | 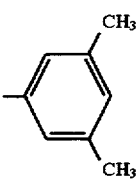 | H |
| 49 | 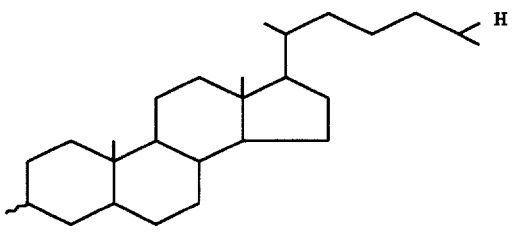 | H | 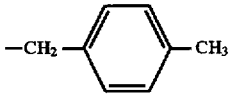 | H |
| 50 | " | H | 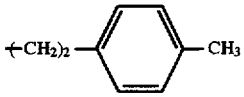 | H |
| 51 | " | H | 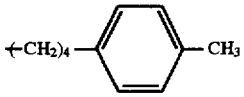 | H |
| 52 | " | H | 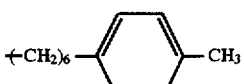 | H |
| 53 | " | H | 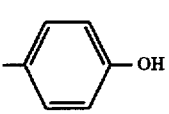 | H |

TABLE 1-continued

[Structure: R⁴O, OR⁴ on left sugar with CH₃CONH and OR⁴; linked via O to right portion with CON(R¹)—R², O—R³]

| Compound No. | R¹ | R² | R³ | R⁴ |
|---|---|---|---|---|
| 54 | " | H | 3-hydroxyphenyl | H |
| 55 | " | H | 2-hydroxyphenyl | H |
| 56 | " | H | 3,4-dihydroxyphenyl | H |
| 57 | " | H | 2,5-dihydroxyphenyl | H |
| 58 | " | H | 2,3-dihydroxyphenyl | H |
| 59 | " | H | 3,5-dihydroxyphenyl | H |
| 60 | cholestanyl group | H | —CH₂—(4-hydroxyphenyl) | H |
| 61 | " | H | —(CH₂)₂—(4-hydroxyphenyl) | H |
| 62 | " | H | —(CH₂)₄—(4-hydroxyphenyl) | H |

TABLE 1-continued
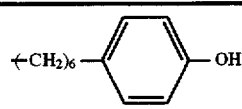
| Compound No. | R¹ | R² | R³ | R⁴ |
|---|---|---|---|---|
| 63 | " | H | -(CH₂)₆-C₆H₄-OH (para) | H |
| 64 | " | H | -C₆H₄-OCH₃ (para) | H |
| 65 | " | H | -C₆H₄-OCH₃ (meta) | H |
| 66 | " | H | -C₆H₄-OCH₃ (ortho) | H |
| 67 | " | H | -C₆H₄-OCH₂CH₃ (para) | H |
| 68 | " | H | -C₆H₄-O-C₆H₅ (para) | H |
| 69 | " | H | -C₆H₄-OCH₂-C₆H₅ (para) | H |
| 70 | cholestanyl | H | -C₆H₃(OCH₃)₂ (3,4-dimethoxy) | H |
| 71 | " | H | -C₆H₃(OCH₃)₂ (2,5-dimethoxy) | H |
| 72 | " | H | -C₆H₃(OCH₃)₂ (2,3-dimethoxy) | H |

TABLE 1-continued

Structure: core with R⁴O, OR⁴, CON-R¹R², O-R³, CH₃CONH, OR⁴ substituents

| Compound No. | R¹ | R² | R³ | R⁴ |
|---|---|---|---|---|
| 73 | " | H | 3,5-dimethoxyphenyl (OCH₃ at two positions) | H |
| 74 | " | H | -CH₂-C₆H₄-OCH₃ (para) | H |
| 75 | " | H | -(CH₂)₂-C₆H₄-OCH₃ (para) | H |
| 76 | " | H | -(CH₂)₄-C₆H₄-OCH₃ (para) | H |
| 77 | " | H | -(CH₂)₆-C₆H₄-OCH₃ (para) | H |
| 78 | " | H | 4-nitrophenyl | H |
| 79 | " | H | 3-nitrophenyl | H |
| 80 | " | H | 2-nitrophenyl | H |
| 81 | cholestanyl group | H | 3,4-dinitrophenyl | H |
| 82 | " | H | 2,4-dinitrophenyl | H |

TABLE 1-continued
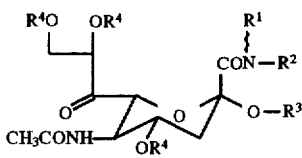
| Compound No. | R¹ | R² | R³ | R⁴ |
|---|---|---|---|---|
| 83 | " | H | 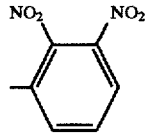 | H |
| 84 | " | H | 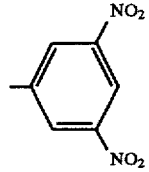 | H |
| 85 | " | H | 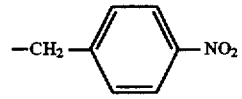 | H |
| 86 | " | H | 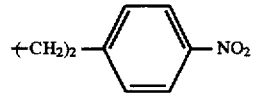 | H |
| 87 | " | H | 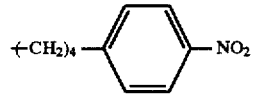 | H |
| 88 | " | H | 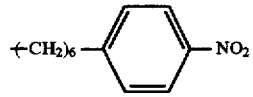 | H |
| 89 | " | H | 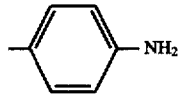 | H |
| 90 | " | H | 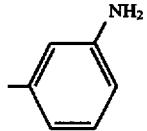 | H |
| 91 | " | H | 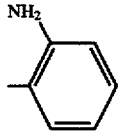 | H |

TABLE 1-continued

[Structure: R⁴O and OR⁴ on sugar with CH₃CONH group, O linkage, CON(R¹)R² and O-R³ substituents]

| Compound No. | R¹ | R² | R³ | R⁴ |
|---|---|---|---|---|
| 92 | cholestanyl group | H | 3,4-diaminophenyl | H |
| 93 | " | H | 2,4-diaminophenyl | H |
| 94 | " | H | 2,3-diaminophenyl | H |
| 95 | " | H | 3,5-diaminophenyl | H |
| 96 | " | H | $-CH_2-C_6H_4-NH_2$ (para) | H |
| 97 | " | H | $-(CH_2)_2-C_6H_4-NH_2$ (para) | H |
| 98 | " | H | $-(CH_2)_4-C_6H_4-NH_2$ (para) | H |
| 99 | " | H | $-(CH_2)_6-C_6H_4-NH_2$ (para) | H |
| 100 | " | H | 4-(NHCH₃)-phenyl | H |
| 101 | " | H | 3-(NHCH₃)-phenyl | H |

TABLE 1-continued

| Compound No. | R¹ | R² | R³ | R⁴ |
|---|---|---|---|---|
| 102 | " | H | (2-methylphenyl)-NHCH₃ | H |
| 103 | cholestanyl group | H | (4-substituted phenyl)-NHCH₂CH₃ | H |
| 104 | " | H | (4-substituted phenyl)-N(CH₃)₂ | H |
| 105 | " | H | (4-substituted phenyl)-N(CH₂CH₃)₂ | H |
| 106 | " | H | (phenyl with 1,2-di-NHCH₃) | H |
| 107 | " | H | (phenyl with 2,4-di-NHCH₃) | H |
| 108 | " | H | (phenyl with 2,3-di-NHCH₃) | H |
| 109 | " | H | (phenyl with 3,5-di-NHCH₃) | H |
| 110 | " | H | —CH₂—(4-substituted phenyl)-NHCH₃ | H |

TABLE 1-continued
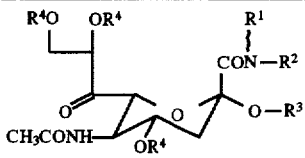
| Compound No. | R¹ | R² | R³ | R⁴ |
|---|---|---|---|---|
| 111 | " | H | $-(CH_2)_2-$C₆H₄$-NHCH_3$ | H |
| 112 | " | H | $-(CH_2)_4-$C₆H₄$-NHCH_3$ | H |
| 113 | " | " | $-(CH_2)_6-$C₆H₄$-NHCH_3$ | H |
| 114 | cholestanyl group | H | $-$C₆H₄$-COOH$ (para) | H |
| 115 | " | H | $-$C₆H₄$-COOH$ (meta) | H |
| 116 | " | H | $-$C₆H₄$-COOH$ (ortho) | H |
| 117 | " | H | $-$C₆H₄$-COOCH_3$ | $-COCH_3$ |
| 118 | " | H | $-$C₆H₄$-COOCH_3$ | H |
| 119 | " | H | $-$C₆H₄$-COOCH_2CH_3$ | H |
| 120 | " | H | $-$C₆H₄$-COO(CH_2)_2CH_3$ | H |
| 121 | " | H | $-$C₆H₄$-COO(CH_2)_3CH_3$ | H |

TABLE 1-continued

[Structure: sialic acid derivative with R⁴O, OR⁴, CH₃CONH, OR⁴ substituents on pyranose ring, and CON(R¹)R² and O-R³ groups]

| Compound No. | R¹ | R² | R³ | R⁴ |
|---|---|---|---|---|
| 122 | " | H | 4-(C₆H₅-OOC)-C₆H₄- | H |
| 123 | " | H | 4-(C₆H₅CH₂-OOC)-C₆H₄- | H |
| 124 | " | H | 4-(C₆H₅(CH₂)₂-OOC)-C₆H₄- | H |
| 125 | cholestanyl | H | 3,4-(HOOC)₂-C₆H₃- | H |
| 126 | " | H | 3,4-(HOOC)₂-C₆H₃- | H |
| 127 | " | H | 2,3-(HOOC)₂-C₆H₃- | H |
| 128 | " | H | 3,5-(HOOC)₂-C₆H₃- | H |
| 129 | " | H | -CH₂-C₆H₄-COOH | H |
| 130 | " | H | -CH₂-C₆H₄-COOCH₃ | -COCH₃ |
| 131 | " | H | -CH₂-C₆H₄-COOCH₃ | H |

TABLE 1-continued
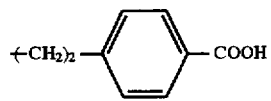
| Compound No. | R¹ | R² | R³ | R⁴ |
|---|---|---|---|---|
| 132 | " | H | $-(CH_2)_2-C_6H_4-COOH$ | H |
| 133 | " | H | $-(CH_2)_4-C_6H_4-COOH$ | H |
| 134 | " | H | $-(CH_2)_6-C_6H_4-COOH$ | H |
| 135 | " | H | $-(CH_2)_2-OH$ | $-COCH_3$ |
| 136 | cholestanyl | H | $-(CH_2)_2-OH$ | H |
| 137 | " | H | $-(CH_2)_4-OH$ | H |
| 138 | " | H | $-(CH_2)_6-OH$ | H |
| 139 | " | H | $-(CH_2)_2-OCH_3$ | $-COCH_3$ |
| 140 | " | H | $-(CH_2)_2-OCH_3$ | H |
| 141 | " | H | $-(CH_2)_2-OCH_2CH_3$ | H |
| 142 | " | H | $-(CH_2)_2-O(CH_2)_2CH_3$ | H |
| 143 | " | H | $-(CH_2)_2-O(CH_2)_3CH_3$ | H |
| 144 | " | H | $-(CH_2)_4-OCH_3$ | H |
| 145 | " | H | $-(CH_2)_6-OCH_3$ | H |
| 146 | " | H | $-(CH_2)_2-O-C_6H_5$ | H |
| 147 | cholestanyl | H | $-(CH_2)_4-O-C_6H_5$ | H |

TABLE 1-continued
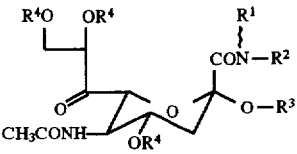
| Compound No. | R¹ | R² | R³ | R⁴ |
|---|---|---|---|---|
| 148 | " | H | -(CH₂)₆-O-C₆H₅ | H |
| 149 | " | H | -(CH₂)₂-O-C₆H₄-CH₃ (para) | H |
| 150 | " | H | -(CH₂)₂-O-C₆H₄-CH₃ (meta) | H |
| 151 | " | H | -(CH₂)₂-O-C₆H₄-CH₃ (ortho) | H |
| 152 | " | H | -(CH₂)₂-O-C₆H₄-CH₂CH₃ | H |
| 153 | " | H | -(CH₂)₂-O-C₆H₄-F | H |
| 154 | " | H | -(CH₂)₂-O-C₆H₄-Cl | H |
| 155 | " | H | -(CH₂)₂-O-C₆H₄-Br | H |
| 156 | " | H | -(CH₂)₂-O-C₆H₄-OH | H |
| 157 | " | H | -(CH₂)₂-O-C₆H₄-NO₂ | H |
| 158 | cholestanyl | H | -(CH₂)₂-O-C₆H₄-NH₂ | H |

TABLE 1-continued

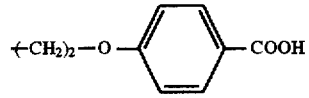

| Compound No. | R¹ | R² | R³ | R⁴ |
|---|---|---|---|---|
| 159 | " | H | $-(CH_2)_2-O-\text{C}_6\text{H}_4-COOH$ | H |
| 160 | " | H | $-(CH_2)_4-O-\text{C}_6\text{H}_4-CH_3$ | H |
| 161 | " | H | $-(CH_2)_6-O-\text{C}_6\text{H}_4-CH_3$ | H |
| 162 | " | H | $-(CH_2)_2-O-CH_2-\text{C}_6\text{H}_5$ | $-OCH_3$ |
| 163 | " | H | $-(CH_2)_2-O-CH_2-\text{C}_6\text{H}_5$ | H |
| 164 | " | H | $-(CH_2)_2-O-(CH_2)_2-\text{C}_6\text{H}_5$ | H |
| 165 | " | H | $-(CH_2)_4-O-CH_2-\text{C}_6\text{H}_5$ | H |
| 166 | " | H | $-(CH_2)_6-O-CH_2-\text{C}_6\text{H}_5$ | H |
| 167 | " | H | $-(CH_2)_2-O-CH_2-\text{C}_6\text{H}_4-CH_3$ (para) | H |
| 168 | " | H | $-(CH_2)_2-O-CH_2-\text{C}_6\text{H}_4-CH_3$ (meta) | H |
| 169 | cholestanyl | H | $-(CH_2)_2-O-CH_2-\text{C}_6\text{H}_4-CH_3$ (ortho) | H |

TABLE 1-continued
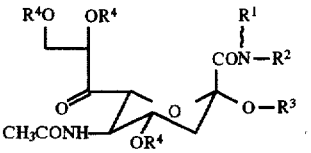
| Compound No. | R¹ | R² | R³ | R⁴ |
|---|---|---|---|---|
| 170 | " | H | -(CH₂)₂-O-(CH₂)₂-C₆H₄-CH₃ | H |
| 171 | " | H | -(CH₂)₂-O-CH₂-C₆H₄-Cl | H |
| 172 | " | H | -(CH₂)₂-O-(CH₂)₂-C₆H₄-Cl | H |
| 173 | " | H | -(CH₂)₂-O-CH₂-C₆H₄-OH | H |
| 174 | " | H | -(CH₂)₂-O-(CH₂)₂-C₆H₄-OH | H |
| 175 | " | H | -(CH₂)₂-O-CH₂-C₆H₄-NO₂ | H |
| 176 | " | H | -(CH₂)₂-O-(CH₂)₂-C₆H₄-NO₂ | H |
| 177 | " | H | -(CH₂)₂-O-CH₂-C₆H₄-NH₂ | H |
| 178 | " | H | -(CH₂)₂-O-(CH₂)₂-C₆H₄-NH₂ | H |
| 179 | " | H | -(CH₂)₄-O-CH₂-C₆H₄-CH₃ | H |
| 180 | cholestanyl | H | -(CH₂)₆-O-CH₂-C₆H₄-CH₃ | H |
| 181 | " | H | -(CH₂)₂NH₂ | -COCH₃ |

TABLE 1-continued

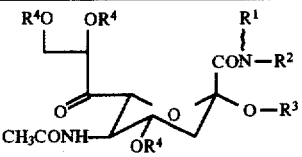

| Compound No. | R¹ | R² | R³ | R⁴ |
|---|---|---|---|---|
| 182 | " | H | $(CH_2)_2-NH_2$ | H |
| 183 | " | H | $(CH_2)_4-NH_2$ | H |
| 184 | " | H | $(CH_2)_6-NH_2$ | H |
| 185 | " | H | $(CH_2)_2-NHCH_3$ | H |
| 186 | " | H | $(CH_2)_2-NHCH_2CH_3$ | H |
| 187 | " | H | $(CH_2)_2-NH(CH_2)_2CH_3$ | H |
| 188 | " | H | $(CH_2)_2-NH(CH_2)_3CH_3$ | H |
| 189 | " | H | $(CH_2)_2-N(CH_3)_2$ | H |
| 190 | " | H | $(CH_2)_2-N(CH_2CH_3)_2$ | H |
| 191 | 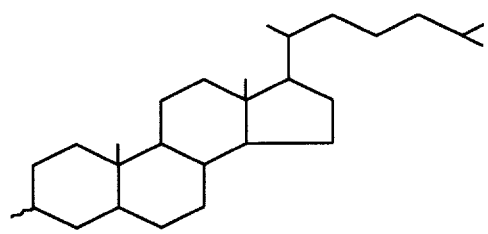 | H | $(CH_2)_2-N(CH_2CH_2CH_3)_2$ | H |
| 192 | " | H | $(CH_2)_2-N(CH_2CH_2CH_2CH_3)_2$ | H |
| 193 | " | H | $(CH_2)_4-NHCH_3$ | H |
| 194 | " | H | $(CH_2)_6-NHCH_3$ | H |
| 195 | " | H | $(CH_2)_2-NHCOCH_3$ | $-COCH_3$ |
| 196 | " | H | $(CH_2)_2-NHCOCH_3$ | H |
| 197 | " | H | $(CH_2)_2-NHCOCH_2CH_3$ | H |
| 198 | " | H | 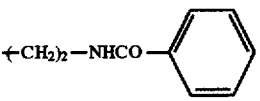 | H |
| 199 | " | H | $(CH_2)_4-NHCOCH_3$ | H |
| 200 | " | H | $(CH_2)_6-NHCOCH_3$ | H |
| 201 | " | H | $(CH_2)_2-NHSO_2CH_3$ | $-COCH_3$ |
| 202 | 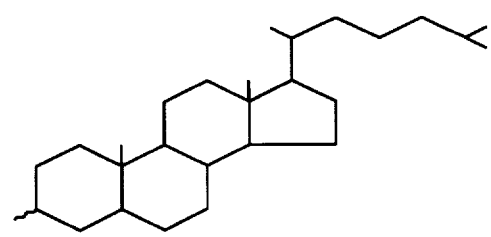 | H | $(CH_2)_2-NHSO_2CH_3$ | H |
| 203 | " | H | $(CH_2)_2-NHSO_2CH_2CH_3$ | H |
| 204 | " | H | $(CH_2)_2-NHSO_2(CH_2)_2CH_3$ | H |

TABLE 1-continued
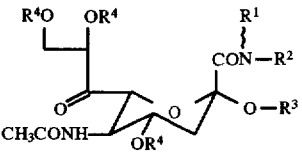
| Compound No. | R¹ | R² | R³ | R⁴ |
|---|---|---|---|---|
| 205 | " | H | $-(CH_2)_4-NHSO_2CH_3$ | H |
| 206 | " | H | $-(CH_2)_6-NHSO_2CH_3$ | H |
| 207 | " | H | $-(CH_2)_2-NHSO_2-C_6H_5$ | H |
| 208 | " | H | $-(CH_2)_4-NHSO_2-C_6H_5$ | H |
| 209 | " | H | $-(CH_2)_6-NHSO_2-C_6H_5$ | H |
| 210 | " | H | $-(CH_2)_2-NHSO_2-C_6H_4-p-CH_3$ | H |
| 211 | " | H | $-(CH_2)_2-NHSO_2-C_6H_4-m-CH_3$ | H |
| 212 | " | H | $-(CH_2)_2-NHSO_2-C_6H_4-o-CH_3$ | H |
| 213 | " | H | $-(CH_2)_2-NHSO_2-C_6H_4-p-Cl$ | H |
| 214 | " | H | $-(CH_2)_2-NHSO_2-C_6H_4-p-OH$ | H |
| 215 | " | H | $-(CH_2)_2-NHSO_2-C_6H_4-p-NO_2$ | H |
| 216 | " | H | $-(CH_2)_2-NHSO_2-C_6H_4-p-NH_2$ | H |
| 217 | " | H | $-(CH_2)_4-NHSO_2-C_6H_4-p-CH_3$ | H |

TABLE 1-continued
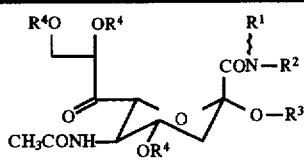
| Compound No. | R¹ | R² | R³ | R⁴ |
|---|---|---|---|---|
| 218 | " | H | $-(CH_2)_6-NHSO_2-$C_6H_4-CH_3 | H |
| 219 | " | H | $-(CH_2)_2-NHCOOCH_3$ | H |
| 220 | " | H | $-(CH_2)_2-NHCOOCH_2CH_3$ | H |
| 221 | " | H | $-(CH_2)_2-NHCOO-C(CH_3)_3$ | H |
| 222 | " | H | $-(CH_2)_2-NHCOOCH_2-C_6H_5$ | $-COCH_3$ |
| 223 | " | H | $-(CH_2)_2-NHCOOCH_2-C_6H_5$ | H |
| 224 | cholesteryl | H | $-(CH_2)_4-NHCOOCH_3$ | H |
| 225 | " | H | $-(CH_2)_4-NHCOOC(CH_3)_3$ | H |
| 227 | " | H | $-(CH_2)_4-NHCOOCH_2-C_6H_5$ | H |
| 228 | " | H | $-(CH_2)_6-NHCOOCH_3$ | H |
| 229 | " | H | $-(CH_2)_6-NHCOOC(CH_3)_3$ | H |
| 230 | " | H | $-(CH_2)_6-NHCOOCH_2-C_6H_5$ | H |
| 231 | cholesteryl | H | $-CH_3$ | $-COCH_3$ |
| 232 | " | H | $-CH_3$ | $-COCH_2CH_3$ |

TABLE 1-continued
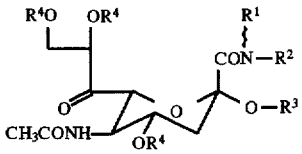
| Compound No. | R¹ | R² | R³ | R⁴ |
|---|---|---|---|---|
| 233 | " | H | —CH₃ | —CO—C₆H₅ |
| 234 | " | H | —CH₃ | H |
| 235 | " | —CH₃ | —CH₃ | —COCH₃ |
| 236 | 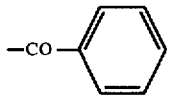 | —CH₃ | —CH₃ | H |
| 237 | " | —CH₂CH₃ | —CH₃ | H |
| 238 | " | —(CH₂)₂CH₃ | —CH₃ | H |
| 239 | " | —(CH₂)₃CH₃ | —CH₃ | H |
| 240 | " | H | —CH₂CH₃ | H |
| 241 | " | H | —(CH₂)₂CH₃ | H |
| 242 | " | H | —(CH₂)₅CH₃ | H |
| 243 | " | H | —(CH₂)₉—CH₃ | H |
| 244 | " | H | —(CH₂)₁₄—CH₃ | H |
| 245 | " | H | 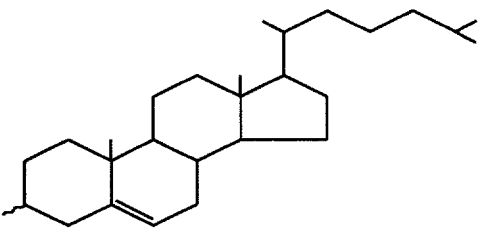 | H |
| 246 | " | H | —CH₂—C₆H₅ | H |
| 247 | 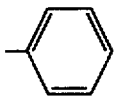 | H | —(CH₂)₂OH | H |
| 248 | " | H | —(CH₂)₂—NH₂ | H |

TABLE 2
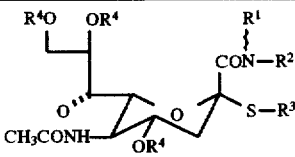
| Compound No. | R¹ | R² | R³ | R⁴ |
|---|---|---|---|---|
| 249 | cholestanyl | H | —CH₃ | —COCH₃ |
| 250 | " | H | —CH₃ | —COCH₂CH₃ |
| 251 | " | H | —CH₃ | —CO—C₆H₅ |
| 252 | " | H | —CH₃ | H |
| 253 | " | CH₃ | —CH₃ | H |
| 254 | " | H | —CH₂CH₃ | H |
| 255 | " | H | ─(CH₂)₅—CH₃ | —COCH₃ |
| 256 | " | H | ─(CH₂)₅—CH₃ | H |
| 257 | " | H | ─(CH₂)₉—CH₃ | H |
| 258 | " | H | ─(CH₂)₁₄—CH₃ | H |
| 259 | " | H | —C₆H₅ | —COCH₃ |
| 260 | cholestanyl | H | —C₆H₅ | H |
| 261 | " | H | —CH₂—C₆H₅ | H |
| 262 | " | H | ─(CH₂)₂—OH | H |
| 263 | " | H | ─(CH₂)₂—NH₂ | H |
| 264 | cholesteryl | H | —CH₃ | H |

TABLE 3
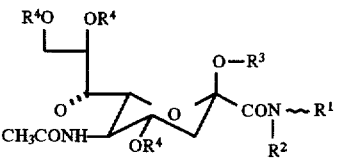
| Compound No. | R$^1$ | R$^2$ | R$^3$ | R$^4$ |
|---|---|---|---|---|
| 265 | 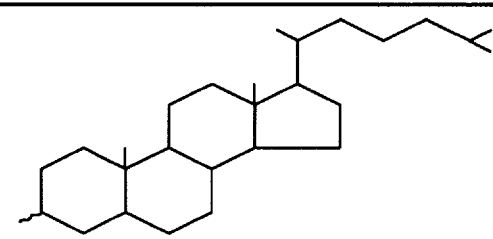 | H | —CH$_3$ | —COCH$_3$ |
| 266 | " | H | —CH$_3$ | —COCH$_2$CH$_3$ |
| 267 | " | H | —CH$_3$ | —CO—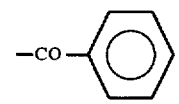 |
| 268 | " | H | —CH$_3$ | H |
| 269 | " | —CH$_3$ | —CH$_3$ | —COCH$_3$ |
| 270 | " | —CH$_3$ | —CH$_3$ | H |
| 271 | " | —CH$_2$CH$_3$ | —CH$_3$ | H |
| 272 | " | ᜓCH$_2$)$_2$CH$_3$ | —CH$_3$ | H |
| 273 | " | ᜓCH$_2$)$_3$—CH$_3$ | —CH$_3$ | H |
| 274 | " | H | —CH$_2$CH$_3$ | H |
| 275 | " | H | ᜓCH$_2$)$_2$—CH$_3$ | H |
| 276 | 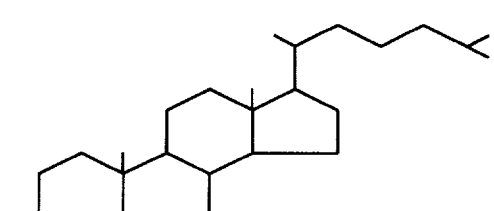 | H | ᜓCH$_2$)$_5$—CH$_3$ | H |
| 277 | " | H | ᜓCH$_2$)$_9$—CH$_3$ | H |
| 278 | " | H | ᜓCH$_2$)$_{14}$—CH$_3$ | H |
| 279 | " | H | 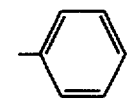 | H |
| 280 | " | H | —CH$_2$—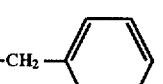 | —COCH$_3$ |
| 281 | " | H | —CH$_2$—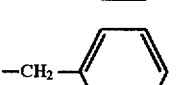 | H |
| 282 | " | H | ᜓCH$_2$)$_2$OH | H |
| 283 | " | H | ᜓCH$_2$)$_2$NH$_2$ | H |

TABLE 3-continued
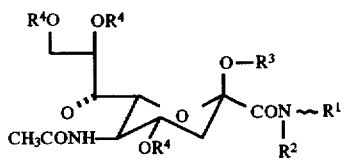
| Compound No. | R¹ | R² | R³ | R⁴ |
|---|---|---|---|---|
| 284 | (cholesteryl) | H | —CH₃ | H |
TABLE 4
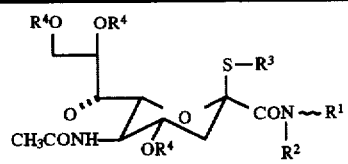
| Compound No. | R¹ | R² | R³ | R⁴ |
|---|---|---|---|---|
| 285 | (cholesteryl) | H | —CH₃ | —COCH₃ |
| 286 | " | H | —CH₃ | —COCH₂CH₃ |
| 287 | " | H | —CH₃ | —CO—C₆H₅ |
| 288 | " | H | —CH₃ | H |
| 289 | " | —CH₃ | —CH₃ | H |
| 290 | " | H | —CH₂CH₃ | H |
| 291 | " | H | ${+CH_2)_5}$—CH₃ | H |
| 292 | " | H | ${+CH_2)_9}$—CH₃ | H |
| 293 | " | H | ${+CH_2)_{14}}$—CH₃ | H |
| 294 | " | H | —C₆H₅ | —COCH₃ |
| 295 | " | H | —C₆H₅ | H |

TABLE 4-continued

[Structure: sugar ring with R⁴O, OR⁴, CH₃CONH—, OR⁴, S—R³, CON(R¹)(R²)]

| Compound No. | R¹ | R² | R³ | R⁴ |
|---|---|---|---|---|
| 296 | cholestanyl (saturated steroid) | H | —CH₂—C₆H₅ | H |
| 297 | " | H | —(CH₂)₂OH | H |
| 298 | " | H | —(CH₂)₂—NH₂ | H |
| 299 | cholesteryl (Δ5-steroid) | H | —CH₃ | H |

TABLE 5

[Structure: sugar ring with R⁴O, OR⁴, R⁴O, R⁵, OR⁴, OCH₃, CON—H linked to cholestanyl steroid]

| Compound | R⁴ | R⁵ |
|---|---|---|
| 300 | H | CH₃CH₂C(=O)NH— |
| 301 | H | CH₃(CH₂)₂C(=O)NH— |
| 302 | H | (CH₃)₂CHC(=O)NH— |
| 303 | H | CH₃(CH₂)₃C(=O)NH— |

TABLE 5-continued

[Structure: sugar ring with R⁴O, OR⁴, R⁴O, R⁵, OR⁴, OCH₃, CON—H linked to cholesteryl steroid]

| Compound | R⁴ | R⁵ |
|---|---|---|
| 304 | H | (CH₃)₂CHCH₂C(=O)NH— |
| 305 | H | (CH₃)₃CC(=O)NH— |
| 306 | H | CH₃(CH₂)₄C(=O)NH— |
| 307 | H | CH₃(CH₂)₅C(=O)NH— |

TABLE 5-continued

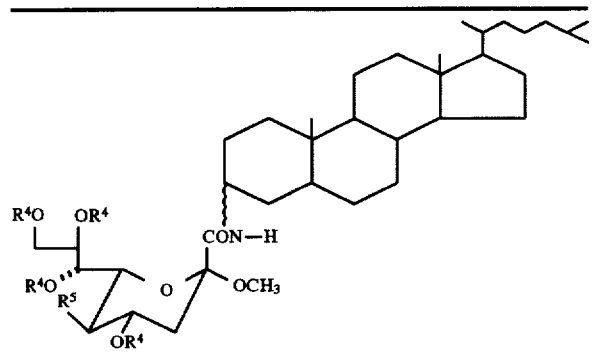

| Compound | R⁴ | R⁵ |
|---|---|---|
| 308 | H | HOCH₂CNH— (C=O) |
| 309 | H | CH₃OCH₂CNH— (C=O) |
| 310 | H | CH₃CH₂OCH₂CNH— (C=O) |
| 311 | H | CH₃(CH₂)₂OCH₂CNH— (C=O) |
| 312 | H | CH₃(CH₂)₅OCH₂CNH— (C=O) |
| 313 | H | C₆H₅-OCH₂CNH— (C=O) |
| 314 | H | C₆H₅-CH₂OCH₂CNH— (C=O) |
| 315 | H | C₆H₅-(CH₂)₂OCNH— (C=O) |
| 316 | H | C₆H₅-(CH₂)₃OCH₂CNH— (C=O) |
| 317 | H | HO(CH₂)₂CNH— (C=O) |
| 318 | H | HO(CH₂)₃CNH— (C=O) |
| 319 | H | HO(CH₂)₄CNH— (C=O) |
| 320 | H | CH₃OCNH— (C=O) |
| 321 | H | CH₃CH₂OCNH— (C=O) |

TABLE 5-continued

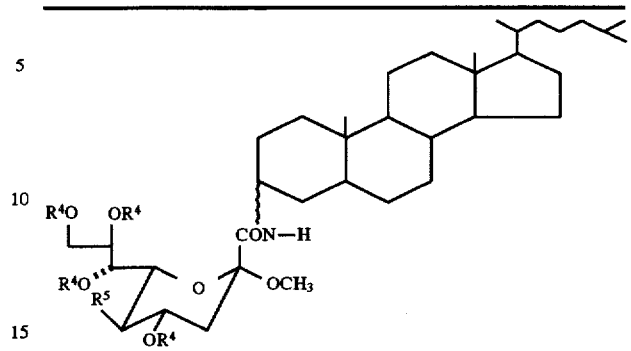

| Compound | R⁴ | R⁵ |
|---|---|---|
| 322 | H | CH₃(CH₂)₂OCNH— (C=O) |
| 323 | H | CH₃(CH₂)₃OCNH— (C=O) |
| 324 | H | (CH₃)₃COCNH— (C=O) |
| 325 | H | C₆H₅-CNH— (C=O) |
| 326 | H | C₆H₅-(CH₂)₂OCNH— (C=O) |
| 327 | H | C₆H₅-(CH₂)₃OCNH— (C=O) |
| 328 | H | C₆H₅-CNH— (C=O) |
| 329 | H | 2-naphthyl-CNH— (C=O) |
| 330 | H | 1-naphthyl-C(=O)NH— |
| 331 | H | 4-H₃C-C₆H₄-CNH— (C=O) |
| 332 | H | 3-H₃C-C₆H₄-CNH— (C=O) |

TABLE 5-continued

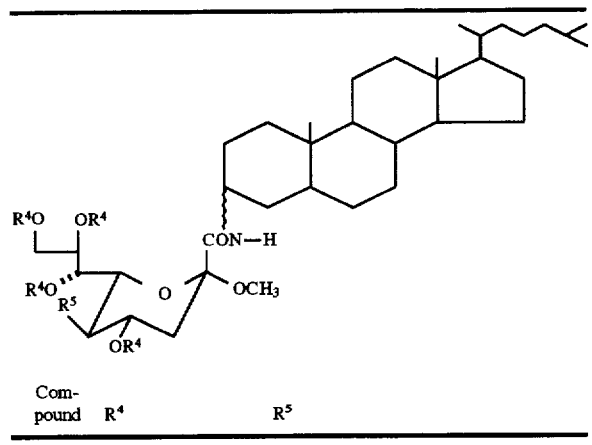

| Compound | R⁴ | R⁵ |
|---|---|---|
| 333 | H | 2-methyl-benzamide (o-CH₃-C₆H₄-CONH-) |
| 334 | H | 4-ethyl-benzamide (CH₃CH₂-C₆H₄-CONH-) |
| 335 | H | 4-isopropyl-benzamide (CH₃(CH₂)₂-C₆H₄-CONH-) |
| 336 | H | 4-butyl-benzamide (CH₃(CH₂)₃-C₆H₄-CONH-) |
| 337 | H | 4-chloro-benzamide (Cl-C₆H₄-CONH-) |
| 338 | H | 4-hydroxy-benzamide (HO-C₆H₄-CONH-) |
| 339 | H | 4-nitro-benzamide (O₂N-C₆H₄-CONH-) |
| 340 | H | 4-amino-benzamide (H₂N-C₆H₄-CONH-) |
| 341 | H | 4-carboxy-benzamide (HOOC-C₆H₄-CONH-) |
| 342 | H | phenylacetamide (C₆H₅-CH₂-CONH-) |

TABLE 5-continued

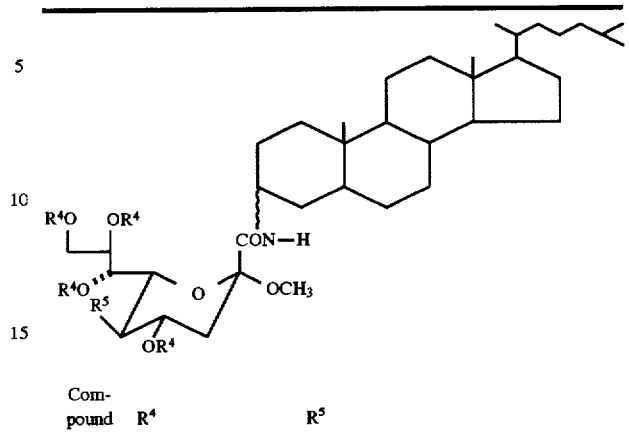

| Compound | R⁴ | R⁵ |
|---|---|---|
| 343 | H | C₆H₅-(CH₂)₂-CONH- |
| 344 | H | C₆H₅-(CH₂)₃-CONH- |
| 345 | H | 4-methyl-phenylacetamide (H₃C-C₆H₄-CH₂-CONH-) |
| 346 | H | 4-chloro-phenylacetamide (Cl-C₆H₄-CH₂-CONH-) |
| 347 | H | 4-hydroxy-phenylacetamide (OH-C₆H₄-CH₂-CONH-) |
| 348 | H | 4-nitro-phenylacetamide (O₂N-C₆H₄-CH₂-CONH-) |
| 349 | H | 4-amino-phenylacetamide (H₂N-C₆H₄-CH₂-CONH-) |
| 350 | H | 4-carboxy-phenylacetamide (HOOC-C₆H₄-CH₂-CONH-) |
| 351 | H | H₃C-SO₂-NH- |
| 352 | H | CH₃CH₂-SO₂-NH- |

TABLE 5-continued

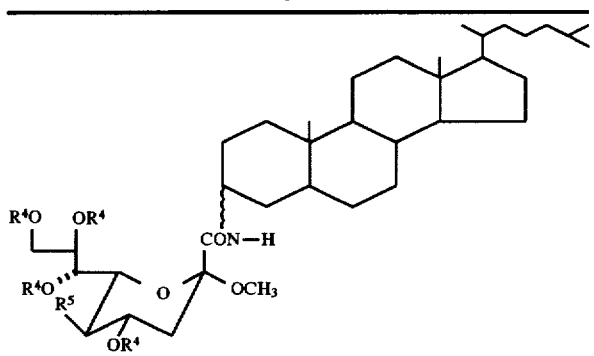
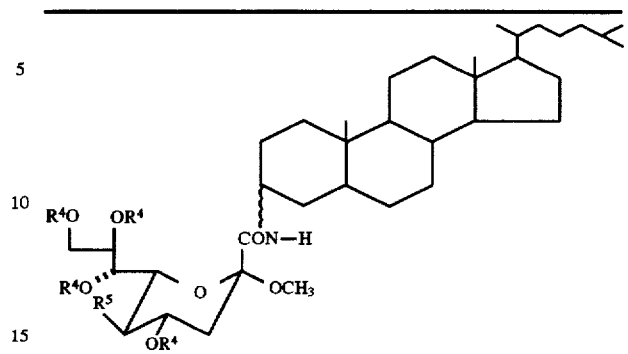

| Compound | R⁴ | R⁵ |
|---|---|---|
| 353 | H | CH₃(CH₂)₂—S(=O)₂—NH— |
| 354 | H | CH₃(CH₂)₃—S(=O)₂—NH— |
| 355 | H | C₆H₅—S(=O)₂—NH— |
| 356 | H | 4-H₃C-C₆H₄—S(=O)₂—NH— |
| 357 | H | 3-H₃C-C₆H₄—S(=O)₂—NH— |
| 358 | H | 2-H₃C-C₆H₄—S(=O)₂—NH— |
| 359 | H | 4-CH₃CH₂-C₆H₄—S(=O)₂—NH— |
| 360 | H | 4-CH₃(CH₂)₂-C₆H₄—S(=O)₂—NH— |
| 361 | H | 4-CH₃(CH₂)₃-C₆H₄—S(=O)₂—NH— |
| 362 | H | 4-Cl-C₆H₄—S(=O)₂—NH— |

| Compound | R⁴ | R⁵ |
|---|---|---|
| 363 | H | 4-HO-C₆H₄—S(=O)₂—NH— |
| 364 | H | 4-O₂N-C₆H₄—S(=O)₂—NH— |
| 365 | H | 4-H₂N-C₆H₄—S(=O)₂—NH— |
| 366 | H | 4-HOOC-C₆H₄—S(=O)₂—NH— |
| 367 | H | HO— |
| 368 | CH₃C(=O)— | CH₃CH₂C(=O)NH— |
| 369 | CH₃C(=O)— | CH₃(CH₂)₂C(=O)NH— |
| 370 | CH₃C(=O)— | (CH₃)₂CHC(=O)NH— |
| 371 | CH₃C(=O)— | CH₃(CH₂)₂C(=O)NH— |
| 372 | CH₃C(=O)— | (CH₃)₂CHCH₂C(=O)NH— |
| 373 | CH₃C(=O)— | (CH₃)₃CC(=O)NH— |
| 374 | CH₃C(=O)— | CH₃(CH₂)₄C(=O)NH— |
| 375 | CH₃C(=O)— | CH₃(CH₂)₅C(=O)NH— |
| 376 | CH₃C(=O)— | HOCH₂C(=O)NH— |

TABLE 5-continued

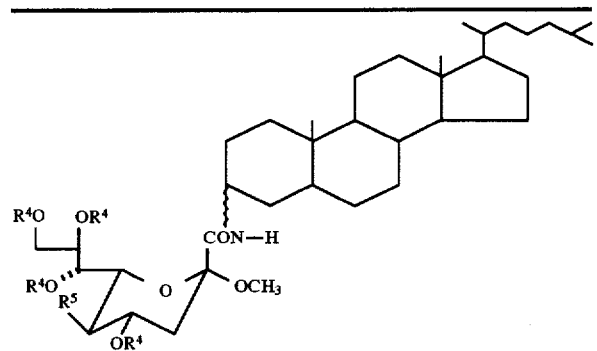

| Compound | $R^4$ | $R^5$ |
|---|---|---|
| 377 | $CH_3\overset{O}{\underset{\|}{C}}-$ | $CH_3OCH_2\overset{O}{\underset{\|}{C}}NH-$ |
| 378 | $CH_3\overset{O}{\underset{\|}{C}}-$ | $CH_3CH_2OCH_2\overset{O}{\underset{\|}{C}}NH-$ |
| 379 | $CH_3\overset{O}{\underset{\|}{C}}-$ | $CH_3(CH_2)_2OCH_2\overset{O}{\underset{\|}{C}}NH-$ |
| 380 | $CH_3\overset{O}{\underset{\|}{C}}-$ | $CH_3(CH_2)_5OCH_2\overset{O}{\underset{\|}{C}}NH-$ |
| 381 | $CH_3\overset{O}{\underset{\|}{C}}-$ | Ph-$OCH_2\overset{O}{\underset{\|}{C}}NH-$ |
| 382 | $CH_3\overset{O}{\underset{\|}{C}}-$ | Ph-$CH_2OCH_2\overset{O}{\underset{\|}{C}}NH-$ |
| 383 | $CH_3\overset{O}{\underset{\|}{C}}-$ | Ph-$(CH_2)_2O\overset{O}{\underset{\|}{C}}NH-$ |
| 384 | $CH_3\overset{O}{\underset{\|}{C}}-$ | Ph-$(CH_2)_3OCH_2\overset{O}{\underset{\|}{C}}NH-$ |
| 385 | $CH_3\overset{O}{\underset{\|}{C}}-$ | $HO(CH_2)_2\overset{O}{\underset{\|}{C}}NH-$ |
| 386 | $CH_3\overset{O}{\underset{\|}{C}}-$ | $HO(CH_2)_3\overset{O}{\underset{\|}{C}}NH-$ |
| 387 | $CH_3\overset{O}{\underset{\|}{C}}-$ | $HO(CH_2)_4\overset{O}{\underset{\|}{C}}NH-$ |
| 388 | $CH_3\overset{O}{\underset{\|}{C}}-$ | $CH_3O\overset{O}{\underset{\|}{C}}NH-$ |
| 389 | $CH_3\overset{O}{\underset{\|}{C}}-$ | $CH_3CH_2O\overset{O}{\underset{\|}{C}}NH-$ |
| 390 | $CH_3\overset{O}{\underset{\|}{C}}-$ | $CH_3(CH_2)_2O\overset{O}{\underset{\|}{C}}NH-$ |

TABLE 5-continued

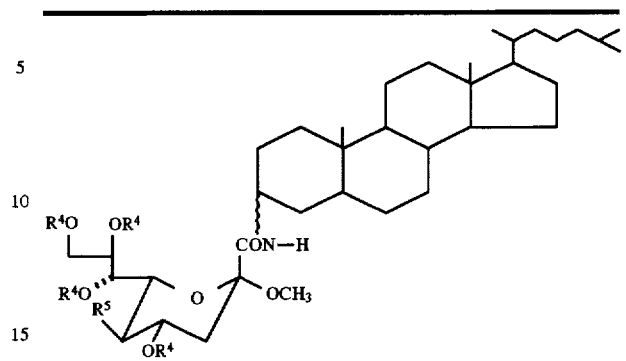

| Compound | $R^4$ | $R^5$ |
|---|---|---|
| 391 | $CH_3\overset{O}{\underset{\|}{C}}-$ | $CH_3(CH_2)_3O\overset{O}{\underset{\|}{C}}NH-$ |
| 392 | $CH_3\overset{O}{\underset{\|}{C}}-$ | $(CH_3)_3CO\overset{O}{\underset{\|}{C}}NH-$ |
| 393 | $CH_3\overset{O}{\underset{\|}{C}}-$ | Ph-$CH_2O\overset{O}{\underset{\|}{C}}NH-$ |
| 394 | $CH_3\overset{O}{\underset{\|}{C}}-$ | Ph-$(CH_2)_2O\overset{O}{\underset{\|}{C}}NH-$ |
| 395 | $CH_3\overset{O}{\underset{\|}{C}}-$ | Ph-$(CH_2)_3O\overset{O}{\underset{\|}{C}}NH-$ |
| 396 | $CH_3\overset{O}{\underset{\|}{C}}-$ | Ph-$\overset{O}{\underset{\|}{C}}NH-$ |
| 397 | $CH_3\overset{O}{\underset{\|}{C}}-$ | 2-naphthyl-$\overset{O}{\underset{\|}{C}}NH-$ |
| 398 | $CH_3\overset{O}{\underset{\|}{C}}-$ | 1-naphthyl-$\overset{O}{\underset{\|}{C}}NH-$ |
| 399 | $CH_3\overset{O}{\underset{\|}{C}}-$ | 4-$CH_3$-Ph-$\overset{O}{\underset{\|}{C}}NH-$ |
| 400 | $CH_3\overset{O}{\underset{\|}{C}}-$ | 3-$CH_3$-Ph-$\overset{O}{\underset{\|}{C}}NH-$ |

TABLE 5-continued

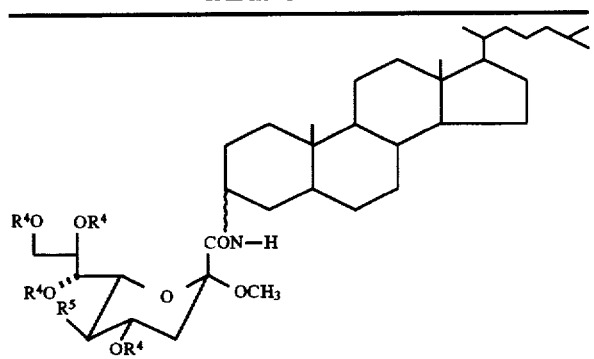

| Compound | R⁴ | R⁵ |
|---|---|---|
| 401 | CH₃C(O)– | 2-methylphenyl-C(O)NH– |
| 402 | CH₃C(O)– | 4-ethylphenyl-C(O)NH– |
| 403 | CH₃C(O)– | 4-(CH₃(CH₂)₂)phenyl-C(O)NH– |
| 404 | CH₃C(O)– | 4-(CH₃(CH₂)₃)phenyl-C(O)NH– |
| 405 | CH₃C(O)– | 4-chlorophenyl-C(O)NH– |
| 406 | CH₃C(O)– | 4-hydroxyphenyl-C(O)NH– |
| 407 | CH₃C(O)– | 4-nitrophenyl-C(O)NH– |
| 408 | CH₃C(O)– | 4-aminophenyl-C(O)NH– |
| 409 | CH₃C(O)– | 4-carboxyphenyl-C(O)NH– |
| 410 | CH₃C(O)– | phenyl-CH₂C(O)NH– |
| 411 | CH₃C(O)– | phenyl-(CH₂)₂C(O)NH– |
| 412 | CH₃C(O)– | phenyl-(CH₂)₃C(O)NH– |
| 413 | CH₃C(O)– | 4-methylphenyl-CH₂C(O)NH– |
| 414 | CH₃C(O)– | 4-chlorophenyl-CH₂C(O)NH– |
| 415 | CH₃C(O)– | 4-hydroxyphenyl-CH₂C(O)NH– |
| 416 | CH₃C(O)– | 4-nitrophenyl-CH₂C(O)NH– |
| 417 | CH₃C(O)– | 3-aminophenyl-CH₂C(O)NH– |
| 418 | CH₃C(O)– | 4-carboxyphenyl-CH₂C(O)NH– |
| 419 | CH₃C(O)– | H₃C–S(O)₂–NH– |
| 420 | CH₃C(O)– | CH₃CH₂–S(O)₂–NH– |

TABLE 5-continued

[Structure: steroid attached to sugar with R⁴O, OR⁴, R⁵, OR⁴ substituents, CON—H linker, OCH₃]

| Compound | R⁴ | R⁵ |
|---|---|---|
| 421 | CH₃C(=O)— | CH₃(CH₂)₂—S(=O)₂—NH— |
| 422 | CH₃C(=O)— | CH₃(CH₂)₃—S(=O)₂—NH— |
| 423 | CH₃C(=O)— | C₆H₅—S(=O)₂—NH— |
| 424 | CH₃C(=O)— | 4-H₃C-C₆H₄—S(=O)₂—NH— |
| 425 | CH₃C(=O)— | 3-H₃C-C₆H₄—S(=O)₂—NH— |
| 426 | CH₃C(=O)— | 2-CH₃-C₆H₄—S(=O)₂—NH— |
| 427 | CH₃C(=O)— | CH₃CH₂-C₆H₄—S(=O)₂—NH— |
| 428 | CH₃C(=O)— | CH₃(CH₂)₂-C₆H₄—S(=O)₂—NH— |
| 429 | CH₃C(=O)— | CH₃(CH₂)₃-C₆H₄—S(=O)₂—NH— |
| 430 | CH₃C(=O)— | Cl-C₆H₄—S(=O)₂—NH— |
| 431 | CH₃C(=O)— | HO-C₆H₄—S(=O)₂—NH— |
| 432 | CH₃C(=O)— | O₂N-C₆H₄—S(=O)₂—NH— |
| 433 | CH₃C(=O)— | H₂N-C₆H₄—S(=O)₂—NH— |
| 434 | CH₃C(=O)— | HOOC-C₆H₄—S(=O)₂—NH— |
| 435 | CH₃C(=O)— | CH₃CO— |
| 436 | CH₃CH₂C(=O)— | CH₃CH₂CO— |
| 437 | C₆H₅C(=O)— | C₆H₅CO— |

TABLE 6

| Compound | R⁴ | R⁵ |
|---|---|---|
| 438 | H | HO— |
| 439 | CH₃C(=O)— | CH₃CO(=O)— |

TABLE 7

| Compound | R⁴ | R⁵ |
|---|---|---|
| 440 | H | CH₃CH₂CNH— (C=O) |
| 441 | H | CH₃(CH₂)₂CNH— (C=O) |
| 442 | H | (CH₃)₂CHCNH— (C=O) |
| 443 | H | CH₃(CH₂)₃CNH— (C=O) |
| 444 | H | (CH₃)₂CHCH₂CNH— (C=O) |
| 445 | H | (CH₃)₃CCNH— (C=O) |
| 446 | H | CH₃(CH₂)₄CNH— (C=O) |
| 447 | H | CH₃(CH₂)₅CNH— (C=O) |
| 448 | H | HOCH₂CNH— (C=O) |

TABLE 7-continued

| Compound | R⁴ | R⁵ |
|---|---|---|
| 449 | H | CH₃OCH₂C(O)NH— |
| 450 | H | CH₃CH₂OCH₂C(O)NH— |
| 451 | H | CH₃(CH₂)₂OCH₂C(O)NH— |
| 452 | H | CH₃(CH₂)₅OCH₂C(O)NH— |
| 453 | H | C₆H₅—OCH₂C(O)NH— |
| 454 | H | C₆H₅—CH₂OCH₂C(O)NH— |
| 455 | H | C₆H₅—(CH₂)₂OC(O)NH— |
| 456 | H | C₆H₅—(CH₂)₃OCH₂C(O)NH— |
| 457 | H | HO(CH₂)₂C(O)NH— |
| 458 | H | HO(CH₂)₃C(O)NH— |
| 459 | H | HO(CH₂)₄C(O)NH— |
| 460 | H | CH₃OC(O)NH— |
| 461 | H | CH₃CH₂OC(O)NH— |
| 462 | H | CH₃(CH₂)₂OC(O)NH— |

TABLE 7-continued

[Structure: steroid-CONH- linked to a sugar ring with OR⁴ groups, R₅ substituent, and OCH₃]

| Compound | R⁴ | R⁵ |
|---|---|---|
| 463 | H | CH₃(CH₂)₃OC(=O)NH— |
| 464 | H | (CH₃)₃COC(=O)NH— |
| 465 | H | C₆H₅-CH₂OC(=O)NH— |
| 466 | H | C₆H₅-(CH₂)₂OC(=O)NH— |
| 467 | H | C₆H₅-(CH₂)₃OC(=O)NH— |
| 468 | H | C₆H₅-C(=O)NH— |
| 469 | H | 2-naphthyl-C(=O)NH— |
| 470 | H | 1-naphthyl-C(=O)NH— |
| 471 | H | 4-CH₃-C₆H₄-C(=O)NH— |
| 472 | H | 3-CH₃-C₆H₄-C(=O)NH— |
| 473 | H | 2-CH₃-C₆H₄-C(=O)NH— |

TABLE 7-continued
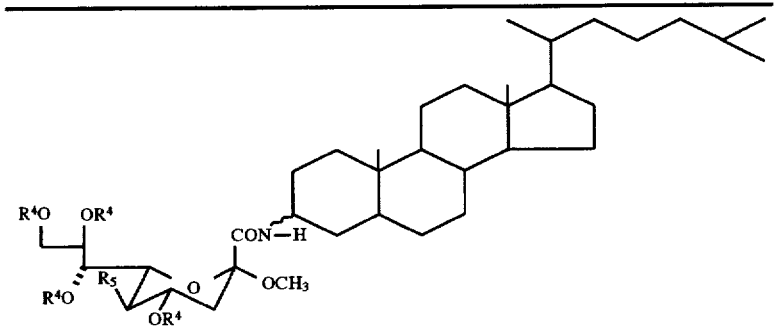
| Compound | R[4] | R[5] |
|---|---|---|
| 474 | H | 4-(CH$_3$CH$_2$)-C$_6$H$_4$-C(O)NH— |
| 475 | H | 4-(CH$_3$(CH$_2$)$_2$)-C$_6$H$_4$-C(O)NH— |
| 476 | H | 4-(CH$_3$(CH$_2$)$_3$)-C$_6$H$_4$-C(O)NH— |
| 477 | H | 4-Cl-C$_6$H$_4$-C(O)NH— |
| 478 | H | 4-HO-C$_6$H$_4$-C(O)NH— |
| 479 | H | 4-O$_2$N-C$_6$H$_4$-C(O)NH— |
| 480 | H | 4-H$_2$N-C$_6$H$_4$-C(O)NH— |
| 481 | H | 4-HOOC-C$_6$H$_4$-C(O)NH— |
| 482 | H | C$_6$H$_5$-CH$_2$C(O)NH— |
| 483 | H | C$_6$H$_5$-(CH$_2$)$_2$C(O)NH— |
| 484 | H | C$_6$H$_5$-(CH$_2$)$_3$C(O)NH— |

TABLE 7-continued

| Compound | R⁴ | R⁵ |
|---|---|---|
| 485 | H | 4-CH₃-C₆H₄-CH₂C(O)NH— |
| 486 | H | 4-Cl-C₆H₄-CH₂C(O)NH— |
| 487 | H | 4-HO-C₆H₄-CH₂C(O)NH— |
| 488 | H | 4-O₂N-C₆H₄-CH₂C(O)NH— |
| 489 | H | 4-H₂N-C₆H₄-CH₂C(O)NH— |
| 490 | H | 4-HOOC-C₆H₄-CH₂C(O)NH— |
| 491 | H | CH₃-S(O)₂-NH— |
| 492 | H | CH₃CH₂-S(O)₂-NH— |
| 493 | H | CH₃(CH₂)₂-S(O)₂-NH— |
| 494 | H | CH₃(CH₂)₃-S(O)₂-NH— |
| 495 | H | C₆H₅-S(O)₂-NH— |

TABLE 7-continued

[Structure shown: steroid (cholestane-type) attached via CONH to a sugar-like ring system bearing R⁴O, OR⁴, OR⁴ groups, R⁵ substituent, and OCH₃]

| Compound | R⁴ | R⁵ |
|----------|----|----|
| 496 | H | 4-CH₃-C₆H₄-S(O)₂-NH- |
| 497 | H | 3-CH₃-C₆H₄-S(O)₂-NH- |
| 498 | H | 2-CH₃-C₆H₄-S(O)₂-NH- |
| 499 | H | 4-CH₃CH₂-C₆H₄-S(O)₂-NH- |
| 500 | H | 4-CH₃(CH₂)₂-C₆H₄-S(O)₂-NH- |
| 501 | H | 4-CH₃(CH₂)₃-C₆H₄-S(O)₂-NH- |
| 502 | H | 4-Cl-C₆H₄-S(O)₂-NH- |
| 503 | H | 4-HO-C₆H₄-S(O)₂-NH- |
| 504 | H | 4-O₂N-C₆H₄-S(O)₂-NH- |
| 505 | H | 4-H₂N-C₆H₄-S(O)₂-NH- |

TABLE 7-continued

[Structure: steroid with side chain connected via CON-H to a cyclic sugar moiety bearing R⁴O, OR⁴, R⁵ substituents, OCH₃ group]

| Compound | R⁴ | R⁵ |
|---|---|---|
| 506 | H | HOOC-C₆H₄-S(=O)₂-NH— |
| 507 | H | HO— |
| 508 | CH₃C(=O)— | CH₃CH₂C(=O)NH— |
| 509 | CH₃C(=O)— | CH₃(CH₂)₂C(=O)NH— |
| 510 | CH₃C(=O)— | (CH₃)₂CHC(=O)NH— |
| 511 | CH₃C(=O)— | CH₃(CH₂)₃C(=O)NH— |
| 512 | CH₃C(=O)— | (CH₃)₂CHCH₂C(=O)NH— |
| 513 | CH₃C(=O)— | (CH₃)₃CC(=O)NH— |
| 514 | CH₃C(=O)— | CH₃C(=O)— |
| 515 | CH₃C(=O)— | CH₃(CH₂)₄C(=O)NH— |
| 516 | CH₃C(=O)— | CH₃(CH₂)₅C(=O)NH— |
| 517 | CH₃C(=O)— | HOCH₂C(=O)NH— |
| 518 | CH₃C(=O)— | CH₃OCH₂C(=O)NH— |
| 519 | CH₃C(=O)— | CH₃CH₂OCH₂C(=O)NH— |
| 520 | CH₃C(=O)— | CH₃(CH₂)₂OCH₂C(=O)NH— |
| 521 | CH₃C(=O)— | CH₃(CH₂)₅OCH₂C(=O)NH— |

TABLE 7-continued

[Structure diagram showing steroid with R⁴O, OR⁴, R₅, OR⁴, OCH₃, CON—H substituents]

| Compound | R⁴ | R⁵ |
|---|---|---|
| 522 | CH₃C(=O)— | Ph-OCH₂C(=O)NH— |
| 522 | CH₃C(=O)— | Ph-CH₂OCH₂C(=O)NH— |
| 523 | CH₃C(=O)— | Ph-(CH₂)₂OCNH— |
| 524 | CH₃C(=O)— | Ph-(CH₂)₃OCH₂C(=O)NH— |
| 525 | CH₃C(=O)— | HO(CH₂)₂C(=O)NH— |
| 526 | CH₃C(=O)— | HO(CH₂)₃C(=O)NH— |
| 527 | CH₃C(=O)— | HO(CH₂)₄C(=O)NH— |
| 528 | CH₃C(=O)— | CH₃OCNH— |
| 529 | CH₃C(=O)— | CH₃CH₂OCNH— |
| 530 | CH₃C(=O)— | CH₃(CH₂)₂OCNH— |
| 531 | CH₃C(=O)— | CH₃(CH₂)₃OCNH— |
| 532 | CH₃C(=O)— | (CH₃)₃COCNH— |
| 533 | CH₃C(=O)— | Ph-CH₂OCNH— |

TABLE 7-continued
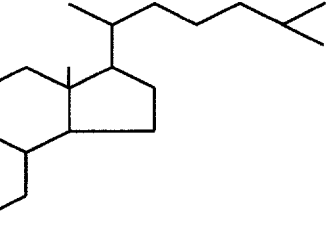
| Compound | R⁴ | R⁵ |
|---|---|---|
| 534 | CH₃C(O)— | C₆H₅(CH₂)₂OC(O)NH— |
| 535 | CH₃C(O)— | C₆H₅(CH₂)₃OC(O)NH— |
| 536 | CH₃C(O)— | C₆H₅C(O)NH— |
| 537 | CH₃C(O)— | 2-naphthyl-C(O)NH— |
| 538 | CH₃C(O)— | 1-naphthyl-C(O)NH— |
| 539 | CH₃C(O)— | 4-CH₃-C₆H₄-C(O)NH— |
| 540 | CH₃C(O)— | 3-CH₃-C₆H₄-C(O)NH— |
| 541 | CH₃C(O)— | 2-CH₃-C₆H₄-C(O)NH— |
| 542 | CH₃C(O)— | 4-CH₃CH₂-C₆H₁₀-C(O)NH— |
| 543 | CH₃C(O)— | 4-CH₃(CH₂)₂-C₆H₄-C(O)NH— |

TABLE 7-continued
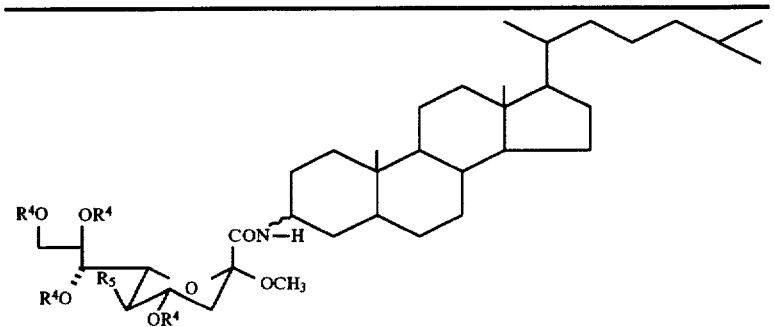
| Compound | R⁴ | R⁵ |
|---|---|---|
| 544 | CH₃C(O)— | CH₃(CH₂)₃—C₆H₄—C(O)NH— |
| 545 | CH₃C(O)— | Cl—C₆H₄—C(O)NH— |
| 546 | CH₃C(O)— | HO—C₆H₄—C(O)NH— |
| 547 | CH₃C(O)— | O₂N—C₆H₄—C(O)NH— |
| 548 | CH₃C(O)— | H₂N—C₆H₄—C(O)NH— |
| 549 | CH₃C(O)— | HOOC—C₆H₄—C(O)NH— |
| 550 | CH₃C(O)— | C₆H₅—CH₂C(O)NH— |
| 551 | CH₃C(O)— | C₆H₅—(CH₂)₂C(O)NH— |
| 552 | CH₃C(O)— | C₆H₅—(CH₂)₃C(O)NH— |
| 553 | CH₃C(O)— | H₃C—C₆H₄—CH₂C(O)NH— |
| 554 | CH₃C(O)— | Cl—C₆H₄—CH₂C(O)NH— |

TABLE 7-continued

[Structure shown: steroid-containing compound with R⁴O, OR⁴ groups, R₅ substituent, OCH₃, and CON—H linkage]

| Compound | R⁴ | R⁵ |
|---|---|---|
| 555 | CH₃C(=O)— | HO—C₆H₄—CH₂C(=O)NH— |
| 556 | CH₃C(=O)— | O₂N—C₆H₄—CH₂C(=O)NH— |
| 557 | CH₃C(=O)— | H₂N—C₆H₄—CH₂C(=O)NH— |
| 558 | CH₃C(=O)— | HOOC—C₆H₄—CH₂C(=O)NH— |
| 559 | CH₃C(=O)— | H₃—S(=O)₂—NH— |
| 560 | CH₃C(=O)— | CH₃CH₂—S(=O)₂—NH— |
| 561 | CH₃C(=O)— | CH₃(CH₂)₂—S(=O)₂—NH— |
| 562 | CH₃C(=O)— | CH₃(CH₂)₃—S(=O)₂—NH— |
| 563 | CH₃C(=O)— | C₆H₅—S(=O)₂—NH— |
| 564 | CH₃C(=O)— | H₃C—C₆H₄—S(=O)₂—NH— |

TABLE 7-continued

[Structure shown: steroid-containing compound with R⁴O, OR⁴, R⁵, OCH₃ substituents and CON—H linkage]

| Compound | R⁴ | R⁵ |
|---|---|---|
| 565 | CH₃C(O)— | 3-methylphenyl-SO₂—NH— |
| 566 | CH₃C(O)— | 2-methylphenyl-SO₂—NH— |
| 567 | CH₃C(O)— | 4-ethylphenyl-SO₂—NH— |
| 568 | CH₃C(O)— | 4-(CH₃(CH₂)₂)phenyl-SO₂—NH— |
| 569 | CH₃C(O)— | 4-(CH₃(CH₂)₃)phenyl-SO₂—NH— |
| 570 | CH₃C(O)— | 4-Cl-phenyl-SO₂—NH— |
| 571 | CH₃C(O)— | 4-HO-phenyl-SO₂—NH— |
| 572 | CH₃C(O)— | 4-O₂N-phenyl-SO₂—NH— |
| 573 | CH₃C(O)— | 4-H₂N-phenyl-SO₂—NH— |
| 574 | CH₃C(O)— | 4-HOOC-phenyl-SO₂—NH— |

TABLE 7-continued

| Compound | R⁴ | R⁵ |
|---|---|---|
| 575 | CH₃C(=O)— | CH₃CO— |
| 576 | CH₃CH₂C(=O)— | CH₃CH₂CO— |
| 577 | C₆H₅−C(=O)− | C₆H₅−CO− |

TABLE 8

| Compound | R⁴ | R⁵ |
|---|---|---|
| 578 | H | HO— |
| 579 | CH₃C(=O)— | CH₃CO— |

The salts formed with the carboxyl groups of the compounds represented by the general formula (I) are preferably pharmaceutically acceptable salts and, for example, include salts with alkali metales such as sodium, potassium, etc. and salts with organic amines such as ammonia, tris (hydroxymethyl) aminomethane, N,N-bis (hydroxyethyl) piperazine, 2-amino-2-methyl-1-propanol, ethanolamine, N-methylglucamine, L-glucamine, etc.

The salts formed with the amino groups of the compounds represented by the general formula (I) are preferably pharmaceutically acceptable salts and, for example, include inorganic acid salts such as hydrochlorides, hydrobromides, hydroiodides, sulfates, phosphates and the like, and organic acid salts such as oxalates, maleates, fumarates, lactates, malates, citrates, tartrates, benzoates, methanesulfonates, camphorsulfonates and the like.

The compounds of the above-mentioned formula (I) and their salts may be present in the form of a hydrate or solvate, and therefore, these hydrates and solvates are also included in the scope of the present invention. Solvents which give the solvates include methanol, ethanol, isopropanol, acetone, ethyl acetate, methylene chloride and the like.

Further, the compounds of the above-mentioned formula (I) have one or more asymmetric carbon atoms, and many isomers can exist. These isomers are also included in the scope of the present invention.

The process for preparing compounds of the present invention is explained below.

The compounds of the present invention can be prepared according to the following methods.

1. The cases wherein R⁵ is $$\underset{CH_3CNH-}{\overset{O}{\underset{\|}{}}}.$$

(a) A process for preparing a compound wherein the 2-position of sialic acid is in the form of an α-isomer (i) The cases wherein X is oxygen:

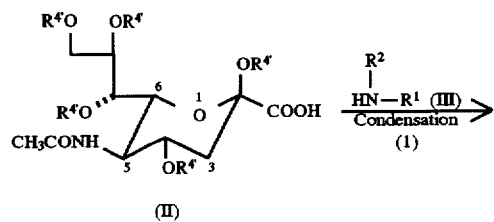

-continued

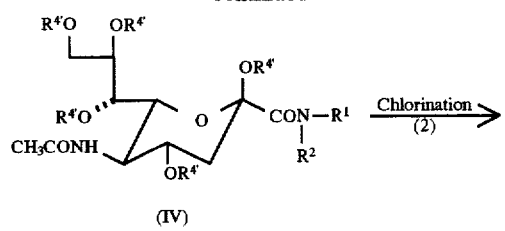
(IV)

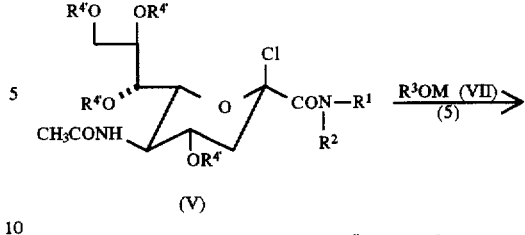
(V)

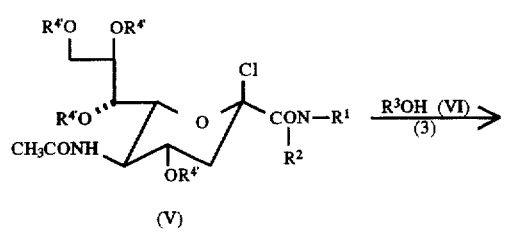
(V)

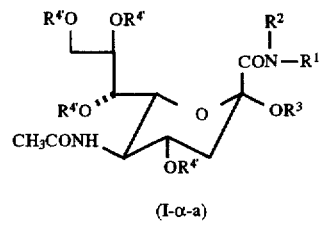
(I-α-a)

In the above reaction schema, $R^1$, $R^2$, $R^3$ and $R^{4'}$ are as previously defined and M represents an alkali metal or a quaternary ammonium ion.

Namely, compound (V) is allowed to reach with compound (VII) [process (5)] to produce compound (1-α-a).

Further, compound (1-α-a) can also be prepared according to the following reaction schema.

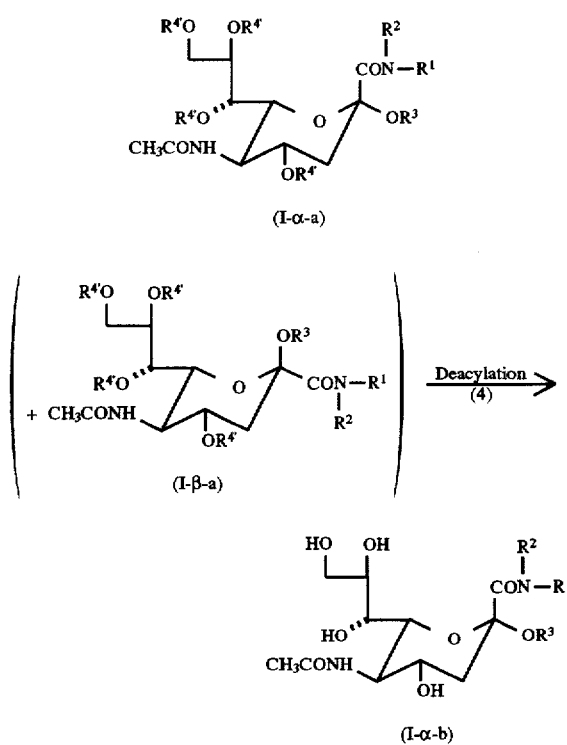

In the above reaction schema, $R^1$, $R^2$ and $R^3$ are as defined in the above-mentioned general formula (I) and $R^{4'}$ represents $C_2-C_7$ acyl.

The compound (II) is first allowed to react with compound (III) [process (1)] to give compound (IV), which is then chlorinated [process (2)] to give compound (V), which is then allowed to react with compound (VI) [process (3)] to give compound (1-α-a). The resulting compound (1-α-a) is deacylated by allowing to react with an alkoxide such as sodium methoxide, etc. [process (4)] to produce compound (1-α-b).

Further, compound (1-α-a) can also be prepared by the following reaction schema.

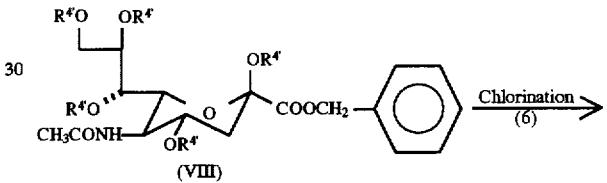
(VIII)

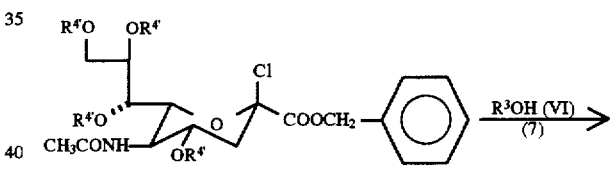
(IX)

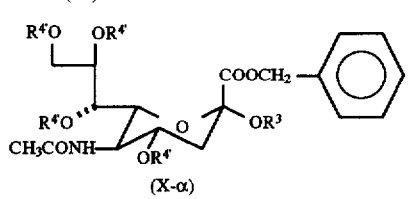
(X-α)

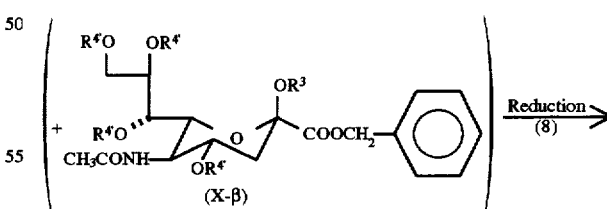
(X-β)

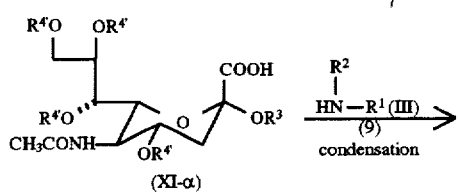
(XI-α)

-continued

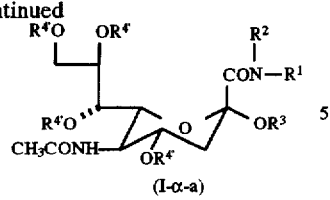

(I-α-a)

In the above reaction schema, $R^1$, $R^2$, $R^3$ and $R^{4'}$ are as previously defined.

The compound (VIII) is first chlorinated [process (6)] to give compound (IX), which is then allowed to react with compound (VI) [process (7)] to give compound (X-α). The resulting compound (X-α) is reduced [process (8)] to give compound (XI-α), which is then allowed to react with compound (III) [process (9)] to produce compound (I-α-a).

Process (1) is carried out as follows. Namely, compound (II) is allowed to react with 0.9 to 10 equivalents, preferably 1.0 to 5.0 equivalents, of chloroformate such as ethyl chloroformate, isobutyl chloroformate or the like is and 0.9 to 10 equivalents, preferably 1.0 to 5.0 equivalents, of a tertiary amine such as N-methylmorpholine, triethylamine or the like in a solvent such as tetrahydrofuran, dioxane, acetonitrile, dichloromethane, dichloroethane or the like at temperature of −50° C. to 50° C., preferably −20° C. to room temperature, to give corresponding mixed anhydride of compound (II). Then, the anhydride is allowed to react with 0.9 to 10 equivalents, preferably 1.0 to 5.0 equivalents, of compound (III) or its salt such as hydrochloride using the same equivalents of a tertiary amine at temperature of −50° C. to 50° C., preferably −20° C. to room temperature. Alternatively, compound (II) is allowed to react with 0.9 to 10 equivalents, preferably 1.0 to 5.0 equivalents, of chloride such as thionyl chloride, phosphorus pentachloride, phosphorus oxychloride or the like and 0.9 to 20 equivalents, preferably 1.0 to 10 equivalents, of base such as pyridine or the like in a solvent such as tetrahydrofuran, dioxane, acetonitrile, dichloromethane, dichloroethane or the like at temperature of −50° C. to 50° C., preferably −20° C. to room temperatures, to give corresponding acid chloride of compound (II). Then, the acid chloride is allowed to react with 0.9 to 10 equivalents, preferably 1.0 to 5.0 equivalents, of compound (III) or its salt such as hydrochloride, using 0.9 to 100 equivalents, preferably 1.0 to 50 equivalents, of a tertiary amine at temperature of −50° C. to 50° C., preferably −20° C. to room temperature. In this process it is more preferable that the reaction is carried out under anhydrous condition.

Process (2) is carried out at temperatures of −20° C. to 50° C., preferably 0° C. to room temperature, in an acid chloride such as acetyl chloride, propionyl chloride, butyl chloride, valeryl chloride, benzoyl chloride or the like. In this process, it is preferable that the reaction liquid is saturated with hydrochloric acid gas because it increases the yield. Further, the reaction is more preferably carried out under anhydrous condition.

Process (3) is conducted using 0.9 to 200 equivalents, preferably 1.0 to 100 equivalents, of compound (VI) in the presence of 0.1 to 10 equivalents, preferably 0.9 to 5.0 equivalents, of a silver catalyst such as silver trifluoromethanesulfonate, silver salicylate, silver carbonate, silver oxide or the like, in a solvent such as benzene, toluene, dichloromethane, dichloroethane or the like, at temperature of 0° C. to 50° C., preferably 0° C. to room temperature. In this process, the presence of 0.1 to 10 equivalents, preferably 0.9 to 5.0 equivalents, of a base such as 2,4,6-trimethylpyridine, pyridine or the like is preferable because of the increase of the yield. Further, the reaction is more preferably carried out under anhydrous condition.

Process (4) is conducted using 0.05 to 5.0 equivalents, preferably 0.1 to 2.0 equivalents, of an alkoxide in a solvent such as methanol or the like at temperature of 0° C. to 50° C., preferably 0° C. to room temperature. In this process, the reaction is more preferably carried out under anhydrous condition.

Process (5) is carried out using 0.9 to 200 equivalents, preferably 1.0 to 100 equivalents, of compound (VII) at temperature of 0° C. to 50° C. preferably 0° C. to room temperature in a solvent such as acetonitrile, tetrahydrofuran, dioxane, dimethylformamide, dimethyl sulfoxide or the like. In this process, the presence of a silver catalyst such as silver trifluoromethanesulfonate, silver salicylate, silver carbonate, silver oxide or the like is preferable because of the increase of the yield. Further, the reaction is more preferably carried out under anhydrous condition.

Process (6) is conducted under a similar condition to that in process (2).

Process (7) is carried out using 0.9 to 500 equivalents, preferably 1.0 to 200 equivalents, of compound (VI) in the presence of 0.1 to 10 equivalents, preferably 0.9 to 5.0 equivalents, of a silver catalyst such as silver trifluoromethanesulfonate, silver salicylate, silver carbonate, silver oxide or the like at temperature of 0° C. to 50° C., preferably 0° C. to room temperature, in a solvent such as benzene, toluene, dichloromethane, dichloroethane or the like or without a solvent. In this process, the presence of 0.1 to 10 equivalents, preferably 0.9 to 5.0 equivalents, of a base such as 2,4,6-trimethylpyridine, pyridine or the like is preferable because of the increase of the yield. Further, the reaction is more preferably performed under anhydrous condition.

Process (8) is conducted in the presence of 0.1 to 200% by weight, preferably 1.0 to 100%, by weight, of a catalyst such as palladium black, palladium carbon or the like in a solvent such as methanol, ethanol, tetrahydrofuran, dioxane or the like in an atmosphere of hydrogen at temperature of 0° C. to 50° C. preferably 0° C. to room temperature.

Process (9) is carried out under a similar condition to that in process (1).

ii) The cases wherein X is sulfur:

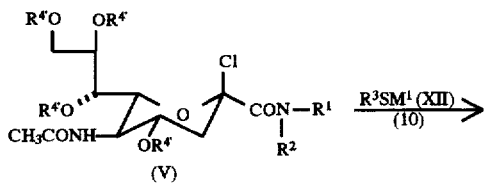

(V)

-continued

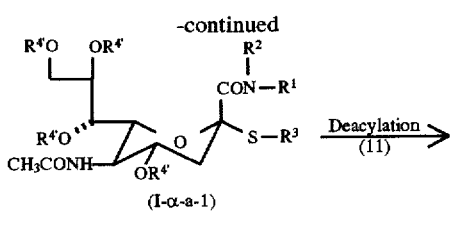
(I-α-a-1)

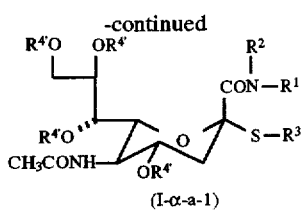
(I-α-a-1)

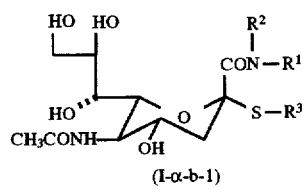
(I-α-b-1)

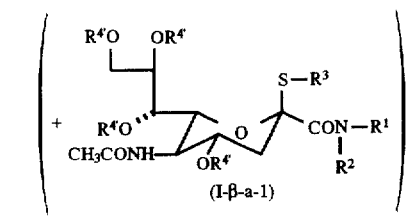
(I-β-a-1)

In the above reaction schema, $R^1$, $R^2$, $R^3$, $R^{4'}$ are as defined above and $M^1$ represents an alkali metal.

First, compound (V) is allowed to react with compound (XII) [process (10)] to produce compound (I-α-a-1), which is then deacylated by the reaction with an alkoxide such as sodium methoxide or the like [process (11)] to produce compound (1-α-b-1).

Compound (I-α-a-1) can also be made as described below.

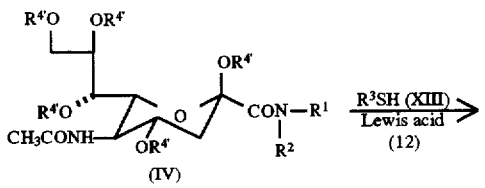
(IV)

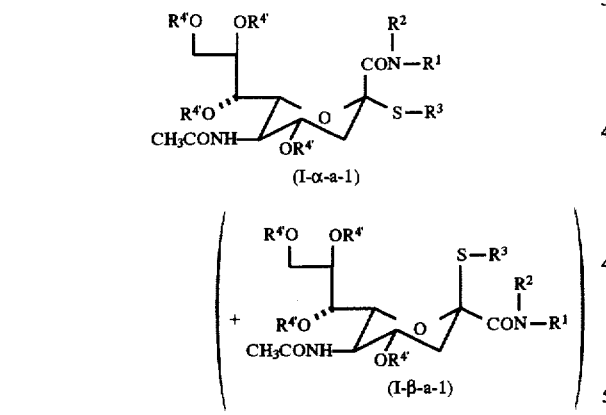
(I-α-a-1)

(I-β-a-1)

In the above reaction schema, $R^1$, $R^2$, $R^3$ and $R^{4'}$ are as defined above. Namely, compound (IV) is allowed to react with compound (XIII) in the presence of a Lewis acid catalyst [process (12)] to produce compound (1-α-a-1).

Further, compound (I-α-a-1) can also be made as described below.

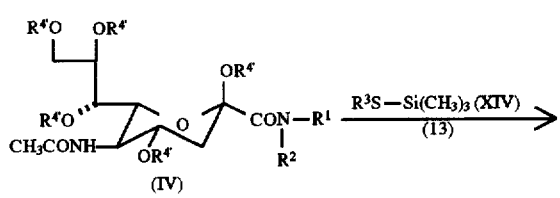
(IV)

In the above reaction schema, $R^1$, $R^2$, $R^3$ and $R^{4'}$ are as defined above.

Namely, compound (IV) is allowed to react with compound (XIV) [process (13)] to produce compound (I-α-a-1).

Process (10) is conducted using 0.9 to 200 equivalents, preferably 1.0 to 100 equivalents, of compound (XII) in a solvent such as acetonitrile, tetrahydrofuran, dioxane, dimethylformamide, dimethyl sulfoxide or the like at temperature of 0° C. to 50° C., preferably 0° C. to room temperature. In this process, the presence of 0.1 to 10 equivalents preferably 0.9 to 5.0 equivalents of a silver catalyst such as silver trifluoromethanesulfonate, silver salicylate, silver carbonate, silver oxide or the like is preferable because of the increase of the yield. Further, the reaction is more preferably carried out under anhydrous condition.

Process (11) is conducted under a similar condition to that in process (4).

Process (12) is performed using 0.9 to 10 equivalents, preferably 1.0 to 5.0 equivalents, of compound (XIII) in the presence of 0.9 to 10 equivalents, preferably 1.0 to 5.0 equivalents, of a Lewis acid catalyst such as $BF_3$, $ZnCl_2$, $AlCl_3$ or the like in a solvent such as dichloromethane, dichloroethane, dioxane, ethers or the like at temperature of 0° C. to 50° C., preferably 0° C. to room temperature. In this process, the reaction is more preferably conducted under anhydrous condition.

Process (13) is performed using 0.9 to 10 equivalents, preferably 1.0 to 5.0 equivalents, of compound (XIV) in the presence of 0.1 to 10 equivalents, preferably 1.0 to 5.0 equivalents, of a catalyst such as trimethylsilyl trifluoromethanesulfonate or the like at temperature of 0° C. to 50° C., preferably 0° C. to room temperature, in a solvent such as dichloromethane, dichloroethane, ethers or the like. In this process, the reaction is more preferably performed under anhydrous condition.

(b) Preparation of a compound wherein the 2-position of sialic acid is in the form of a β-isomer
  (i) The cases wherein X is oxygen

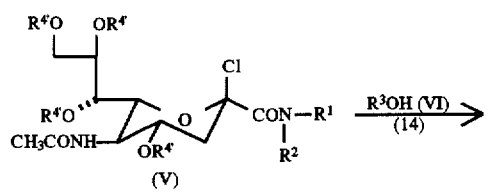
(V)

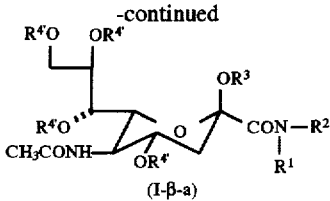
(I-β-a)

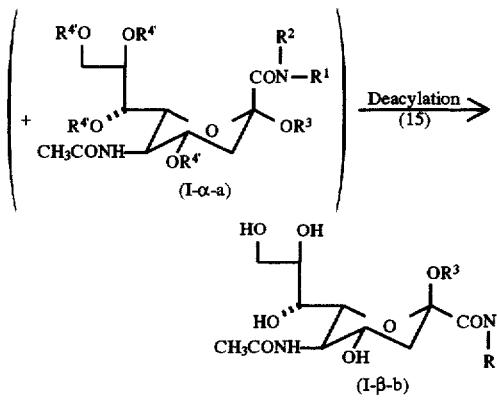
(I-α-a) Deacylation (15)

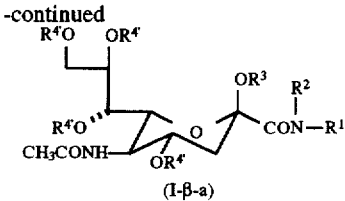
(I-β-a)

In the above reaction schema, $R^1$, $R^2$, $R^3$ and $R^{4'}$ are as defined above.

The compound (IX) is first allowed to react with compound (VI) [process (16)] to produce compound (X-β), which is then reduced [process (17)] to produce compound (XI-β), which is then allowed to react with compound (III) [process (18)] to produce compound (I-β-a).

Further, compound (X-β) can also be prepared as described below.

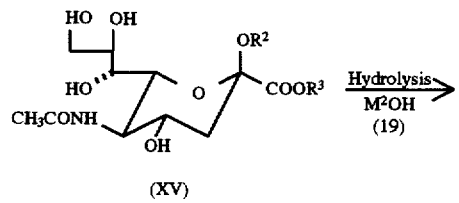
(XV) Hydrolysis / M²OH (19)

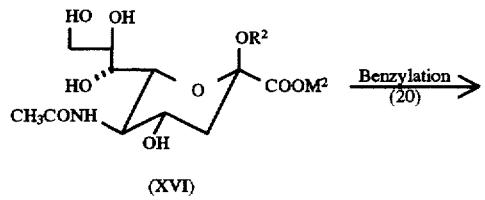
(XVI) Benzylation (20)

(I-β-b)

In the above reaction schema, $R^1$, $R^2$, $R^3$ and $R^{4'}$ are as defined above.

The compound (V) is first allowed to react with compound (VI) [process (14)] to produce compound (I-β-a), which is then deacylated by the reaction with an alkoxide such as sodium methoxide or the like [process (15)] to produce compound (I-β-b)

Further, compound (I-β-a) can also be prepared as described below.

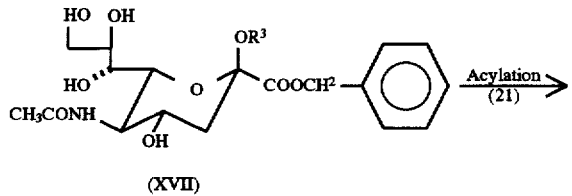
(XVII) Acylation (21)

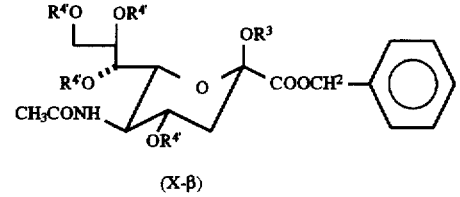
(X-β)

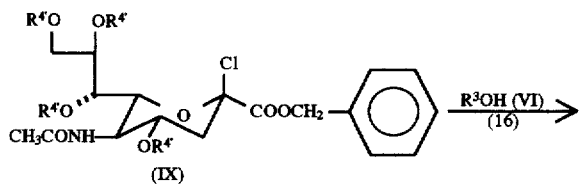
(IX) R³OH (VI) (16)

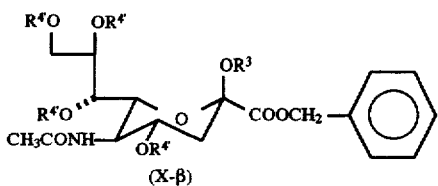
(X-β)

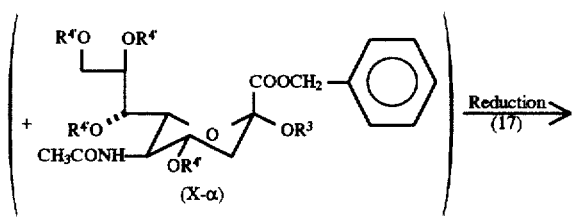
(X-α) Reduction (17)

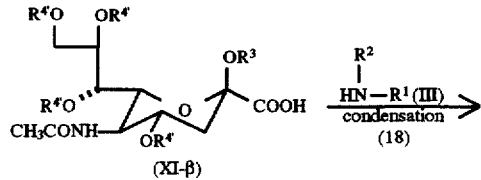
(XI-β) HN—R¹(III) condensation (18)

In the above reaction schema, $R^3$ and $R^{4'}$ are as defined above and $M^2$ represents an alkali metal.

The compound (XV) is first hydrolyzed by the reaction with an alkali such as sodium hydroxide or the like [process (19)] to produce compound (XVI). The resulting compound (XVI) is then allowed to react with benzylbromide or the like [process (20] to produce compound (XVII), which is acylated [process (21)] to produce compound (X-β).

Process (14) is conducted under the condition similar to that of process (3).

Process (15) is performed under the condition similar to that of process (4).

Process (16) is conducted under the condition similar to that of process (3).

Process (17) is performed under the condition similar to that of process (8).

Process (18) is performed under the condition similar to that of process (1).

Process (19) is conducted using 0.9 to 10 equivalents, preferably 1.0 to 5.0 equivalents, of a base such as sodium hydroxide, potassium hydroxide or the like in a solvent such as water, methanol, ethanol or the like at temperatures of 0° C. to 50° C., preferably 0° C. to room temperature.

Process (20) is conducted using 0.9 to 10 equivalents, preferably 1.0 to 5.0 equivalents, of benzyl chloride, benzyl bromide or the like in a solvent such as dimethylformamide, tetrahydrofuran or the like at temperatures of 0° C. to 50° C., preferably 0° C. to room temperature. In this process, the reaction is more preferably performed under anhydrous condition.

Process (21) is carried out using 4.0 to 200 equivalents, preferably 4.4 to 100 equivalents, of an acid anhydride such as acetic anhydride or an acid chloride such as acetyl chloride, propionyl chloride, butyryl chloride, valeryl chloride, benzoyl chloride or the like in a solvent such as pyridine or the like at temperature of 0° C. to 80° C., preferably 0° C. to 50° C. In this process, the presence of 0.1 to 1 equivalents, preferably 0.1 to 0.5 equivalents, of a base such as 4-dimethylaminopyridine, etc. is preferable because of the increase of the yield, and the reaction is more preferably carried out under anhydrous condition.

ii) the cases wherein X is sulfur

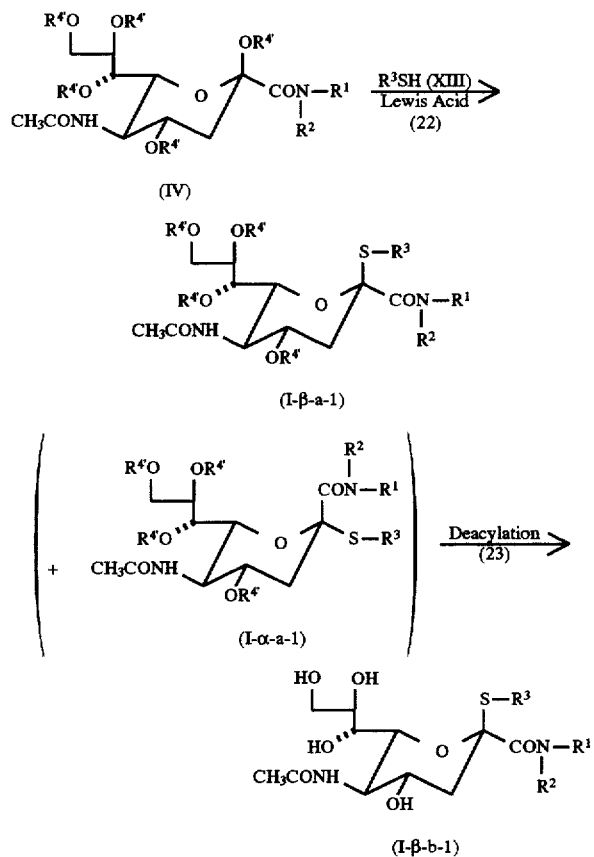

In the above reaction schema, $R^1$, $R^2$, $R^3$ and $R^{4'}$ are as defined above.

The compound (IV) is first allowed to react with compound (XIII) in the presence of a Lewis acid catalyst [process (22)] to produce compound (I-β-a-1), which is then deacylated by the reaction with an alkoxide such as sodium methoxide [process (23)] to produce compound (I-β-b-1).

Process (22) is carried out under the condition similar to that of process (12).

Process (23) is carried out under the condition similar to that of process (4).

2. The cases wherein $R^5$ is $R^{15}NH—$ wherein $R^{15}$ is as defined in the above formula (I) except the case wherein $R^{15}$ is $CH_3CO—$.

(a) A process for preparing the compound wherein the 2-position of sialic acid is in the form of an α-isomer (i) The cases wherein X is oxygen

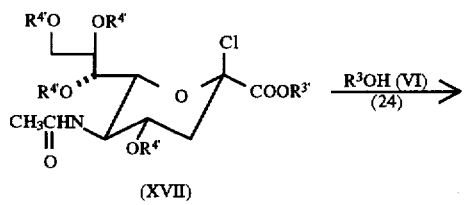

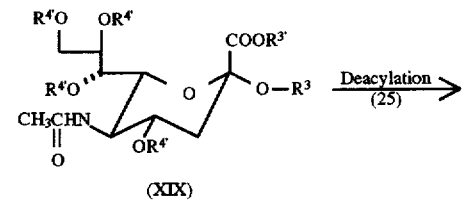

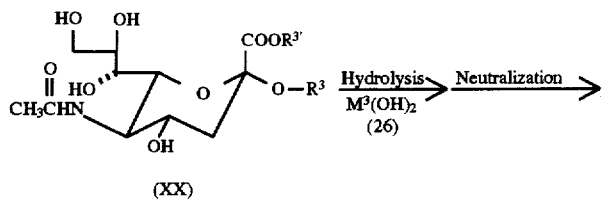

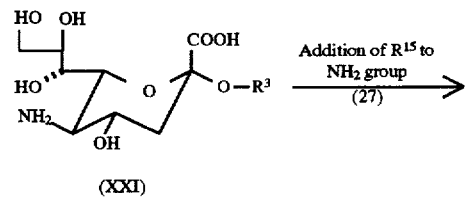

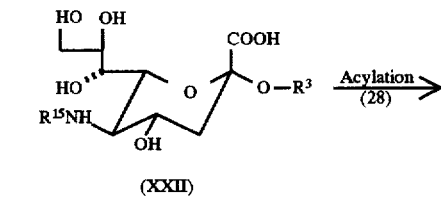

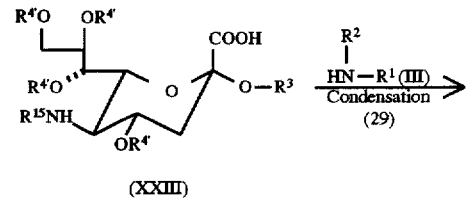

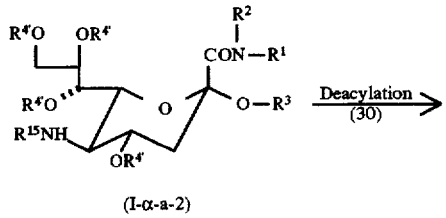

(I-α-a-2)

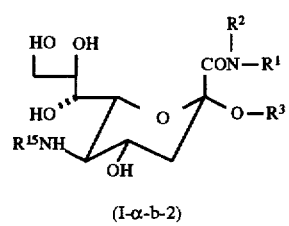

(I-α-b-2)

In the above reaction schema, $R^1$, $R^2$, $R^3$, $R^{4'}$ and $R^{15}$ are as defined above, $R^{3'}$ represents $C_1$-$C_6$ alkyl, and $M^3$ represents an alkaline earth metal.

The compound (XVIII) is first allowed to react with compound (VI) [process (24)] to produce compound (XIX), which is then deacylated by the reaction with an alkoxide such as sodium methoxide or the like [process (25)] to produce compound (XX). The compound (XX) is then hydrolyzed by the reaction with an alkali such as barium hydroxide or the like [process (26)] to produce compound (XXI), which is then N-acylated, N-oxycarbonylated or N-sulfonylated [process (27)] to produce compound (XXII). The compound (XXII) is then acylated [process (28)] to produce compound (XXIII), which is then allowed to react with compound (III) [process (29)] to produce compound (I-α-a-2). Then, the compound (I-α-a-2) is deacylated by the reaction with an alkoxide such as sodium methoxide or the like [process (30)] to produce compound (I-α-b-2).

Further, compound (I-α-a-2') can also be prepared by substituting the amine residue of 15-position of compound (I-α-a-2) with other amine residue as described below.

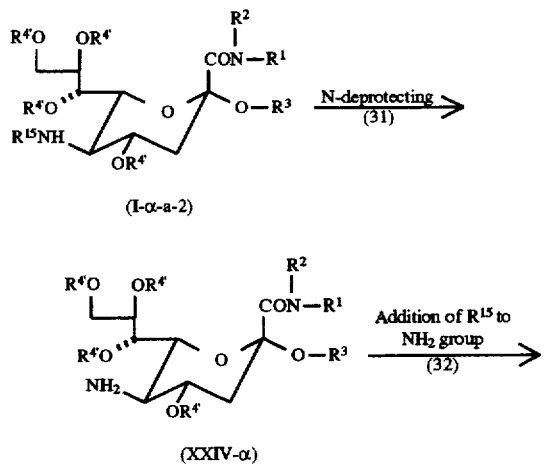

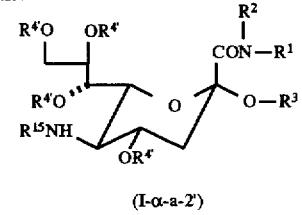

(I-α-a-2')

In the above reaction schema, $R^1$, $R^2$, $R^3$, $R^{4'}$ and $R^{15}$ are as defined above, but $R^{15}$ in compound (I-α-a-2) and $R^{15}$ in compound (I-α-a-2') are not the same.

The compound (I-α-a-2) is first N-deblocked [process (31)] to produce compound (XXIV-α), which is then N-acylated, N-oxycarbonylated or N-sulfonylated [process (32)] to produce compound (I-α-a-2').

Process (24) is conducted under the condition similar to that of process (7).

Process (25) is performed under the condition similar to that of process (4).

Process (26) is carried out using 0.9 to 10 equivalents, preferably 1.0 to 5.0 equivalents, of a base such as barium hydroxide or the like in a solvent such as water, methanol, ethanol or the like at temperatures of 0° C. to 100° C., preferably 50° C. to 100° C.

In process (27), N-acylation is carried out using 0.9 to 10 equivalents, preferably 1.0 to 3.0 equivalents, of an acid anhydride such as acetic anhydride, propionic anhydride or the like or an acid chloride such as acetyl chloride, propionyl chloride, benzoyl chloride or the like and 0.9 to 10 equivalents, preferably 1.0 to 3.0 equivalents, of a tertiary amine such as triethylamine or the like in a solvent such as water, methanol, ethanol, dioxane, tetrahydrofuran or the like; or N-oxycarbonylation is carried out using 0.9 to 10 equivalents, preferably 1.0 to 3.0 equivalents, of di-t-butyldicarbonate, carbobenzoxy chloride or the like and 0.9 to 10 equivalents, preferably 1.0 to 3.0 equivalents, of a tertiary amine such as triethylamine or the like; or N-sulfonylation is conducted using 0.9 to 10 equivalents, preferably 1.0 to 3.0 equivalents, of methanesulfonyl chloride, benzenesulfonyl chloride or the like and 0.9 to 10 equivalents, preferably 1.0 to 3.0 equivalents, of a tertiary amine such as triethylamine or the like. In this process, the reactions are carried out at temperatures of 0° C. to 80° C., preferably 0° C. to 50° C.

Process (28) is performed under the condition similar to that of process (21).

Process (29) is performed under the condition similar to that of process (1).

Process (30) is performed under the condition similar to that of process (4).

In process (31), N-deprotecting is carried out in the presence of 0.1 to 200% by weight, preferably 1.0 to 100% by weight, of a catalyst such as palladium black, palladium carbon or the like in a solvent such as methanol, ethanol, tetrahydrofuran, dioxane or the like in an atmosphere of hydrogen at temperature of 0° C. to 50° C., preferably 0° C. to room temperature; or N-deprotecting is carried out using 0.9 to 100 equivalents, preferably 1.0 to 20 equivalents, of hydrogen chloride, hydrogen bromide or the like in a solvent such as dioxane, ethyl acetate, acetic acid or the like at temperature of 0° C. to 50° C., preferably 0° C. to room temperature.

In process (32), N-acylation is performed using 0.9 to 10 equivalents, preferably 1.0 to 3.0 equivalents, of an acid anhydride such as acetic anhydride, propionic anhydride or the like or an acid chloride such as acetyl chloride, propionyl chloride, benzoyl chloride or the like, and 0.9 to 10 equivalents, preferably 1.0 to 3.0 equivalents, of a tertiary amine such as triethylamine or the like; or N-oxycarbonylation is carried out using 0.9 to 10 equivalents, preferably 1.0 to 3.0 equivalents, of di-t-butyldicarbonate, carbobenzoxy chloride or the like and 0.9 to 10 equivalents, preferably 1.0 to 3.0 equivalents, of a tertiary amine such as triethylamine or the like; or N-sulfonylations is performed using 0.9 to 10 equivalents, preferably 1.0 to 3.0 equivalents, of methanesulfonyl chloride, benzenesulfonyl chloride or the like and 0.9 to 10 equivalents, preferably 1.0 to 3.0 equivalents, of a tertiary amine such as triethylamine or the like. The reactions in this process are carried out at temperature of 0° C. to 80° C., preferably 0° C. to 50° C. The reaction is more preferably carried out under anhydrous condition.

(ii) The cases wherein X is sulfur

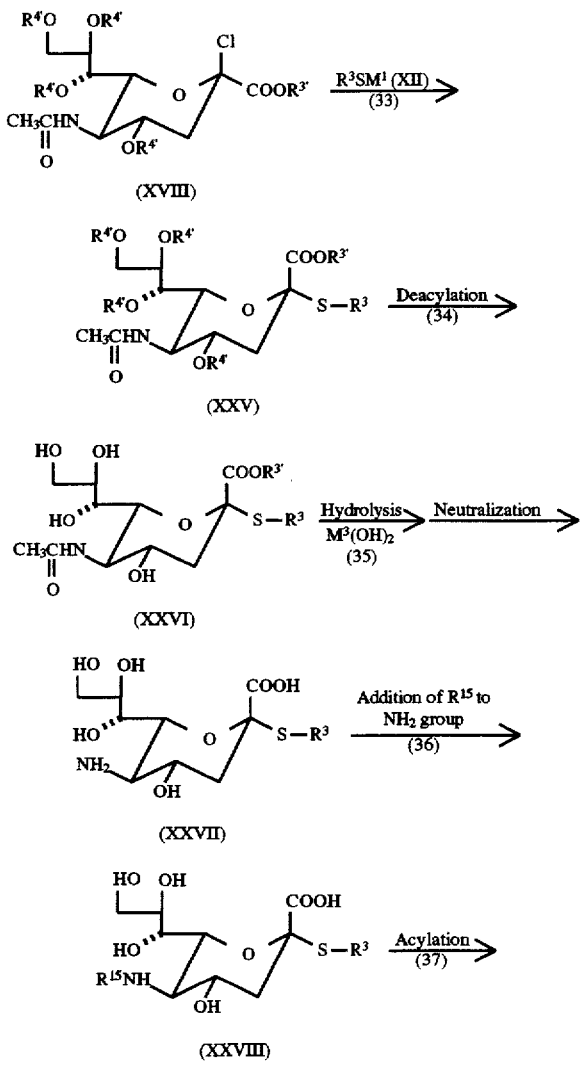

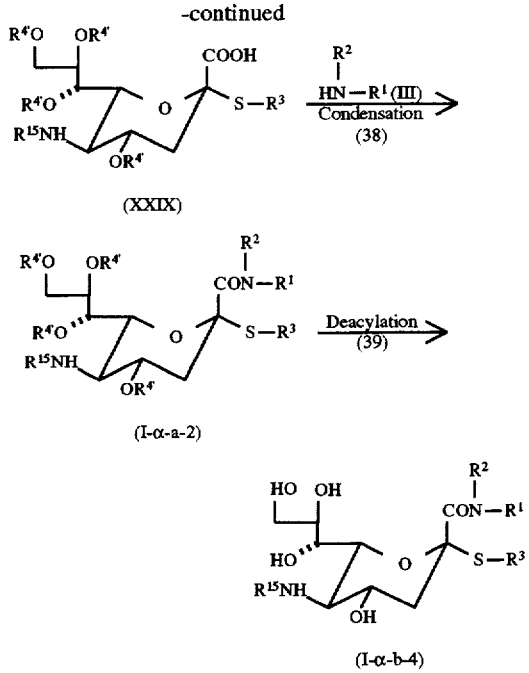

In the above reaction schema, $R^1$, $R^2$, $R^3$, $R^{3'}$, $R^{4'}$, $R^{15}$, $M^1$ and $M^3$ are as defined above.

The compound (XVIII) is first allowed to react with compound (XII) [process (33)] to produce compound (XXV), which is then deacylated by the reaction with an alkoxide such as sodium methoxide or the like [process (34)] to produce compound (XXVI). The compound (XXVI) is then hydrolyzed by the reaction with an alkali such as barium hydroxide or the like [process (35)] to produce compound (XXVII), which is then N-acylated, N-oxycarbonylated or N-sulfonylated [process (36)] to produce compound (XXVIII). The compound (XXVIII) is then acylated [process (37)] to produce compound (XXIX), which is then allowed to react with compound (III) [process (38)] to produce compound (I-α-a-4). The compound (I-α-a-4) is then deacylated by the reaction with an alkoxide such as sodium methoxide or the like [process (39)] to produce compound (I-α-b-4).

Process (33) is conducted under the condition similar to that of process (10).

Process (34) is conducted under the conditions similar to that of process (4).

Proceed (35) is conducted under the condition similar to that of process (26).

Process (36) is conducted under the condition similar to that of process (27).

Process (37) is conducted under the condition similar to that of process (21).

Process (38) is conducted under the condition similar to that of process (1).

Process (39) is conducted under the condition similar to that of process (4).

(b) A process for preparing a compound wherein the 2-position of sialic acid is in the form of a β-isomer (i) The cases wherein X is oxygen

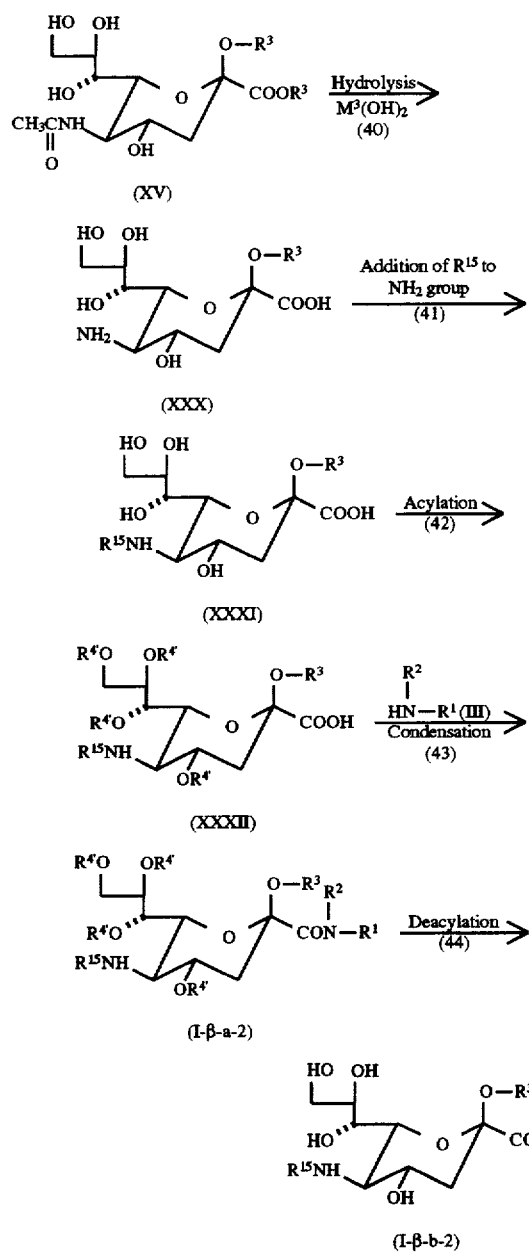

In the above reaction scheme, $R^1$, $R^2$, $R^3$, $R^{4'}$, $R^{15}$ and $M^3$ are as defined above.

The compound (XV) is first hydrolyzed by the reaction with an alkali such as barium hydroxide or the like [process (40)] to produce compound (XXX), which is then N-acylated, N-oxycarbonylated or N-sulfonylated [process (41)] to produce compound (XXXI). The compound (XXXI) is then acylated [process 42)] to produce compound (XXXII), which is then allowed to react with compound (III) [process (43)] to produce compound (I-β-a-2). The compound (1-β-a-2) is then deacylate by the reaction with an alkoxide such as sodium methoxide or the like [process (44)] to produce compound (I-β-b-2).

Process (40) is conducted under the condition similar to that of process (26).

Process (41) is conducted under the condition similar to that of process (27).

Process (42) is conducted under the condition similar to that of process (21).

Process (43) is conducted under the condition similar to that of process (1).

Process (44) is conducted under the condition similar to that of process (4).

(ii) The cases wherein X is sulfur

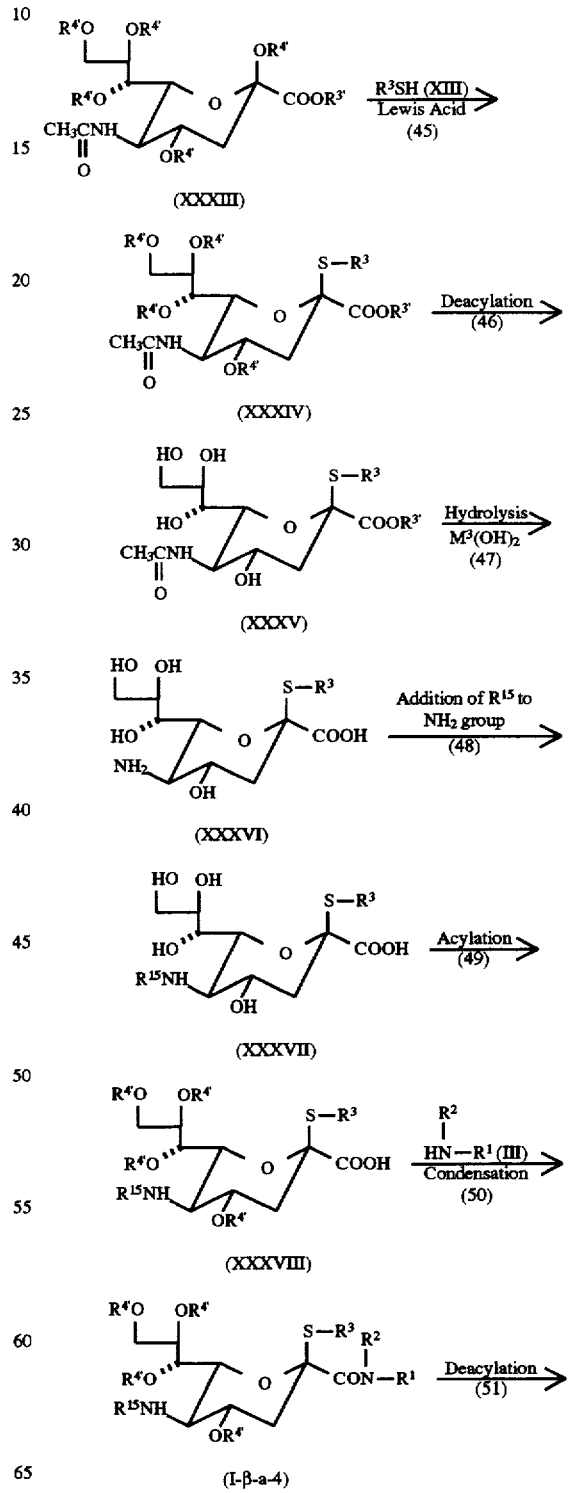

-continued

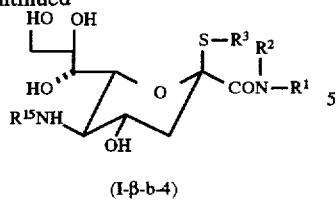

(I-β-b-4)

In the above reaction scheme, $R^1$, $R^2$, $R^3$, $R^{3'}$, $R^{4'}$, $R^{15}$ and $M^3$ are as defined above.

The compound (XXXIII) is first allowed to react with compound (XIII) [process (45)] to produce compound (XXXIV), which is then deacylated by the reaction with an alkoxide such as sodium methoxide or the like (process (46)] to produce compound (XXXV). The compound (XXXV) in then hydrolyzed by the reaction with an alkali such as barium hydroxide or the like [process (47)] to produce compound (XXXVI), which is then N-acylated, N-oxycarbonylated or N-sulfonylated [process (48)] to produce compound (XXXVII). The compound (XXXVII) is then acylated [process (49)] to produce compound (XXXVIII), which is then allowed to react with compound (III) [process (50)] to produce compound (I-β-a-4). The compound (I-β-a-4) is then deacylated by the reaction with an alkoxide such as sodium methoxide or the like [process (51)] to produce compound (I-β-b-4).

Process (45) is carried out under the condition similar to that of process (12).

Process (46) is carried out under the condition similar to that of process (4).

Process (47) is carried out under the condition similar to that of process (26).

Process (48) is carried out under the condition similar to that of process (27).

Process (49) is carried out under the condition similar to that of process (21).

Process (50) is carried out under the condition similar to that of process (1).

Process (50) is carried out under the condition similar to that of process (1).

Process (51) is carried out under the condition similar to that of process (4).

3. The cases wherein $R^5$ is $R^{14}O-$ wherein $R^{14}$ is as defined in the above formula (I)

(a) A process for preparing a compound wherein the 2-position of sialic acid is in the form of an α-isomer (i) The cases wherein X is oxygen

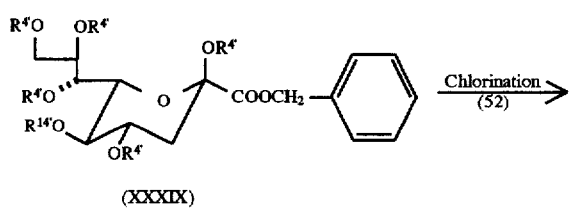

(XXXIX)

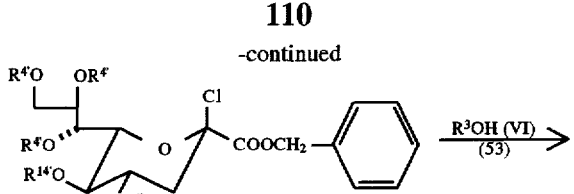

(XL)

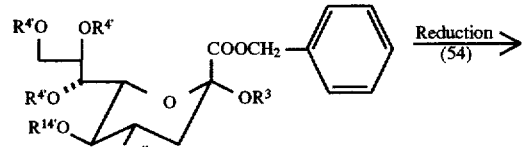

(XLI-α)

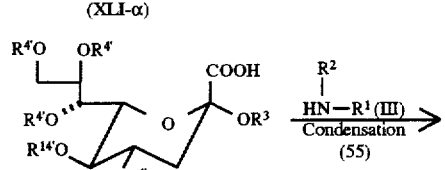

(XLII-α)

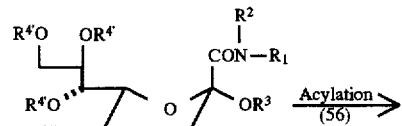

(I-α-a-5)

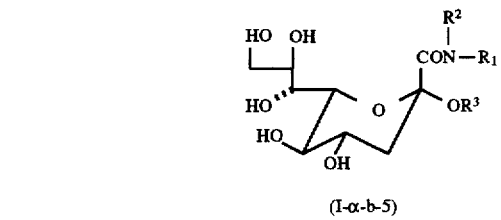

(I-α-b-5)

In the above reaction schema, $R^1$, $R^2$, $R^3$ and $R^{4'}$ as defined above and $R^{14'}$ represents $C_2$–$C_7$ acyl.

The compound (XXXIX) is first chlorinated [process (52)] to produce compound (XL), which is then allowed to react with compound (VI) [process 53] to produce compound (XLI-α). The compound (XLI-α) is then reduced [process (54)] to produce compound (XLII-α), which is then allowed to react with compound (III) [process (55)] to produce compound (I-α-a-5). The compound (I-α-a-5) is then deacylated by the reaction with an alkoxide such as sodium methoxide or the like [process 56] to produce compound (I-α-b-5).

Further, compound (I-α-a-5) can also be prepared according to the following reaction schema.

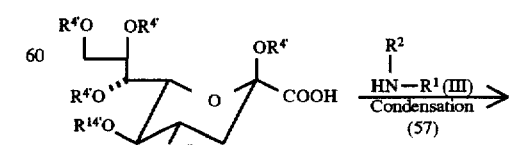

(XLIII)

111

-continued

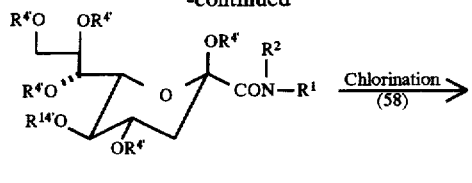

(XLIV)

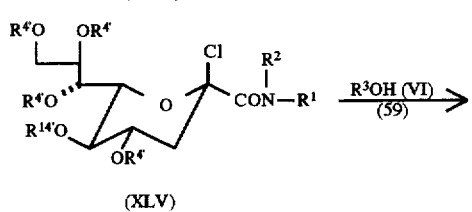

(XLV)

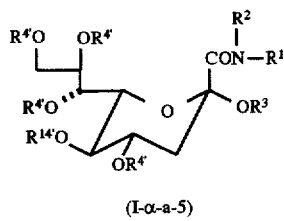

(I-α-a-5)

In the above reaction schema, $R^1$, $R^2$, $R^3$, $R^{4'}$ and $R^{14'}$ are as defined above.

The compound (XLIII) is first allowed to react with compound (III) [process (57)] to produce compound (XLIV), which is then chlorinated [process (58)] to produce compound (XLV). The compound (XLV) is then allowed to react with compound (VI) [process (59)] to produce compound (I-α-a-5).

Process (52) is conducted under the condition similar to that of process (2).

Process (53) is conducted under the condition similar to that of process (3).

Process (54) is conducted under the condition similar to that of process (8).

Process (55) is conducted under the condition similar to that of process (1).

Process (56) is conducted under the condition similar to that of process (4).

Process (57) is conducted under the condition similar to that of process (1).

Process (58) is conducted under the condition similar to that of process (2).

Process (59) is conducted under the condition similar to that of process (3).

(ii) The cases wherein X is sulfur

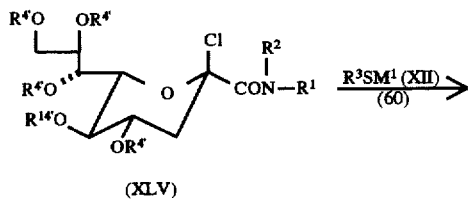

(XLV)

112

-continued

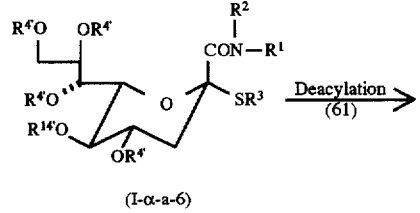

(I-α-a-6)

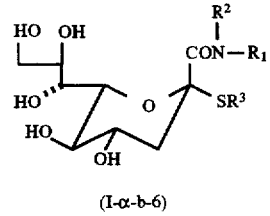

(I-α-b-6)

In the above reaction schema, $R^1$, $R^2$, $R^3$, $R^{4'}$, $R^{14'}$ and M1 are as defined above.

The compound (XLV) is first allowed to react with compound (XII) [process (60)] to produce compound (I-α-a-6). The compound (I-α-a-6) is then deacylated by the reaction with an alkoxide such as sodium methoxide, etc. [process (61)] to produce compound (I-α-b-6).

Further, compound (I-α-a-6) can also be prepared according to the following reaction schema.

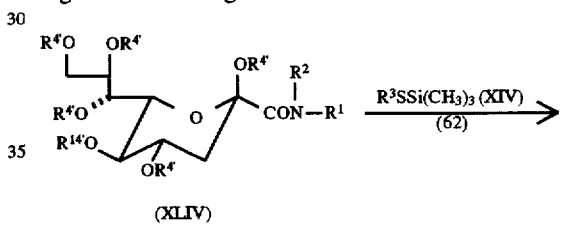

(XLIV)

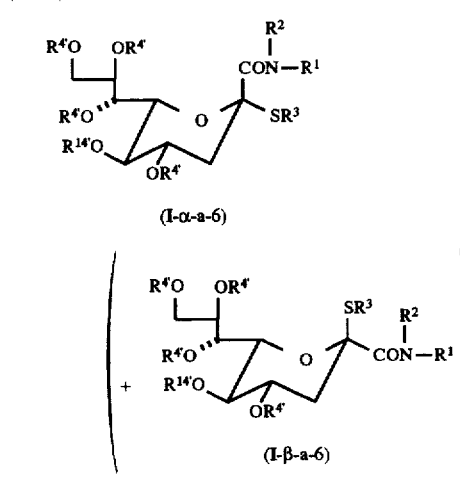

In the above schema, $R^1$, $R^2$, $R^3$, $R^{4'}$ and $R^{14'}$ are as defined above.

The compound (XLIV) is allowed to react with compound (XIV) [process (61)] to produce compound (I-α-a-6).

Further, compound (I-α-a-6) can also be prepared according to the following reaction schema.

113

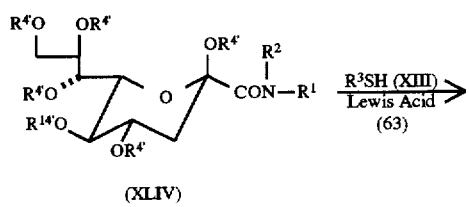

(XLIV)

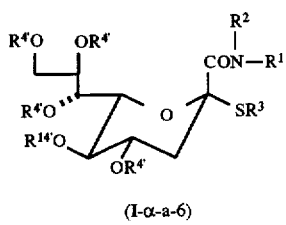

(I-α-a-6)

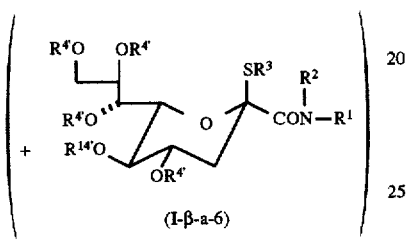

(I-β-a-6)

In the above schema, $R^1$, $R^2$, $R^3$, $R^{4'}$ and $R^{14'}$ are as defined above.

The compound (XLIV) is allowed to react with compound (XIII) in the presence of a Lewis acid catalyst [process (63)] to produce compound (I-α-a-6).

Process (60) is conducted under the condition similar to that of process (10).

Process (61) is conducted under the condition similar to that of process (4).

Process (62) is conducted under the condition similar to that of process (13).

Process (63) is conducted under the condition similar to that of process (12).

(b) A process for preparing a compound wherein the 2-position of sialic acid is in the form of a β-isomer (i) The cases wherein X is oxygen

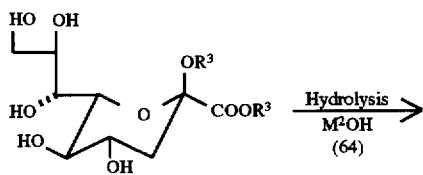

(XLVI)

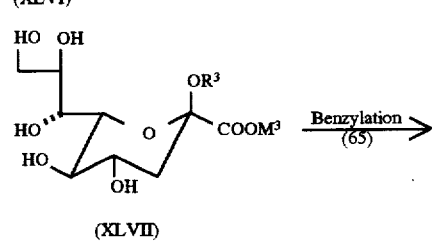

(XLVII)

114
-continued

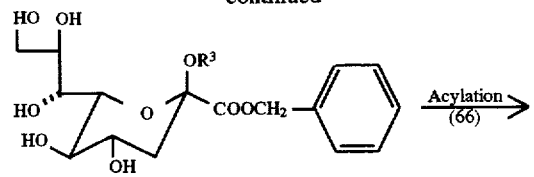

(XLVIII)

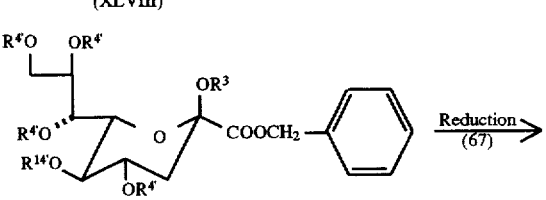

(XLI-β)

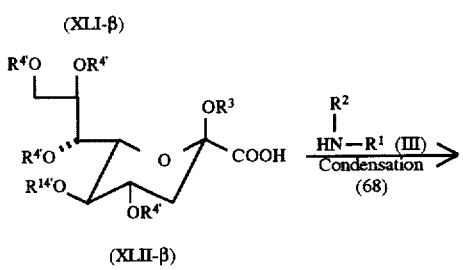

(XLII-β)

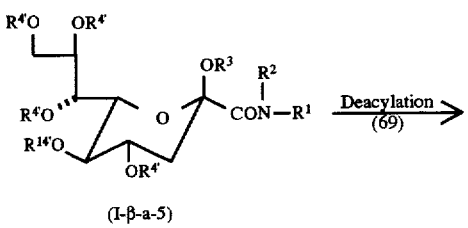

(I-β-a-5)

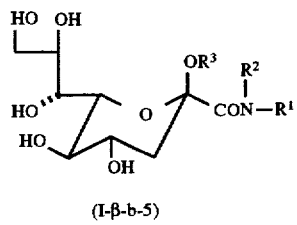

(I-β-b-5)

In the above reaction schema, $R^1$, $R^2$, $R^3$, $R^{4'}$, $R^{14'}$ and $M^2$ are as defined above.

The compound (XLVI) is first hydrolyzed by the reaction with an alkali such as sodium hydroxide [process (64)] to produce compound (XLVII), which is then allowed to react with benzyl bromide, etc. [process (65)] to produce compound (XLVIII). The compound (XLVIII) is then acylated [process (66)] to produce compound (XLI-β), which is then reduced [process (67)] to produce compound (XLII-β). The compound (XLII-β) is then allowed to react with compound III [process (68)] to produce compound (I-β-a-5), which is then deacylated by the reaction with an alkoxide such as sodium methoxide [process (69)] to produce compound (I-β-b-5).

Process (64) is conducted under the condition similar to that of process (19).

Process (65) is conducted under the condition similar to that of process (20).

Process (66) is conducted under the condition similar to that of process (21).

Process (67) is conducted under the condition similar to that of process (8).

Process (68) is conducted under the condition similar to that of process (1).

Process (69) is conducted under the condition similar to that of process (4).

(ii) The cases wherein X is sulfur

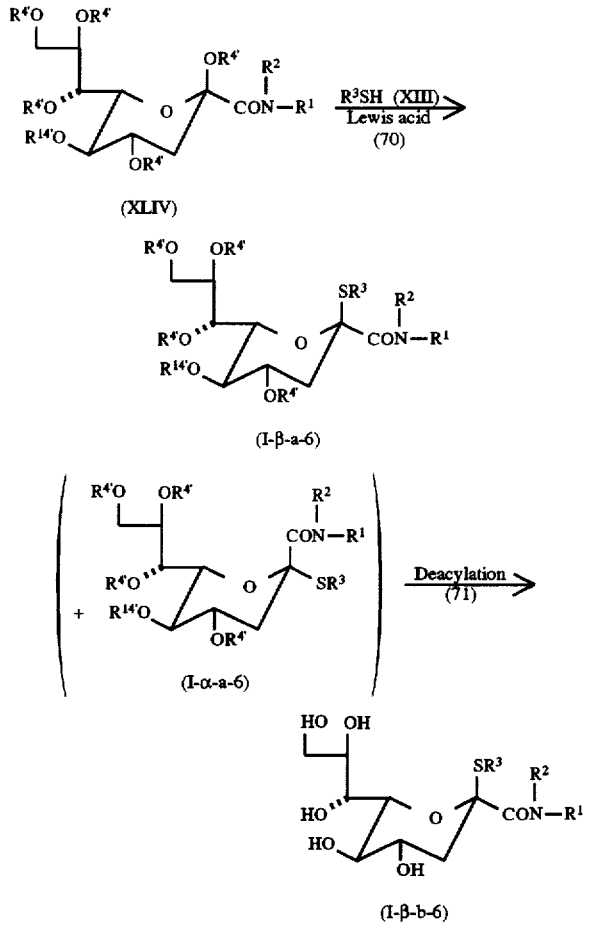

In the above reaction schema, $R^1$, $R^2$, $R^3$, $R^{4'}$ and $R^{14'}$ are as defined above.

The compound (XLIV) is first allowed to react with compound (XIII) in the presence of a Lewis-acid catalyst [process (70)] to produce compound (I-β-a-6), which is then deacylated by the reaction with an alkoxide such as sodium methoxide or the like [process (71)] to produce compound (I-β-b-6).

Process (70) is conducted under the condition similar to that of process (12).

Process (71) is conducted under the condition similar to that of process (4).

If an ester group is present in $R^3$, a carboxylic-acid derivative is produced by hydrolysis. Further, if a benzyl ether group is present in $R^3$ or $R^5$, a hydroxy derivative is produced by reduction. If a benzyloxycarbonylamino group is present in $R^3$, an amino derivative is produced by reduction. Further, the amino derivative is acylated to produce an acylamino derivative, or sulfonylated to produce a sulfonylamino derivative.

The isolation and purification of the compounds formed by the methods described in detail in the above sections 1, 2 and 3 can easily be performed by methods which are known and conventionally used, for example extraction, recrystallization, chromatography or the like.

Compounds of formulas (II), (III), (VIII), (XV), (XVIII), (XXXIII), (XXXIX), (XLIII) and (XLVI) which are starting materials in the present invention can be synthesized by methods described in the following published literatures.

Thus, compounds of formulas (II), (VIII), (XV), (XVIII), (XXXIII), (XXXIX), (XLIII) and (XLVI) can be synthesized by methods described in the following literatures.

(a) Carbohydr. Res., 125, 47–64 (1984).

(b) Chem. Pharm. Bull., 35, 3609–3614 (1987).

(c) Chem. Ber., 99, 611–617 (1966).

(d) Chem. Pharm. Bull., 36, 4807–4813 (1988).

Compound (III) can easily be synthesized by methods described in (e) J. Org. Chem., 27, 2925–2927 (1962).

Any methods similar to those described in the above literatures can also be used for the preparation of the starting materials.

The compounds of the present invention, when used as therapeutic drugs, are administered alone or together with pharmaceutically acceptable carriers. The composition of the therapeutic drugs is determined by solubility and chemical properties of the compounds, route of administration, dosage, schedules and the like. For example they may be orally administered in dosage forms of granules, fine subtilaes, powder, tablets, hard medicated syrups, soft capsules, medicated syrups, emulsions, suspensions, liposomes and solutions, and may be administered as injections intravenously, intramuscularly or subcutaneously.

They may be used as powders for injection which are dispensed when used. Organic or inorganic and pharmaceutically acceptable carriers in the form of liquid or solid which are suitable for oral, enteral, parenteral or topical administration can also be used together with the compounds of the present invention. Excipients for solid preparations include, for example, lactose, sucrose, starch, talc, cellulose, dextrin, kaolin, calcium carbonate, etc. The liquid preparations for oral administration, such as emulsions, syrups, suspensions, solutions and the like, contain inert diluents generally used, for example, water, vegetable oils or the like. Such preparations may contain adjuvants, for example, wetting agents, suspending agents, sweeteners, aromatics, coloring agents, preservatives and the like as well as inert diluents. A dispensed liquid preparation may be encapsuled in an absorbable substance such as gelatin, etc. Solvents or suspending agent used for preparing preparations for parenteral administration, namely injections, include, for example, water, propylene glycol, polyethylene glycol, benzyl alcohol, ethyl oleate, lecithin and the like. The dispensing of the preparations can be carried out by conventional methods.

Compounds of the present invention, when orally administered, are generally administered in a clinical dose of 1–1000 mg/day, preferably 1–200 mg/day, for an adult. More preferably, the dosage is appropriately increased or decreased depending on age, symptoms, or signs of diseases, and whether or not other drugs are simultaneously administered. The compounds of the present invention may be administered once a day, or twice or thrice a day with suitable intervals, or may intermitently be administered. The compounds of the present invention, when used for injections, are administered in a dosage for an adult of 0.1–100 mg a day, preferably 0.1–50 mg a day.

117

Figure 2:
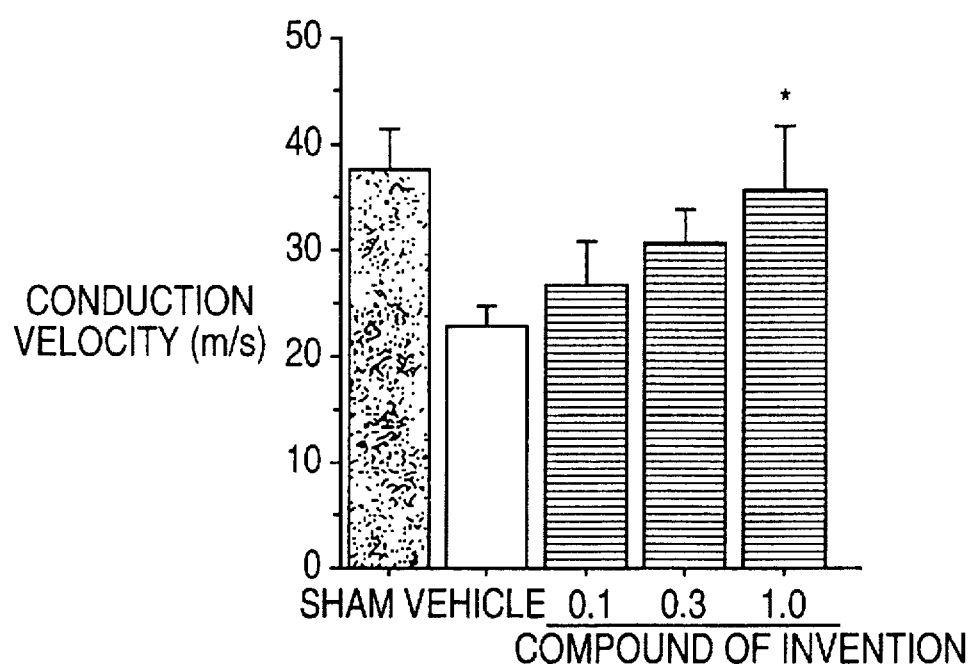

FIG. 2 shows the effect of the compound synthesized by the process shown in Example 3 on the sensory nerve conduction velocity in model rates having diabetes.

EXAMPLES

The present invention is illustrated by the following examples, but the present invention is not limited to these examples. The α-isomers and β-isomers in the examples represent isomers at the 3-position of the steroid compounds.

Synthetic Example 1

Synthesis of 3α-[N-(5-acetamido-2,4,7,8,9-penta-O-acetyl-3,5-dideoxy-β-D-glycero-D-galacto-2-nonulopyranosonyl) amino] cholestane [compound (IV) wherein $R^1$ is 3α-cholestane; $R^2$ is hydrogen; and $R^{4'}$ is acetyl].

To a solution of 5-acetamido-2,4,7,8,9-penta-O-acetyl-3,5-dideoxy-β-D-glycero-D-galacto- 2-nonulopyranosonic acid (5.5 g, 11.5 mmol) in dried tetrahydrofuran (50 ml), N-methylmorpholine (1.4 ml, 12.7 mmol) and isobutyl chloroformate (1.6 ml, 12.5 mmol) were added at −10° C. The mixture was stirred for 20 minutes and then a suspension of 3α-aminocholestane hydrochloride (5.40 g, 12.7 mmol) and N-methylmorpholine (1.4 ml, 12.7 mmol) in tetrahydrofuran (30 ml) was added. The reaction mixture was stirred for 40 minutes at −10° C., and further stirred for 15 hours at room temperature. After the completion of the reaction, the solvent was evaporated under reduced pressure. To the residue was added ethyl acetate. The mixture was washed with saturated aqueous solution of sodium hydrogen carbonate, 0.2N hydrochloric acid, water, saturated aqueous solution of sodium hydrogen carbonate and water, and dried over anhydrous magnesium sulfate. After the solvent was evaporated under reduced pressure, the syrup was purified by silica gel column chromatography (Merck silica gel 60, eluent: chloroform/methanol (250:1 to 25:1) to obtain the title compound (5.19 g; yield=50.4%).

$^1$H-NMR (CDCl$_3$) δ(ppm): 0.61 (3H, s, 18'-CH$_3$), 0.79–0.88 (12H, 19'-CH$_3$, 21'-CH$_3$, 26'-CH$_3$, 27'-CH$_3$), 1.90, 2.01, 2.03, 2.09, 2.13 (18H, s×6, Ac), 2.58 (1H, dd, J=4.9 Hz, 13.6 Hz, H-3eq), 3.98–4.18 (4H, m, H-3', 5, 6, 9), 4.36 (1H, dd, J=2.7 Hz, 12.3 Hz, H-9), 5.10 (1H, ddd, J=2.7 Hz, 6.2 Hz, 8.9 Hz, H-8), 5.29 (2H, m, H-4, 7), 5.48 (1H, d, J=8.9 Hz, AcNH), 6.85 (1H, d, J=8.0 Hz, NH)

Synthetic Example 2

Synthesis of 3α-[N-(5-acetamido-4,7,8,9-tetra-O-acetyl-2-chloro-2,3,5-trideoxy-β-D-glycero-D-galacto-2-nonulopyranosonyl) amino] cholestane [Compound (V) wherein $R^1$ is 3α-cholestane, $R^2$ is hydrogen and $R^{4'}$ is acetyl).

The compound (6.40 g, 7.20 mmol) obtained in Synthetic example 1 was dissolved in acetyl chloride (75 ml) which was saturated with hydrogen chloride gas. The vessel wherein the reaction mixture was placed was tightly stoppered and was allowed to stand for 16 hours at room temperature. After the completion of the reaction, the solvent was evaporated under reduced pressure and the residue was subjected to azeotropic distillation with benzene to obtain the title compound (6.20 g, yield=99.5%).

$^1$H-MNR (CDCl$_3$) δ(ppm): 0.63 (3H, s, 18'-CH$_3$), 0.79–0.89 (12H, 19'-CH$_3$, 21'-CH$_3$, 26'-CH$_3$, 27'-CH$_3$), 1.90, 2.01, 2.02, 2.10, 2.14 (15H, s×5, Ac), 2.25 (1H, dd, J=11.4 Hz, 14.3 Hz, H-3ax), 2.80 (1H, dd, J=4.8 Hz, 14.3 Hz,

118

H-3eq), 3.98–4.24 (5H, m, H-3', 5, 6, 9, 9), 5.31–5.45 (4H, m, H-4, 7, 8, AcNH), 6.91 (1H, d, J=7.0 Hz, NH)

Example 1

Synthesis of 3α-[N-(5-acetamido-4,7,8,9-tetra-O-acetyl-3,5-dideoxy-2-O-methyl-α-D-glycero-D-galacto-2-nonulopyranosonyl) amino] cholestane (the α-isomer of compound No. 1 in Table 1).

The compound (6.20 g, 7.20 mmol) obtained in Synthetic example 2 was dissolved in dried benzene (75 ml) and anhydrous calcium sulfate (10 g) was added. The mixture was stirred at room temperature for 45 mixtures and then methanol (18.0 ml, 444 mmol) was added. The mixture was stirred for 15 mixtures and then a mixed solution of silver trifluoro-methanesulfonate (2.60 g, 10.1 mmol) and 2,4,6-trimethylpyridine (1.15 ml, 8.75 mmol) in nitromethane (15 ml) and diethyl ether (20 ml) was added under ice cooling and light shading. The reaction mixture was stirred for 15 hours at room temperature, and chloroform was added. The reaction mixture was filtered through celite and the filtrate was washed with 0.2N sodium thiosulfate solution, 0.1 hydrochloric acid, water, saturated aqueous solution of sodium hydrogen carbonate and water, and dried over anhydrous magnesium sulfate. The solvent was evaporated under reduced pressure and the resulting syrup was purified by silica gel column chromatography [Merck silica gel 60, eluent: chloroform/methanol (100:1 to 50:1)] to obtain the title compound (4.13 g, yield=66.9%).

IR (KBr) (cm$^{-1}$) 3380, 2940, 2870, 1750, 1690

$^1$H-NMR (CDCl$_3$) δ(ppm): 0.62 (3H, s, 18'-CH$_3$), 0.77–0.89 (12H, 19'-CH$_3$, 21'-CH$_3$, 26'-CH$_3$, 27'-CH$_3$), 1.86, 1.99, 2.01, 2.04, 2.11 (15H, s×5, Ac), 2.18 (1H, dd, J=5.3 Hz, 13.0 Hz, H-3eq), 3.40 (3H, s, OCH$_3$), 3.99–4.17 (3H, m, H-3', 5, 9), 4.36 (1H, dd, J=1.5 Hz, 11.8 Hz, H-9), 4.47–4.52 (1H, m, H-6), 5.25–5.27 (2H, m, H-7, 8), 5.31–5.42 (2H, m, H-4, AcNH), 5.79 (1H, d, J=7.7 Hz, NH)

Synthetic Example 3

Synthesis of benzyl 5-acetoamido-4,7,8,9-tetra-O-acetyl-3,5-dideoxy-2-O-methyl-α-D-glycero-D-galacto-2-nonulopyranosonate [Compound (X-a) wherein $R^3$ is methyl and $R^{4'}$ is acetyl].

Benzyl 5-acetamido-2,4,7,8,9-penta-O-acetyl-3,5-dideoxy-β-D-glycero-D-galacto-2-nonulopyranosonate (26.5 g, 43.5 mmol) was dissolved in acetyl chloride (200 ml) which was saturated with hydrogen chloride gas. The vessel wherein the reaction mixture was placed was tightly stoppered and allowed to stand for 15 hours at room temperature. The solvent was evaporated under reduced pressure and the residue was subjected twice to azeotropic distillation with toluene (100 ml). To the residue were added silver carbonate (14.6 g) and calcium sulfate (26 g), and then methanol (300 ml) was added. The mixture was stirred under ice cooling for 1 hour and then at room temperature for 3 hours, and filtered through Celite. After the filtrate was concentrated in vacuo, the residue was dissolved in ethyl acetate (500 ml). The solution was washed with water and dried over anhydrous magnesium sulfate. The solvent was evaporated under reduced pressure to obtain the title compound (25.4 g, yield=100%).

m.p. 97°–103° C. (decomposition)

IR (KBr) (cm$^{-1}$) 3290, 1750, 1660

$^1$H-NMR (CDCl$_3$) δ(ppm): 1.87, 2.02, 2.04, 2.13, 2.15 (15H, s×5, Ac), 2.62 (1H, dd, J=4.6 Hz, 12.7 Hz, H-3eq), 3.26 (3H, s, OCH$_3$), 4.31 (1H, dd, J=2.6 Hz, 12.4 Hz, H-9), 4.83 (1H, m, H-4), 5.23 (2H, s, COOC$\underline{H}_2$C$_6$H$_5$), 7.30–7.40 (5H, m, COOCH$_2$C$_6$$\underline{H}_5$)

Synthetic Example 4

Synthesis of 5-acetamido-4,7,8,9-tetra-O-acetyl-3,5-dideoxy-2-O-methyl-α-D-glycero-D-galacto-2-nonulopyranosonic acid [compound (XI-α) wherein R$^3$ is methyl and R$^{4'}$ is acetyl].

The compound which was synthesized in Synthetic example 3 (14.18 g, 24.38 mmol) was dissolved in ethanol (250 ml) and 5% palladium-carbon (1.40 g) was added, and the mixture was stirred in an atmosphere of hydrogen for 3 hours. The catalyst was filtered off and the solvent was evaporated under reduced pressure. The residue was recrystallized from hexane-ethyl acetate to obtain the title compound (10.22 g, yield=85%).

m.p. 189°–190° C. (decomposition)

IR (KBr) (cm$^{-1}$) 3380, 2990, 1740, 1660, 1540

$^1$H-NMR (CD$_3$OD) δ(ppm): 1.79 (1H, t, J=12.4 Hz, H-3ax), 1.87, 2.02, 2.04, 2.13, 2.14 (15H, s×5, Ac), 2.65 (1H, dd, J=4.7 Hz, 12.4 Hz, H-3eq), 3.37 (3H, s, OCH$_3$), 3.99 (1H, t, J=10.5 Hz, H-5), 4.11 (1H, dd, J=5.0 Hz, 12.4 Hz, H-9), 4.26 (1H, dd, J=2.1 Hz, 10.8 Hz, H-6), 4.34 (1H, dd, J=2.5 Hz, 12.4 Hz, H-9), 4.93 (1H, m, H-4), 5.37 (1H, dd, J=2.1 Hz 9.1 Hz, H-7), 5.45 (1H, ddd, J=2.5 Hz, 5.0 Hz, 9.1 Hz, H-8)

Example 2

Synthesis of 3α-[N-(5-acetamido-4,7,8,9-tetra-O-acetyl-3,5-dideoxy-2-O-methyl-α-D-glycero-D-galacto-2-nonulopyronosonyl)amino] cholestane (the α-isomer of compound No. 1 in Table 1).

To a solution of the compound (10.10 g, 20.55 mmol) which was synthesized in Synthetic example 4 in tetrahydrofuran (500 ml), triethylamine (3.15 ml) and isobutyl chloroformate (2.94 ml) were added at −10° C. The mixture was stirred for 1 hour and a solution of 3α-aminocholestane (7.98 g, 20.55 mmol) in tetrahydrofuran (30 ml) was added over 10 minutes. The reaction mixture was warmed to room temperature over a period of 3 hours and further stirred for 12 hours. The precipitated triethylamine hydrochloride was filtered off and the solvent was evaporated under reduced pressure. The residue was dissolved in ethyl acetate (500 ml) and the solution was successively washed with 1N hydrochloric acid, saturated aqueous solution of sodium hydrogen carbonate and saturated saline solution, and dried over anhydrous magnesium sulfate. After the solvent was evaporated under reduced pressure, the syrup was purified by silica gel column chromatography [Merck silica gel 60, eluent: chloroform/methanol (100:1)] to obtain the title compound (15.77 g, yield=89%).

Example 3

Synthesis of 3α-[N-(5-acetamido-3,5-dideoxy-2-O-methyl-α-D-glycero-D-galacto- 2-nonulopyranosonyl) amino] cholestane (the α-isomer of compound No. 4 in Table 1).

The compound (4.13 g, 4.80 mmol) which was obtained in Example 1 or Example 2 was dissolved in methanol (70 ml) and 4.9N sodium methoxide solution (0.3 ml, 1.47 mmol) in methanol was added under ice cooling. The reaction mixture was stirred for 15 hours at room temperature. After the completion of the reaction, about half amount of the solvent was evaporated under reduced pressure. The solid was filtered off and washed with methanol. The resulting solid was triturated with methanol to obtain the title compound (2.53 g; yield=76.2%).

m.p. 269°–280° C. (decomposition)

IR (KBr) (cm$^{-1}$) 3450, 3340, 2960, 1670, 1620

$^1$H-NMR [CDCl$_3$—CD$_3$OD (1:1)] δ(ppm): 0.69 (3H, s, 18'-CH$_3$), 0.84–0.95 (12H, 19'-CH$_3$, 21'-CH$_3$, 26'-CH$_3$, 27'-CH$_3$), 2.04 (3H, s, Ac), 2.82 (1H, dd, J=4.5 Hz, 12.7 Hz, H-3eq), 3.38 (3H, s, OCH$_3$), 4.02 (1H, m, H-3')

Synthetic Example 5

Synthesis of 3α-methylaminocholestane

3α-Aminocholestane (2.00 g, 5.15 mmol) was dissolved in 98–100% formic acid (10 ml) and acetic anhydride (3.6 ml) was added under ice cooling. After the mixture was stirred for 18 hours at room temperature, the precipitated solid was filtered off and recrystallized from methanol to obtain N-formyl-3α-aminocholestane (1.14 g, yield=53%). The N-formyl-3α-aminocholestane was dissolved in tetrahydrofuran (50 ml) and lithium aluminum hydride (415 mg) was added. The mixture was heated under reflux for 1.5 hours. After the completion of the reaction, saturated aqueous solution of sodium sulfate was added to the mixture to decompose an excess of lithium aluminum hydride. Ether (100 ml) was added, and the mixture was stirred and allowed to stand. After the organic layer was collected by decantation, ether (50 ml) was added to the aqueous layer. After the mixture was stirred and allowed to stand, the ether layer was collected again. The organic layers were combined, washed with saturated saline solution, and dried over anhydrous sodium sulfate. After the solvent was evaporated under reduced pressure, the residue was dissolved in ethyl acetate (50 ml) and 4N hydrochloric acid-ethyl acetate (0.7 ml) was added. The resulting precipitate was filtered off. The precipitate was suspended in ether (500 ml) and 40% aqueous solution of potassium hydroxide (100 ml) was added. The suspension was vigorously stirred until the precipitate was dissolved. The ether layer was washed with saturated saline solution and dried over sodium sulfate. The solvent was evaporated under reduced pressure to obtain the title compound (1.04 g, yield=94%).

m.p. 56°–58° C. (decomposition)

IR (KBr) (cm$^{-1}$) 3440, 2930, 1470

$^1$H-NMR (CDCl$_3$) δ(ppm): 0.64 (3H, s, 18-CH$_3$), 0.79 (3H, s, 19-CH$_3$), 0.84–0.92 (9H, 21-CH$_3$, 26-CH$_3$, 27-CH$_3$), 2.38 (3H, s, N—CH$_3$), 2.70 (1H, m, H-3)

Example 4

Synthesis of 3α-[N-(5-acetamido-4,7,8,9-tetra-O-acetyl-3,5-dideoxy-2-O-methyl-α-D-glycero-D-galacto-2-nonulopyranosonyl)-N-methylamino] cholestane (the α-isomer of compound No. 5 in Table 1).

The compound (450 mg, 0.916 mmol) which was synthesized in Synthetic example 4 was dissolved in methylene chloride (40 ml) and pyridine (0.29 ml) and thionyl chloride (0.10 ml) were added under ice cooling. After the mixture was stirred for 5 minutes, the 3α-N-methylaminocholestane (368 mg, 0.916 mmol) which was synthesized in Synthetic example 5 and triethylamine (0.38 ml) were added. The reaction mixture was stirred for 1 hour, diluted with methylene chloride (30 ml), successively washed with 0.1N hydrochloric acid, saturated aqueous solution of sodium hydrogen carbonate and saturated saline solution, and dried over anhydrous magnesium sulfate. The solvent was evaporated under reduced pressure and the syrup was purified by silica gel column chromatography [Merck silica gel 60, eluent; chloroform/methanol (100:1)] to obtain the title compound (560 mg, yield=70%).

IR (KBr) (cm$^{-1}$) 3370, 2940, 1750, 1690, 1640

$^1$H-NMR (CDCl$_3$) δ(ppm): 0.65 (3H, s, 18'-CH$_3$), 0.77–0.86 (12H, 19'-CH$_3$, 21'-CH$_3$, 26'-CH$_3$, 27'-CH$_3$), 1.88, 2.02, 2.04, 2.11, 2.14 (5H, s×5, Ac), 2.54 (1H, dd, J=4.7 Hz, 12.6 Hz, H-3eq), 2.94, 3.24 (3H <1:3>, s×2, N—CH$_3$), 3.33, 3.35 (3H <1:3>, s×2, OCH$_3$), 4.52 (1H, m, H-3'), 5.09 (1H, m, H-4), 5.15 (1H, d, J=10.2 Hz, NH)

Example 5

Synthesis of 3α-[N-(5-acetamido-3,5-dideoxy-2-O-methyl-α-D-glycero-D-galacto-2-nonulopyranosonyl)-N-medthylamino] cholestane (the α-isomer of compound No. 6 in Table 1).

The title compound (206 mg, yield=52%) was obtained by using the compound (469 mg, 0.555 mmol) which was synthesized in Example 4, in a procedure similar to that described in Example 3.

m.p. 222°–228° C.

IR (KBr) (cm$^{-1}$) 3420, 2940, 1630

$^1$H-NMR [CDCl$_3$:CD$_3$OD (1:1)] δ(ppm): 0.68 (3H, s, 18'-CH$_3$), 0.84–0.93 (12H, 19'-CH$_3$, 21'-CH$_3$, 26'-CH$_3$, 27'-CH$_3$), 2.02 (3H, s, Ac), 2.48, 2.67 (1H <1:4>, dd×2, J=4.8 Hz, 12.6 Hz, H-3eq), 2.96, 3.37 (3H <1:4>, s×2, N—CH$_3$), 3.38 (3H, s, OCH$_3$), 3.46 (1H, d, J=9.0 Hz, H-7), 3.55 (1H, dd, J=1.4 Hz, 10.5 Hz, H-9), 4.48 (1H, m, H-3')

Example 6

Synthesis of 3α-[N-(5-acetamido-4,7,8,9-tetra-O-acetyl-3,5-dideoxy- 2-O-ethyl-α-D-glycero-D-galacto-2-nonulopyranosonyl)amino] cholestane (the α-isomer of compound No. 10 in Table 1).

The title compound (355 mg, yield=75.4%) was obtained by using the compound (466 mg, 0.54 mmol) which was made in Synthetic example 2, in a procedure similar to that described in Example 1.

$^1$H-NMR (CDCl$_3$) δ(ppm): 0.62 (3H, s, 18'-CH$_3$), 0.77–0.89 (12H, 19'-CH$_3$, 21'-CH$_3$, 26'-CH$_3$, 27'-CH$_3$), 1.86, 1.98, 2.01, 2.04, 2.11 (15H, s×5, Ac), 2.23 (1H, dd, J=5.1 Hz, 13.0 Hz, H-3eq), 3.54–3.76 (2H, m, OCH$_2$CH$_3$), 3.95–4.17 (3H, m, H-3', 5, 9),4.36 (1H, m, H-9), 4.55 (1H, m, H-6), 5.25–5.36 (4H, m, H-4, 7, 8, AcNH), 6.79 (1H, d, J=7.8 Hz, NH)

Example 7

Synthesis of 3α-[N-(5-acetamido-3,5-dideoxy-2-O-ethyl-α-D-glycero-D-galacto-2-nonulopyranosonyl) amino] cholestane (the α-isomer of compound No. 11 in Table 1).

The title compound (167 mg, yield=62.5%) was obtained by using the compound (331 mg, 0.38 mmol) which was made in Example 6, in a procedure similar to that described in Example 3.

m.p. 256°–263° C.

IR (KBr) (cm$^{-1}$) 3450, 3330, 2940, 1670, 1620

$^1$H-NMR [CDCl$_3$—CD$_3$OD (1:1)] δ(ppm): 0.68 (3H, s, 18'-CH$_3$), 0.83–0.94 (12H, 19'-CH$_3$, 21'-CH$_3$, 26'-CH$_3$, 27'-CH$_3$), 2.04 (3H, s, Ac), 2.83 (1H, dd, J=4.5 Hz, 12.7 Hz, H-3eq), 3.99 (1H, m, H-3')

Example 8

Synthesis of 3α-[N-(5-acetamido-4,7,8,9-tetra-O-acetyl-3,5-dideoxy-2-O-hexyl-α-D-glycero-D-galacto-2-nonulopyranosonyl) amino] cholestane (the α-isomer of compound No. 14 in Table 1).

The title compound (357 mg, yield=83%) was obtained by using the compound (400 mg, 0.462 mmol) which was synthesized in Synthetic example 2 and 1-hexanol (3.4 ml, 27.7 mmol), in a procedure similar to that described in Example 1.

IR (KBr) (cm$^{-1}$) 3430, 2940, 2870, 1750, 1685

$^1$H-NMR (CDCl$_3$) δ(ppm): 0.65 (3H, s, 18'-CH$_3$), 0.81–0.95 (15H, 19'-CH$_3$, 21'-CH$_3$, 26'-CH$_3$, 27'-CH$_3$, —OCH$_2$CH$_2$CH$_2$CH$_2$CH$_2$CH$_3$), 1.89, 2.01, 2.03, 2.06, 2.14 (15H, s×5, Ac), 2.23 (1H, dd, J=5.4 Hz, 13.0 Hz, H-3eq), 3.53–3.71 (2H, m, OCH$_2$CH$_2$CH$_2$CH$_2$CH$_2$CH$_3$), 3.56 (1H, m, H-3'), 3.57 (1H, dd, J=6.6 Hz, 12.5 Hz, H-9), 4.12 (1H, q, J=10.5 Hz, H-5), 4.37 (1H, dd, J=2.0 Hz, 12.5 Hz H-9), 4.51 (1H, dd, J=2.0 Hz, 10.5 Hz, H-6), 5.24 (1H, m, H-4), 5.27 (1H, m, H-7), 5.37–5.46 (2H, m, H-8, AcNH), 6.90 (1H, d, J=8.0 Hz, NH)

Example 9

Synthesis of 3α-[N-(5-acetamido-3,5-dideoxy-2-O-hexyl-α-D-glycero-D-galacto-2-nonulopyranosonyl) amino] cholestane [the α-isomer of compound No. 15 in Table 1).

The compound (337 mg, 0.362 mmol) which was synthesized in Example 8 was dissolved in methanol (5 ml) and a 4.9N solution of sodium methoxide in methanol (0.1 ml, 0.49 mmol) was added. The mixture was stirred overnight. The reaction liquid was neutralized by addition of Dowex (50 W×8, H+) resin and filtered. The filtrate was purified by column chromatography (ODS MCIGEL, eluent: water/methanol) to obtain the title compound (194 mg, yield=70%).

m.p.138°–148° C.

IR (KBr) (cm$^{-1}$) 3400, 2930, 1660

$^1$H-NMR (CD$_3$OD) δ(ppm): 0.73 (3H, s, 18'-CH$_3$), 0.80–0.98 (15H, 19'-CH$_3$, 21'-CH$_3$, 26'-CH$_3$, 27'-CH$_3$, —OCH$_2$CH$_2$CH$_2$CH$_2$CH$_3$), 2.04 (3H, s, Ac), 2.87 (1H, dd, J=4.4 Hz, 12.7 Hz, H-3eq), 3.97 (1H, m, H-3')

Example 10

Synthesis of 3α-[N-(5-acetamido-4,7,8,9-tetra-O-acetyl-3,5-dideoxy-2-O-benzyl-α-D-glycero-D-galacto-2-nonulopyranosonyl) amino] cholestane (the α-isomer of compound No. 20 in Table 1) and 3α-[N-(5-acetamido-4,7,8,9-tetra-O-acetyl- 3,5-dideoxy-2-O-benzyl-β-D-glycero-D-galacto-2-nonulopyranosonyl) amino] cholestane (the α-isomer of compound No. 280 in Table 3).

The title compounds [the α-isomer of compound No. 20 in Table 1 (365 mg, yield=61.6%) and the α-isomer of compound No. 280 in Table 3 (35.4 mg, yield=6.0%)] were simultaneously obtained by using the compound (548 mg, 0.63 mmol) which was made in Synthetic example 2 and benzyl alcohol (0.70 ml, 6.80 mmol), in a procedure similar to that described in Example 1.

The α-isomer of compound No. 20 in Table 1

$^1$H-NMR (CDCl$_3$) δ(ppm): 0.61 (3H, s, 18'-CH$_3$), 0.73–0.91 (12H, 19'-CH$_3$, 21'-CH$_3$, 26'-CH$_3$, 27'-CH$_3$), 1.87, 1.99, 2.01, 2.05, 2.10 (15H, s×5, Ac), 2.32 (1H, dd, J=5.2 Hz, 13.1 Hz, H-3eq), 3.96–4.05 (2H, m, H-3', 9), 4.16 (1H, m, H-5), 4.31 (1H, m, H-9), 4.62–4.81 (3H, m, H-6,

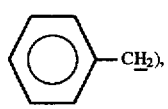, 5.27–5.43 (4H, m, H-4, 7, 8, AcNH), 6.87 (1H, d, J=7.9 Hz, NH), 7.26–7.38 (5H, m,

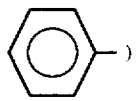)

The α-isomer of compound No. 280 in Table 3
$^1$H-NMR (CDCl$_3$) δ(ppm): 0.62 (3H, s, 18'-CH$_3$), 0.79–0.88 (12H, 19'-CH$_3$, 21'-CH$_3$, 26'-CH$_3$, 27'-CH$_3$), 1.78, 1.88, 1.99, 2.15 (15H, s×5, Ac), 2.63 (1H, dd, J=4.8 Hz, 13.4 Hz, H-3eq), 4.00–4.49 (7H, m, H-3', 5, 6, 9, 9,

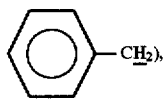, 5.24–5.32 (3H, m, H-4, 7, 8), 5.42 (1H, d, J=9.6 Hz, AcNH), 7.05 (1H, d, J=7.7 Hz, NH), 7.25–7.33 (5H, m,

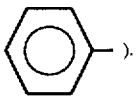).

Example 11

Synthesis of 3α-[N-(5-acetamido-3,5-dideoxy-2-O-benzyl-α-D-glycero-D-galacto-2-nonulopyranosonyl) amino] cholestane (the α-isomer of compound No. 21 in Table 1).

The title compound (130 mg, yield=43.6%) was obtained by using the α-isomer of compound No. 20 in Table 1 (363 mg, 0.39 mmol) which was made in Example 10, in a procedure similar to that described in Example 9.

IR (KBr) (cm$^{-1}$) 3420, 2940, 2860, 1660

$^1$H-NMR (CD$_3$OD) δ(ppm): 0.71 (3H, s, 18'-CH$_3$), 0.86–0.99 (12H, 19'-CH$_3$, 21'-CH$_3$, 26'-CH$_3$, 27'-CH$_3$), 2.06 (3H, s, Ac), 2.95 (1H, dd, J=4.4 Hz, 12.6 Hz, H-3eq), 4.01 (1H, m, H-3'), 7.29–7.38 (5H, m,

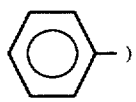)

Example 12

Synthesis of 3α-[N-[5-acetamido-4,7,8,9-tetra-O-acetyl-3,5-dideoxy-2-O-( 4-methoxycarbonylbenzyl)-α-D-glycero-D-galacto-2-nonulopyranosonyl] amino] cholestane (the isomer of compound No. 130 in Table 1).

The title compound (179 mg, yield=28.2%) was obtained by using the compound (551 mg, 0.64 mmol) which was made in Synthetic example 2 and methyl 4-hydroxymethyl benzoate (258 mg, 1.55 mmol), in a procedure similar to that described in Example 1.

$^1$H-NMR (CDCl$_3$) δ(ppm): 0.59 (3H, s, 18'-CH$_3$), 0.72 (3H, s, 19'-CH$_3$), 0.82–0.91 (9H, 21'-CH$_3$, 26'-CH$_3$, 27'-CH$_3$), 1.88, 2.00, 2.01, 2.06, 2.08 (15H, s×5, Ac), 2.33 (1H, dd, J=5.3 Hz, 13.1 Hz, H-3eq), 3.90 (3H, s, COOCH$_3$), 3.93–3.99 (2H, m, H-3', 9), 5.26–5.40 (4H, m, H-4,7,8, AcNH), 6.82 (1H, d, J=7.7 Hz, NH), 7.45 (2H, m,

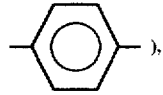, 8.04 (2H, m,

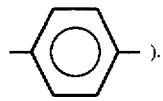.

Example 13

Synthesis of 3α-[N-[5-acetamido-3,5-dideoxy-2-O-(4-methoxycarbonylbenzyl)-α-D-glycero-D-galacto-2-nonulopyranosonyl] amino] cholestane (the α-isomer of compound No. 131 in Table 1).

The title compound (83.3 mg, yield=55.9%) was obtained by using the compound (179 mg, 0.18 mmol) which was made in Example 12, in a procedure similar to that described in Example 9.

m.p. 185°–205° C.

IR (KBr) (cm$^{-1}$) 3430, 2940, 2860, 1730, 1660

$^1$H-NMR (CD$_3$OD) δ(ppm): 0.70 (3H, s, 18'-CH$_3$), 0.84 (3H, s, 19'-CH$_3$), 0.91–0.99 (9H, 21'-CH$_3$, 26'-CH$_3$, 27'-CH$_3$), 2.06 (3H, s, Ac), 2.96 (1H, dd, J=4.3 Hz, 12.5 Hz, H-3eq), 3.94 (3H, s, COOCH$_3$), 4.85 (2H, s, OCH$_2$

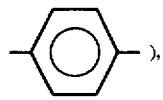, 7.51 (2H, m,

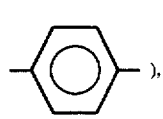, 8.04 (2H, m,

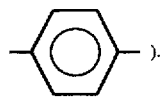.

Example 14

Synthesis of sodium 3α-[N-[5-acetamido-3,5-dideoxy-2-O-(4-carboxybenzyl)-α-D-glycero-D-galacto-2-nonulopyranosonyl] amino] cholestane. (The sodium salt of the α-isomer of compound No. 129 in Table 1).

To a solution of the compound (59.8 mg, 0.072 mmol) which was obtained in Example 13 in tetrahydrofuran (15 ml), 0.1N aqueous solution of sodium hydroxide (1.5 ml, 0.15 mmol) was added and the mixture was stirred for 5 days under reflux. The reaction mixture was neutralized with Dowex (50 W×8, H+). The resin was filtered off and the filtrate was concentrated in vacuo.

The resulting syrup was purified by column chromatography (ODS MCIGEL, eluent; water/methanol) and the title compound (4.8 mg, yield=7.9%) was solidified by trituration with diethyl ether.

IR (KBr) (cm$^{-1}$) 3430, 2950, 2870, 1700, 1650

$^1$H-NMR (CD$_3$OD) δ(ppm): 0.70 (3H, s, 18'-CH$_3$), 0.85 (3H, s, 19'-CH$_3$), 0.90–0.98 (9H, 21'-CH$_3$, 26'-CH$_3$, 27'-CH$_3$), 2.06 (3H, s, Ac), 2.98 (1H, dd, J=4.3 Hz, 12.5 Hz, H-3eq), 3.98 (1H, m, H-3'), 4.84 (1H, d, J=5.1 Hz, OC$\underline{H}_2$

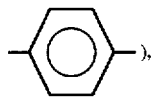

7.48 (2H, m,

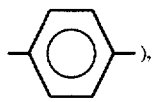

8.03 (2H, m,

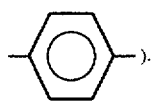

Example 15

Synthesis of 3α-[N-[5-acetamido-4,7,8,9-tetra-O-acetyl-3,5-dideoxy-2-O-(2-methoxyethyl)-α-D-glycero-D-galacto-2-nonulopyranosonyl] amino] cholestane (the α-isomer of compound No. 139 in Table 1).

The title compound (327 mg, yield=78%) was obtained by using the compound (400 mg, 0.462 mmol) which was synthesized in Synthetic example 2 and 2-methoxyethanol (2.17 ml, 27.7 mmol), in a procedure similar to that described in Example 1.

IR (KBr) (cm$^{-1}$) 3380, 2940, 2870, 1750, 1670

$^1$H-NMR (CDCl$_3$) δ(ppm): 0.65 (3H, s, 18'-CH$_3$), 0.79 (3H, s, 19'-CH$_3$), 0.84–0.96 (9H, 21'-CH$_3$, 26'-CH$_3$, 27'-CH$_3$), 1.89, 2.01, 2.03, 2.06, 2.14 (15H, s×5, Ac), 2.25 (1H, dd, J=5.0 Hz, 13.0 Hz, H-3eq), 3.41 (3H, s, OCH$_3$), 3.58 (1H, m, OC$\underline{H}_2$CH$_2$OCH$_3$), 3.60 (1H, d, J=8.0 Hz, OCH$_2$C$\underline{H}_2$OCH$_3$), 3.66 (1H, d, J=8.0 Hz, OCH$_2$C$\underline{H}_2$OCH$_3$), 3.85 (1H, m, OC$\underline{H}_2$CH$_2$OCH$_3$), 3.98 (1H, m, H-3'), 4.02 (1H, dd, J=5.9 Hz, 12.2 Hz, H-9), 4.14 (1H, q, J=10.5 Hz, H-5), 4.27 (1H, dd, J=2.2 Hz, 12.2 Hz, H-9), 4.95 (1H, dd, J=2.1 Hz, 10.5 Hz, H-6), 5.24–5.35 (4H, H-4, 7, 8, AcN$\underline{H}$), 7.13 (1H, d, J=7.5 Hz, NH)

Example 16

Synthesis of 3α-[N-[5-acetamido-3,5-dideoxy-2-O-(2-methoxyethyl)-α-D-glycero-D-galacto-2-nonulopyranosonyl]amino] cholestane (the α-isomer of compound No. 1 40 in Table 1).

The title compound (56 mg, yield=54%) was obtained by using the compound (130 mg, 0.144 mmol) which was made in Example 15, in a procedure similar to that described in Example 9.

m.p. 218°–220° C. (decomposition)

IR (KBr) (cm$^{-1}$) 3340, 2930, 2870, 1665

$^1$H-NMR (CD$_3$OD) δ(ppm): 0.73 (3H, s, 18'-CH$_3$), 0.89–0.99 (12H, 19'-CH$_3$, 21'-CH$_3$, 26'-CH$_3$, 27'-CH$_3$), 2.06 (3H, s, Ac), 2.83 (1H, dd, J=4.6 Hz, 12.7 Hz, H-3eq), 3.40 (3H, s, OCH$_3$), 4.01 (1H, m, H-3')

Example 17

Synthesis of 3α-[N-[5-acetamido-4 7,8,9-tetra-O-acetyl-2-O-(2-benzyloxyethyl)-3,5-dideoxy-α-D-glycero-D-galacto-2-nonulopyranosonyl] amino] cholestane (the α-isomer of compound No. 162 in Table 1).

The title compound (578 mg, yield=51%) was obtained by using the compound (1.00 g, 1.16 mmol) which was synthesized in Synthetic example 2 and 2-benzyloxyethanol (3.30 ml, 23.2 mmol), in a procedure similar to that described in Example 1.

IR (KBr) (cm$^{-1}$) 3380, 2940, 2870, 1750, 1680

$^1$H-NMR (CDCl$_3$) δ(ppm): 0.61 (3H, s, 18'-CH$_3$), 0.76 (3H, s, 19'-CH$_3$), 0.85–0.88 (9H, 21'-CH$_3$, 26'-CH$_3$, 27'-CH$_3$), 1.89, 2.01, 2.02, 2.06, 2.12 (15H, s×5, Ac), 2.26 (1H, dd, J=5.0 Hz, 12.9 Hz, H-3eq), 3.66 (2H, brs, CH$_2$C$\underline{H}_2$OCH$_2$C$_6$H$_5$), 3.69 (1H, m, C$\underline{H}_2$CH$_2$OCH$_2$C$_6$H$_5$), 3.89 (1H, m, C$\underline{H}_2$CH$_2$OCH$_2$C$_6$H$_5$), 4.00 (1H, m, H-3'), 4.01 (1H, dd, J=5.6 Hz, 12.5 Hz, H-9), 4.13 (1H, q, J=10.5 Hz, H-5), 4.27 (1H, dd, J=2.1 Hz, 12.5 Hz, H-9), 4.58 (1H, d, J=12.8 Hz, C$\underline{H}_2$C$_6$H$_5$), 4.68 (1H, d, J=12.8 Hz, C$\underline{H}_2$C$_6$H$_5$), 4.88 (1H, dd, J=1.9 Hz, 10.5 Hz, H-6), 5.23–5.34 (4H, H-4, 7, 8, AcN$\underline{H}$), 7.11 (1H, d, J=7.4 Hz, NH), 7.34 (5H, m, C$_6$H$_5$)

Example 18

Synthesis of 3α-[N-[5-acetamido-2-O-(2-benzyloxyethyl)-3,5-dideoxy-α-D-glycero-D-galacto-2-nonulopyranosonyl] amino] cholestane (the α-isomer of compound No. 163 in Table 1).

The title compound (94 mg, yield=57%) was obtained by using the compound (200 mg, 0.209 mmol) which was synthesized in Example 17, in a procedure similar to that described in Example 9.

m.p. 127°–135° C. (decomposition)

IR (KBr) (cm$^{-1}$) 3400, 2930, 2860, 1655

$^1$H-NMR (CD$_3$OD) δ(ppm): 0.69 (3H, s, 18'-CH$_3$), 0.86 (3H, s, 19'-CH$_3$), 0.91–0.97 (9H, 21'-CH$_3$, 26'-CH$_3$, 27'-CH$_3$), 2.04 (3H, s, Ac), 2.84 (1H, dd, J=4.3 Hz, 12.7 Hz, H-3eq), 4.00 (1H, m, H-3'), 4.58 (1H, d, J=12.0 Hz, CH$_2$C$_6$H$_5$), 4.64 (1H, d, J=12.0 Hz, C$\underline{H}_2$C$_6$H$_5$), 7.40 (5H, m, C$_6$H$_5$)

Example 19

Synthesis of 3α-[N-[5-acetamido-4,7,8,9-tetra-O-acetyl-3,5-dideoxy-2-O-(2-hydroxyethyl)-α-D-glycero-D-galacto-2-nonulopyranosonyl] amino] cholestane (the α-isomer of compound No. 135 in Table 1).

The compound (334 mg, 0.349 mmol) which was synthesized in Example 17 was dissolved in ethanol (10 ml) and 5% palladium-carbon (30 mg) was added. The mixture was stirred in an atmosphere of hydrogen for 2 hours. The catalyst was filtered off and the solvent of the filtrate was evaporated under reduced pressure to obtain the title compound (294 mg, yield=97%).

IR (KBr) (cm$^{-1}$) 3380, 2940, 2870, 1750, 1670

$^1$H-NMR (CDCl$_3$) δ(ppm): 0.65 (3H, s, 18'-CH$_3$), 0.80 (3H, s, 19'-CH$_3$), 0.85–0.96 (9H, 21'-CH$_3$, 26'-CH$_3$, 27'-CH$_3$), 1.88, 2.02, 2.04, 2.08, 2.15 (15H, s×5, Ac), 2.34 (1H, dd, J=5.2 Hz, 12.9 Hz, H-3eq), 3.80 (4H, m, C$\underline{H}_2$C$\underline{H}_2$OH), 3.95 (1H, dd, J=6.6 Hz, 12.3 Hz, H-9), 4.03 (1H, m, H-3'), 4.15 (1H, q, J=10.5 Hz, H-5), 4.53 (2H, dd×2, J=2.0 Hz, 10.5 Hz, 12.3 Hz, H-6, 9), 5.22–5.37 (4H, H-4, 7, 8, NH), 7.80 (1H, d, J=7.3 Hz, NH)

Example 20

Synthesis of 3α-[N-[5-acetamido-3,5-dideoxy-2-O-(2-hydroxyethyl)-α-D-glycero-D-galacto-2-nonulopyranosonyl] amino] cholestane (the α-isomer of compound 136 in Table 1).

The title compound (182 mg, yield=90%) was obtained by using the compound (248 mg, 0.286 mmol) which was synthesized in Example 19, in a procedure similar to that described Example 9.

m.p. 259°–261° C. (decomposition)

IR (KBr) (cm$^{-1}$) 3400, 2920, 2860, 1660, 1645

$^1$H-NMR (CD$_3$OD) δ(ppm): 0.73 (3H, s, 18'-CH$_3$), 0.88–0.98 (12H, 19'-CH$_3$, 21'-CH$_3$, 26'-CH$_3$, 27'-CH$_3$), 2.05 (3H, s, Ac), 2.83 (1H, dd, J=4.4 Hz, 12.8 Hz, H-3eq), 4.03 (1H, m, H-3')

Example 21

Synthesis of 3α-[N-[5-acetamido-2-O-(2-benzyloxycarbonylaminoethyl)-3,5-dideoxy-α-D-glycero-D-galacto-2-nonulopyranosonyl] amino] cholestane (the α-isomer of compound No. 223 in Table 1).

A mixture of 3α-[N-[5-acetamido-4,7,8,9-tetra-O-acetyl-2-O-(2-benzyloxycarbonylaminoethyl)-3,5-dideoxy-α-D-glycero-D-galacto-2-nonulopyranosonyl] amino] cholestane and the β-anomer of the 2-position of sialic acid (808 mg, yield=67%, ratio: about 8:2) was obtained by using the compound (1.00 g, 1.16 mmol) which was synthesized in Synthetic example 2 and 2-benzyloxycarbonylaminoethanol (4.53 g, 23.2 mmol), in a procedure similar to that described in Example 1. The mixture (352 mg) was dissolved in methanol (5 ml) and 4.9N solution of sodium methoxide in methanol (0.07 ml, 0.34 mmol) was added. The mixture was stirred at room temperature for 4 hours. The reaction mixture was neutralized by addition of Dowex (50 W×8, H+) and filtered. The filtrate was purified by column chromatography (DOS MCIGEL, eluent: water/methanol) to obtain the title compound (40 mg, yield=13%).

m.p. 230°–238° C. (decomposition)

IR (KBr) (cm$^{-1}$) 3330, 2940, 2870, 1710, 1655, 1530

$^1$H-NMR (CD$_3$OD) δ(ppm): 0.71 (3H, s, 18'-CH$_3$), 0.87 (3H, s, 19'-CH$_3$), 0.91–0.94 (9H, 21'-CH$_3$, 26'-CH$_3$, 27'-CH$_3$), 2.05 (3H, s, Ac), 2.84 (1H, dd, J=4.3 Hz, 12.5 Hz, H-3eq), 3.30–3.40 (4H, m, C$\underline{H}_2$C$\underline{H}_2$NHZ), 4.00 (1H, m, H-3'), 5.09 (1H, d, J=12.0 Hz, OC$\underline{H}_2$C$_6$H$_5$), 5.14 (1H, d, J=12.0 Hz, OC$\underline{H}_2$C$_6$H$_5$), 7.39 (5H, m, C$_6$H$_5$)

Example 22

Synthesis of 3α-[N-[5-acetamido-4,7,8,9-tetra-O-acetyl-2-O-(2-aminoethyl)-3,5-dideoxy-α-D-glycero-D-galacto-2-nonulopyranosonyl] amino] cholestane (The α-isomer of compound No. 181 in Table 1).

The mixture (500 mg) of 3α-[N-[5-acetamido-4,7,8,9-tetra-O-acetyl-2-O-(2-benzyloxycarbonylaminoethyl)-3,5-dideoxy-α-D-glycero-D-galacto-2-nonulopyranosonyl] amino] cholestane and the β-anomer of the 2-position of sialic acid which was synthesized in Example 21 was further purified by column chromatography (ODS MCIGEL, eluent: water/methanol) to obtain only the α-anomer (374 mg, 0.365 mmol). The α-anomer was dissolved in ethanol (10 ml) and 5% palladium-carbon (50 mg) was added. The mixture was stirred in an atmosphere of hydrogen for 4 hours. The catalyst was filtered off and the solvent was evaporated under reduced pressure to obtain the title compound (301 mg, yield=69%).

IR (KBr) (cm$^{-1}$) 3380, 2940, 2870, 1750, 1670

$^1$H-NMR (CDCl$_3$) δ(ppm): 0.65 (3H, s, 18'-CH$_3$), 0.80 (3H, s, 19'-CH$_3$), 0.82–0.91 (9H, 21'-CH$_3$, 26'-CH$_3$, 27'-CH$_3$), 1.88, 2.01, 2.03, 2.07, 2.15 (15H, s×5, Ac), 2.29 (1H, dd, J=12.8, 5.1 Hz, H-3eq), 2.93 (2H, t, J=5.2 Hz, CH$_2$C$\underline{H}_2$NH$_2$), 3.56 (1H, m, C$\underline{H}_2$CH$_2$NH$_2$), 3.73 (1H, m, C$\underline{H}_2$CH$_2$NH$_2$), 3.94–4.10 (3H, m, H-9, H-3', AcN$\underline{H}$), 4.16 (1H, q, J=10.5 Hz, H-5), 4.42 (1H, d, J=12.4 Hz, H-9), 4.64 (1H, d, J=10.5 Hz, H-6), 5.27 (1H, d, J=2.2 Hz, H-7), 5.28–5.41 (3H, m, H-4, 8, NH)

Example 23

Synthesis of 3α-[N-[5-acetamido-2-O-(2-aminoethyl)-3,5-dideoxy-α-D-glycero-D-galacto-2-nonulopyranosonyl] amino] cholestane hydrochloride (the hydrochloride salt of the α-isomer of compound No. 182 in Table 1).

The compound (54 mg, 0.061 mmol) which was synthesized in Example 22 was dissolved in methanol (1 ml) and 4.9N solution of sodium methoxide in methanol (0.01 ml, 0.049 mmol) was added. The mixture was stirred at room temperature for 2.5 hours. The reaction mixture was neutralized by addition of Dowex (50 W×8, H+) resin and filtered. To the filtrate was added 4N hydrochloric acid-ethyl acetate (20 μl) and the solvent was evaporated under reduced pressure. The resulting syrup was solidified by trituration with methanol-ether to obtain the title compound (23 mg, yield=50%).

m.p. 154°–162° C.

IR (KBr) (cm$^{-1}$) 3380, 2920, 1650

$^1$H-NMR (CD$_3$OD) δ(ppm): 0.73 (3H, s, 18'-CH$_3$), 0.78–0.98 (12H, 19'-CH$_3$, 21'-CH$_3$, 26'-CH$_3$, 27'-CH$_3$), 2.07 (3H, s, Ac), 2.85 (1H, dd, J=13.2 Hz, 4.7 Hz, H-3eq), 3.17 (2H, m, —CH$_2$C$\underline{H}_2$NH$_2$), 4.05 (1H, m, H-3')

Example 24

Synthesis of 3α-[N-[5-acetamido-4,7,8,9-tetra-O-acetyl-2-O-(2-acetamidoethyl)-3,5-dideoxy-α-D-glycero-D-galacto-2-nonulopyranosonyl] amino] cholestane (the α-isomer of compound No. 195 in Table 1).

The compound (130 mg, 0.146 mmol) which was synthesized in Example 22 was dissolved in methylene chloride (2 ml), and acetyl chloride (12 μl) and triethylamine (24 μl) were added under ice-cooling. After stirring for 1 hour, chloroform (10 ml) was added and the reaction mixture was washed with 0.1N hydrochloric acid, saturated aqueous solution of sodium hydrogen carbonate and saturated saline solution, and dried over anhydrous magnesium sulfate. The solvent was evaporated under reduced pressure and the resulting syrup was purified by column chromatography [Merck silica gel 60, eluent: chloroform/methanol (200:1 to 100:1)] to obtain the title compound (91 mg, yield=67%).

IR (KBr) (cm$^{-1}$) 3380, 2940, 2870, 1750, 1670

$^1$H-NMR (CDCl$_3$) δ(ppm): 0.65 (3H, s, 18'-CH$_3$), 0.81 (3H, s, 19'-CH$_3$), 0.84–0.91 (9H, 21'-CH$_3$, 26'-CH$_3$, 27'-CH$_3$), 1.88, 2.01, 2.03, 2.04, 2.07, 2.15 (18H, s×6, Ac), 2.28 (1H, dd, J=5.4 Hz, 13.1 Hz, H-3eq), 3.52 (2H, t, J=5.0 Hz, CH$_2$C$\underline{H}_2$NHAc), 3.76 (2H, t, J=5.0 Hz, C$\underline{H}_2$CH$_2$NHAc), 3.94 (1H, dd, J=6.8 Hz, 12.5 Hz, H-9), 4.02 (1H, m, H-3'), 4.16 (1H, q, J=10.5 Hz, H-5), 4.43 (1H, dd, J=1.7 Hz, 10.5 Hz, H-6), 4.51 (1H, dd, J=2.0 Hz, 12.5 Hz, H-9), 5.23 (1H, m, H-4), 5.29 (1H, brs, H-7), 5.34–5.44 (2H, m, H-8, AcN$\underline{H}$), 6.33 (1H, t, J=1.7 Hz, AcN$\underline{H}$), 6.93 (1H, d, J=7.5 Hz, NH)

Example 25

Synthesis of 3α-[N-[5-acetamido-2-O-(2-acetamidoethyl)-3,5-dideoxy-α-D-glycero-D-galacto- 2-nonulopyranosonyl] amino] cholestane (the α-isomer of compound No. 196 in Table 1).

The title compound (28 mg. yield=40%) was obtained by using the compound (85 mg. 0.091 mmol) which was synthesized in Example 24, in a procedure similar to that described in Example 9.

m.p. 139°–146° C. (decomposition)

IR (KBr) (cm$^{-1}$) 3400, 2940, 1650

$^1$H-NMR (CD$_3$OD) δ(ppm): 0.73 (3H, s, 18'-CH$_3$), 0.79 (3H, s, 19'-CH$_3$), 0.83–0.98 (9H, 21'-CH$_3$, 26'-CH$_3$, 27'-CH$_3$), 1.99 (3H, s, Ac), 2.04 (3H, s, Ac), 2.86 (1H, dd, J=12.8 Hz, 4.5 Hz, H-3eq), 4.02 (1H, m, H-3')

Example 26

Synthesis of 3α-[N-[5-acetamido-4,7,8,9-tetra-O-acetyl-3,5-dideoxy-2-O-(2-methanesulfonylaminoethyl)-α-D-glycero-D-galacto-2-nonulopyranosonyl] amino] cholestane (the α-isomer of the compound No. 201 in Table 1).

The compound (180 mg, 0.202 mmol) which was synthesized in Example 22 was dissolved in methylene chloride (2 ml), and methanesulfonyl chloride (19 µl, 0.24 mmol) and triethylamine (34 µl, 0.24 mmol) were added under ice cooling. After stirring for 2 hours, chloroform (10 ml) was added and the reation mixture was washed with 0.1N hydrochloric acid, saturated aqueous solution of sodium hydrogen carbonate and saturated saline solution, and dried over anhydrous magnesium sulfate. The solvent was evaporated under reduced pressure and the resulting syrup was purified by silica gel column chromatography [Merck silica gel 60, eluent: chloroform/methanol (200:1 to 100:1) to obtain the title compound (125 mg, yield=64%).

IR (KBr) (cm$^{-1}$) 3400, 2930, 1750, 1670

$^1$H-NMR (CDCl$_3$) δ(ppm): 0.65 (3H, s, 18'-CH$_3$), 0.80 (3H, s, 19'-CH$_3$), 0.85–0.91 (9H, 21'-CH$_3$, 26'-CH$_3$, 27'-CH$_3$), 1.87, 2.02, 2.07, 2.09, 2.16 (15H, s×5, Ac), 2.43 (1H, dd, J=5.2 Hz, 12.7 Hz, H-3eq), 2.98 (3H, s, Ms), 3.37 (2H, m, CH$_2$CH$_2$NHMs), 3.83 (2H, m, CH$_2$CH$_2$NHMs), 3.89 (1H, dd, J=8.3 Hz, 12.3 Hz, H-9), 4.04 (1H, m, H-3'), 4.13 (1H, q, J=10.0 Hz, H-5), 4.23 (1H, dd, J=2.3 Hz, 10.0 Hz, H-6), 4.72 (1H, dd, J=2.0 Hz, 12.3 Hz, H-9), 5.18 (1H, m, H-4), 5.28–5.41 (4H, m, H-7, 8, NHAc, NHMs), 7.03 (1H, d, J=7.1 Hz, NH)

Example 27

Synthesis of 3α-[N-[5-acetamido-3,5-dideoxy-2-O-(2-methanesulfonylaminoethyl)-α-D-glycero-D-galacto-2-nonulopyranosonyl] amino] cholestane (the α-isomer of compound No. 202 in Table 1).

The title compound (34 mg. yield=40%) was obtained by using the compound (103 mg, 0.106 mmol) which was synthesized in Example 26, in a procedure similar to that described in Example 9.

mp. 137°–145° C.

IR (KBr) (cm$^{-1}$) 3400, 2950, 2870, 1655

$^1$H-NMR (CD$_3$OD) δ(ppm): 0.73 (3H, s, 18'-CH$_3$), 0.85 (3H, s, 19'-CH$_3$), 0.88–0.98 (9H, 21'-CH$_3$, 26'-CH$_3$, 27'-CH$_3$), 2.05 (3H, s, Ac), 2.85 (1H, dd, J=4.6 Hz, 12.8 Hz, H-3eq), 3.01 (3H, s, Ms), 3.29 (2H, t, J=5.3 Hz, CH$_2$CH$_2$NHMs), 4.03 (1H, m, H-3')

Example 28

Synthesis of 3α-[N-(5-acetamido-3,5-dideoxy-2-O-phenyl-α-D-glycero-D-galacto-2-nonulopyranosonyl) amino] cholestane (the α-isomer of compound 19 in Table 1).

The compound (534 mg, 0.62 mmol) which was obtained in Synthetic example 2 was dissolved in dried acetonitrile (10 ml) and powder molecular sieve 4 A (1.0 g) was added. The mixture was stirred at room temperature for 30 minutes and subsequently a solution of tetra-n-butylammonium phenoxide (2.50 g, 3.91 mmol) in acetonitrile (10 ml) was added. After the mixture was stirred for 15 minutes, silver carbonate (270 mg, 0.98 mmol) was added under light shading and the mixture was stirred for 12 hours.

To the reaction mixture was added chloroform and the resulting mixture was filtered through Celite. The filtrate was concentrated and the resulting syrup was purified by silica gel column chromatography [Merck silica gel 60, eluent: chloroform/methanol (100:1) to obtain 3α-[N-(5-acetamido-4,7, 8,9-tetra-O-acetyl-3,5-dideoxy-2-O-phenyl-α-D-glycero-D-galacto-2-nonulopyranosonyl) amino] cholestane as an oil.

The oil was dissolved in methanol (10 ml) and 4.9N solution of sodium methoxide in methanol (0.1 ml, 0.49 mmol) was added under ice cooling. Subsequently, the mixture was stirred at room temperature for 23 hours. The reaction mixture was neutralized with Dowex (50 W×8, H+) and the resin was filtered off. The filtrate was concentrated and the resulting syrup was purified by column chromatography (ODS MCIGEL, eluent: water methanol) and solidified by trituration with methanol-water to obtain the title compound (51.0 mg, yield: 10.9%).

m.p.180°–183° C.

IR (KBr) (cm$^{-1}$) 3300, 2950, 2880, 1640

$^1$H-NMR (CD$_3$OD) δ(ppm): 0.71 (3H, s, 18'-CH$_3$), 0.76 (3H, s, 19'-CH$_3$), 0.91–0.99 (9H, 21'-CH$_3$, 26'-CH$_3$, 27'-CH$_3$), 2.05 (3H, s, Ac), 3.11 (1H, dd, J=4.4 Hz, 12.5 Hz, H-3eq), 7.13–7.36 (5H, m,

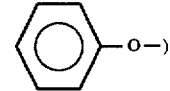

Example 29

Synthesis of 3α-[N-[5-acetamido-3,5-dideoxy-2-O-(4-chlorophenyl)-α-D-glycero-D-galacto-2-nonulopyranosonyl] amino] cholestane (the α-isomer of compound No. 26 in Table 1).

The compound (514 mg, 0.59 mmol) which was obtained in Synthetic example 2 was dissolved in dried dimethylformamide (10 ml) and sodium 4-chlorophenoxide (100 mg, 0.66 mmol) was added under ice cooling. After stirring at room temperature for 24 hours, ethyl acetate was added and the reaction mixture was washed with water and dried over anhydrous magnesium sulfate. The solvent was evaporated under reduce pressure and the resulting syrup was purified by silica gel column chromatography [Merck silica gel 60, eluent: chloroform/methanol (200:1 to 50:1) to obtain 3α-[N-[5-acetamido-4,7,8,9-tetra-O-acetyl-3,5-dideoxy-2-O-(4-chlorophenyl)-α-D-glycero-D-galacto-2-nonulopyranosonyl] amino] cholestane as an oil.

The oil was dissolved in methanol (10 ml) and 4.9N solution of sodium methoxide in methanol (0.1 ml, 0.49 mmol) was added under ice cooling. After stirring at room temperature for 12 hours, the reaction mixture was neutralized with Dowex (50 W×8, H+) and then the resin was filtered off. The filtrate was concentrated and the resulting syrup was purified by column chromatography (ODS MCIGEL, eluent: water/methanol) and solidified by trituration with water to obtain the title compound (32.0 mg, yield=6.8%).

m.p.193°–196° C.

IR (KBr) (cm⁻¹) 3420, 2930, 2860, 1660

¹H-NMR (CD₃OD) δ(ppm): 0.71 (3H, s, 18'-CH₃), 0.77 (3H, s, 19'-CH₃), 0.91–0.99 (9H, 21'-CH₃, 26'-CH₃, 27'-CH₃), 2.05 (3H, s, Ac), 3.11 (1H, dd, J=4.5 Hz, 12.6 Hz, H-3eq), 7.20–7.34 (4H, m, O

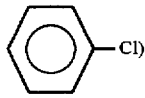—Cl)

Example 30

Synthesis of 3α-[N-[5-acetamido-4,7,8,9-tetra-O-acetyl-3,5-dideoxy-2-O-(4-methoxycarbonylphenyl)-α-D-glycero-D-galacto-2-nonulopyranosonyl] amino] cholestane (the α-isomer of compound No. 117 in Table 1).

To a suspension of 60% sodium hydride (24 mg, 0.60 mmol) in dried dimethylformamide (5 ml), methyl 4-hydroxybenzoate (0.6 mg, 0.60 mmol) was added. After the mixture was stirred at room temperature for 30 minutes, a solution of the compound (515 mg, 0.60 mmol) which was obtained in Synthetic example 2 in dried dimethylformamide (5 ml) was added dropwise over 20 minutes under ice cooling. After stirring at room temperature for 30 minutes, ethyl acetate was added and the reaction mixture was washed with water and dried over anhydrous magnesium sulfate. The solvent was evaporated under reduced pressure and the resulting syrup was purified by silica gel column chromatography [Merck silica gel 60, eluent: chloroform/methanol (100:1)] to obtain the title compound (137 mg, yield=23.5%).

¹H-NMR (CDCl₃) δ(ppm): 0.60 (3H, s, 18'-CH₃), 0.70 (3H, s, 19'-CH₃), 0.82–0.89 (9H, 21'-CH₃, 26'-CH₃, 27'-CH₃), 1.89, 1.98, 2.01, 2.04, 2.10 (15H, s×5, Ac), 2.42 (1H, dd, J=5.3 Hz, 13.2 Hz, H-3eq), 3.87 (3H, s, COOCH₃), 3.96 (1H, m, H-3'), 4.00–4.16 (2H, m, H-5, 9), 5.23–5.44 (4H, m, H-4, 7, 8, AcNH), 6.62 (1H, d, J=7.3 Hz, NH), 7.18 (2H, m, O

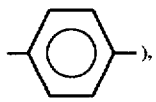), 7.98 (2H, m, O

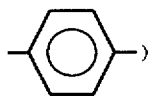)

Example 31

Synthesis of 3α-[N-[5-acetamido-3,5-dideoxy-2-O-(4-methoxycarbonylphenyl)-α-D-glycero-D-galacto-2-nonulopyranosonyl] amino] cholestane (the α-isomer of compound No. 118 in Table 1).

The title compound (85.6 mg, yield=84.7%), was obtained by using the compound (122 mg, 0.12 mmol) which was made in Example 30, in a procedure similar to that described in Example 9.

m.p. 173°–177° C.

IR (KBr) (cm⁻¹) 3400, 2950, 2860, 1730, 1660, 1610

¹H-NMR (CD₃OD) δ(ppm): 0.68 (3H, s, 18'-CH₃), 0.73 (3H, s, 19'-CH₃), 0.91–0.99 (9H, 21'-CH₃, 26'-CH₃, 27'-CH₃), 2.06 (3H, s, Ac), 3.15 (1H, dd, J=4.5 Hz, 12.6 Hz, H-3eq), 3.91 (3H, s, COOCH₃), 7.34 (2H, m, O

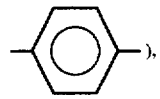), 8.02 (2H, m, O

)

Example 32

Synthesis of sodium 3α-[N-[5-acetamido-3,5-dideoxy-2-O-[4-carboxyphenyl)-α-D-glycero-D-galacto-2-nonulopyranosonyl] amino] cholestane (the sodium salt of the α-isomer of compound No. 114 in Table 1).

The title compound (8.2 mg, yield=12.1%) was obtained by using the compound (66.9 mg, 0.082 mmol) which was made in Example 31, in a procedure similar to that described in Example 14.

m.p. 200°–220° C. (decomposition)

IR (KBr) (cm⁻¹) 3420, 2940, 2860, 1660, 1600

¹H-NMR (CD₃OD) δ(ppm): 0.69 (3H, s, 18'-CH₃), 0.75 (3H, s, 19'-CH₃), 0.91–0.98 (9H, 21'-CH₃, 26'-CH₃, 27'-CH₃), 2.06 (3H, s, Ac), 3.12 (1H, dd, J=4.5 Hz, 12.6 Hz, H-3eq), 7.28 (2H, m, O

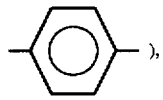), 7.98 (2H, m, O

)

Example 33

Synthesis of 3α-[N-(5-acetamido-4,7,8,9-tetra-O-acetyl-3,5-dideoxy-2-O-methyl-α-D-glycero-D-galacto-2-nonulopyranosonyl) amino]-5-cholestene (the α-isomer of compound No. 231 in Table 1).

The title compound (1.21 g, yield=81%) was obtained by using the compound (855 mg, 1.74 mmol) which was made in Synthetic example 4, and 3 α-amino-5-cholestene (1.01 g, 2.61 mmol), in a procedure similar to that described in Example 2.

IR (KBr) (cm⁻¹) 3420, 2940, 1750, 1680

¹H-NMR (CDCl₃) δ(ppm): 0.68 (3H, s, 18'-CH₃), 0.85–1.02 (12H, 19'-CH₃, 21'-CH₃, 26'-CH₃, 27'-CH₃), 1.89, 2.02, 2.03, 2.08, 2.12 (15H, s×5, Ac), 2.57 (1H, d, J=13.7 Hz, H-7'), 3.36 (3H, s, OCH₃), 4.03 (1H, m, H-3'), 4.06 (1H, dd, J=5.8 Hz, 12.3 Hz, H-9), 4.12 (1H, q, J=10.4 Hz, H-5), 4.28 (1H, dd, J=2.3 Hz, 12.3 Hz, H-9), 4.75 (1H, dd, J=2.0 Hz, 10.7 Hz, H-6), 5.22–5.38 (5H, m, H-4, 7, 8, 6', NH), 6.48 (1H, d, J=7.6 Hz, NH)

Example 34

Synthesis of 3α-[N-[5-acetamido-3,5-dideoxy-2-O-methyl-α-D-glycero-D-galacto-2-nonulopyranosonyl)amino]-5-cholestene (the α-isomer of compound No. 234 in Table 1).

The title compound (405 mg, yield=84%) was obtained by using the compound (597 mg, 0.695 mmol) which was synthesized in Example 33, in a procedure similar to that described in Example 3.

m.p. 288°–290° C. (decomposition)

IR (KBr) (cm$^{-1}$) 3400, 3300, 2950, 1670

$^1$H-NMR [DMSO-D$_6$-CD$_3$OD (1:1)] δ(ppm): 0.61 (3H, s, 18'-CH$_3$), 0.78–0.94 (12H, 19'-CH$_3$, 21'-CH$_3$, 26'-CH$_3$, 27'-CH$_3$), 1.86 (3H, s, Ac), 2.66 (1H, dd, J=4.3 Hz, 12.6 Hz, H-3eq), 3.14 (3H, s, OCH$_3$), 3.66 (1H, dd, J=2.5 Hz, 10.8 Hz, H-6), 3.84 (1H, m, H-3'), 5.17 (1H, m, H-6')

Synthetic Example 6

Synthesis of 3β-[N-(5-acetamido-2,4,7,8,9-penta-O-acetyl-3,5-dideoxy-β-D-glycero-D-galacto-2-nonulopyranosonyl) amino] cholestane [compound (IV) wherein R' is 3β-cholestene, R$^2$ is hydrogen and R$^{4"}$ is acetyl].

The title compound (590 mg, yield=68.3%) was obtained by using 5-acetamido-2,4,7,8,9-penta-O-acetyl-3,5-dideoxy-β-D-glycero-D-galacto-2-nonulopyranosonic acid (505 mg, 0.97 mmol) and 3β-aminocholestane hydrochloride (460 mg, 1.08 mmol), in a procedure similar to that described in Synthetic example 1.

$^1$H-NMR (CDCl$_3$) δ(ppm): 0.62 (3H, s, 18'-CH$_3$), 0.80–0.89 (12H, 19'-CH$_3$, 21'-CH$_3$, 26'-CH$_3$, 27'-CH$_3$), 1.87, 2.00, 2.03, 2.05, 2.09, 2.13 (18H, s×6, Ac), 2.60 (1H, dd, J=5.0 Hz, 13.6 Hz, H-3eq), 3.69 (1H, m, H-3'), 3.98–4.14 (3H, m, H-5, 6, 9), 4.37 (1H, dd, J=2.6 Hz, 12.5 Hz, H-9), 5.08 (1H, m, H-8), 5.19–5.33 (2H, m, H-4, 7), 5.44 (1H, d, J=9.3 Hz, AcN$\underline{H}$), 6.41 (1H, d, J=8.6 Hz, NH)

Example 35

Synthesis of 3β-[N-(5-acetamido-4,7,8,9-tetra-O-acetyl-3,5-dideoxy-2-O-methyl-α-D-glycero-D-galacto-2-nonulopyranosonyl) amino] cholestane (the β-isomer of compound No. 1 in Table 1).

The compound (558 mg, 0.63 mmol) which was obtained in Synthetic example 6 was dissolved in acetyl chloride (20 ml) which was saturated with hydrogen chloride gas and the vessel wherein the reaction mixture was placed was tightly stoppered and allowed to stand at room temperature for 12 hours. After the completion of the reaction, the solvent was evaporated under reduced pressure and subsequently the residue was subjected to azeotropic distillation with benzene to obtain 3β-[N-(5-acetamido-4,7,8,9-tetra-O-acetyl-2-chloro-2, 3,5-trideoxy-β-D-glycero-D-galacto-2-nonulopyranosonyl) amino] cholestane as an oil.

The oil was dissolved in dried benzene (15 ml) and anhydrous calcium sulfate (1.8 g) was added. The mixture was stirred at room temperature for 25 minutes and subsequently methanol (3.0 ml, 74.0 mmol) was added. The mixture was stirred for 40 minutes and then a mixed solution of silver trifluoromethanesulfonate (230 mg, 0.90 mmol) and 2,4,6-trimethylpyridine (0.1 ml, 0.76 mmol) in nitromethane (2 ml) and diethyl ether (3 ml) was added under ice cooling and light shading. After stirring at room temperature for 16 hours, chloroform was added and the mixture was filtered through celite. The filtrate was washed with 0.2N aqueous solution of sodium thiosulfate, 0.2N hydrochloric acid, water, saturated aqueous solution of sodium hydrogen carbonate and water, and dried over anhydrous magnesium sulfate. The solvent was evaporated under reduced pressure and the resulting syrup was purified twice by silica gel column chromatography [Merck silica gel 60, eluent: chloroform/methanol (100:1) (first time) and ethyl acetate (second time)] and solidified by trituration with methanol to obtain the title compound (247 mg, yield=45.7%).

m.p. 158°–162° C.

$^1$H-NMR (CDCl$_3$) δ(ppm): 0.61 (3H, s, 18'-CH$_3$), 0.77–0.88 (12H, 19'-CH$_3$, 21'-CH$_3$, 26'-CH$_3$, 27'-CH$_3$), 1.85, 1.99, 2.01, 2.05, 2.11 (15H, s×5, Ac), 2.30 (1H, dd, J=5.6 Hz, 13.1 Hz, H-3eq), 3.36 (3H, s, OCH$_3$), 3.67 (1H, m, H-3'), 3.92 (1H, dd, J=7.0 Hz, 12.2 Hz, H-9), 4.06–4.19 (2H, m, H-5, 6), 4.59 (1H, m, H-9), 5.19–5.36 (4H, m, H-4, 7, 8, AcN$\underline{H}$), 6.73 (1H, d, J=8.6 Hz, NH)

Example 36

Synthesis of 3β-[N-(5-acetamido-3,5-dideoxy-2-O-methyl-α-D-glycero-D-galacto-2-nonulopyranosonyl) amino] cholestane (the β-isomer of compound No. 4 in Table 1).

The title compound (154 mg, yield=78.2%) was obtained by using the compound (245 mg, 0.28 mmol) which was made in Example 35, in a procedure similar to that described in Example 3.

m.p. 286°–295° C. (decomposition)

IR (KBr) (cm$^{-1}$) 3450, 3330, 2930, 2870, 2850, 1670, 1620

$^1$H-NMR [CDCl$_3$—CD$_3$OD (1:1)] δ(ppm): 0.69 (3H, s, 18'-CH$_3$), 0.85–0.95 (12H, 19'-CH$_3$, 21'-CH$_3$, 26'-CH$_3$, 27'-CH$_3$), 2.04 (3H, s, Ac), 2.86 (1H, dd, J=4.4 Hz, 12.7 Hz, H-3eq), 3.34 (3H, s, OCH$_3$)

Synthetic Example 7

Synthesis of 3β-methylaminocholestane

The title compound (1.01 g, yield=73%) was obtained by using 3β-aminocholestane (1.33 g, 3.42 mmol), in procedure similar to that described in Synthetic example 5.

m.p. 77°–79° C.

IR (KBr) (cm$^{-1}$) 3430, 2930, 1470

$^1$H-NMR (CDCl$_3$) δ(ppm): 0.64 (3H, s, 18-CH$_3$), 077 (3H, s, 19-CH$_3$), 0.84–0.91 (9H, 21-CH$_3$, 26-CH$_3$, 27-CH$_3$), 2.33 (1H, m, H-3), 2.42 (3H, s, N—CH$_3$)

Example 37

Synthesis of 3β-[N-(5-acetamido-4,7,8,9-tetra-O-acetyl-3,5-dideoxy-2-O-methyl-α-D-glycero-D-galacto-2-nonulopyranosonyl)-N-methylamino] cholestane (the β-isomer of compound No. 5 in Table 1).

The title compound (621 mg, yield=77%) was obtained by using the compound (450 mg, 0.916 mmol) which was synthesized in Synthetic example 4 and the 3β-N-methylaminocholestane (368 mg, 0.916 mmol) which was synthesized in Synthetic example 7, in a procedure similar to that described in Example 4.

IR (KBr) (cm$^{-1}$) 3380, 2940, 1750, 1650

$^1$H-NMR (CDCl$_3$) δ(ppm): 0.65 (3H, s, 18'-CH$_3$), 0.80–0.91 (12H, 19'-CH$_3$, 21'-CH$_3$, 26'-CH$_3$, 27'-H$_3$), 1.88, 2.02, 2.04, 2.11, 2.15 (15H, H, s×5, Ac), 2.30, 2.53 (1H <1:3>, dd×2, J=4.4 Hz, 12.4 Hz, H-3eq), 2.81, 3.04 (3H <1:3>, s×2, N—CH$_3$), 3.32, 3.33 (3H, <1:3>, s×2, O—CH$_3$), 4.85, 5.07 (1H, <1:3>, ddd×2, J=4.4 Hz, 12.4 Hz, 12.4 Hz, H-4), 5.16 (1H, d, J=10.2 Hz, NH)

Example 38

Synthesis of 3β-[N-(5-acetamido-3,5-dideoxy-2-O-methyl-α-D-glycero-D-galacto-2-nonulopyranosonyl)-N-methylamino] cholestane (the β-isomer of compound No. 6 in Table 1).

The title compound (213 mg, yield=47%) was obtained by using the compound (558 mg, 0.638 mmol) which was synthesized in Example 37, in a procedure similar to that described in Example 3.

m.p. 270°–281° C. (decomposition)

IR (KBr) (cm⁻¹) 3400, 2930, 1630

¹H-NMR [CDCl₃—CD₃OD (1:1)] δ(ppm): 0.67 (3H, s, 18'-CH₃), 0.84–0.93 (12H, 19'-CH₃, 21'-CH₃, 26'-CH₃, 27'-CH₃), 2.03 (3H, s, Ac), 2.47, 2.66 (1H <1:3>, dd×2, J=4.7 Hz, 12.8 Hz, H-3eq), 2.85, 3.15 (3H <1:3>, s×2, N—CH₃), 3.34, 3.35 (3H <1:3>, s×2, O—CH₃), 4.26 (1H, m, H-3')

Example 39

Synthesis of 3α-[N-5-acetamido-3,5-dideoxy-2-S-methyl-2-thio-α-D-glycero-D-galacto-2-nonulopyranosonyl) amino] cholestane (the α-isomer of compound No. 252 in Table 2).

To a solution of the compound (500 mg, 0.562 mmol) which was synthesized in Synthetic example 1 and methylthiotrimethylsilane (250 mg, 2.08 mmol) in methylene chloride (6 ml), powder molecular sieve 4 A (100 mg) and the trimethylsilyltrifluoromethanesulfonic acid (109 µl, 0.562 mmol) were added. The mixture was heated at 50° C. for 6 hours. To the resulting mixture was added aqueous solution of sodium carbonate (1 mol/l, 10 ml) and the resulting mixture was stirred for five minutes, then chloroform (10 ml) was added and separated. The chloroform layer was washed with water, and dried over anhydrous magnesium sulfate. The solvent was evaporated under reduced pressure and the resulting syrup was purified by silica gel column chromatography [Merck silica gel 60, eluent: chloroform/methanol (100:1)] to obtain the mixture (276 mg, yield=55%) of 3α-[N-(5-acetamido-4,7,8,9-tetra-O-acetyl-3,5-dideoxy-2-S-methyl-2-thio-α-D-glycero-D-galacto-2-nonulopyranosonyl) amino] cholestane and the β-anomer of the 2-position of sialic acid (ratio=about 3:2). The mixture (234 mg, 0.267 mmol) was dissolved in methanol (10 ml) and 4.9N solution of sodium methoxide in methanol (0.05 ml, 0.25 mmol) was added. The mixture was stirred at room temperature for 3 hours. The precipitated solid was filtered off to obtain the title compound (14.8 mg, yield=7.8%).

m.p. 250°–253° C. (decomposition)

IR (KBr) (cm⁻¹) 3420, 2930, 2870, 1655

¹H-NMR [CDCl₃—CD₃OD (1:1)] δ(ppm): 0.67 (3H, s, 18'-CH₃), 0.82–0.93 (12H, 19'-CH₃, 21'-CH₃, 26'-CH₃, 27'-CH₃), 2.03 (3H, s, Ac), 2.21 (3H, s, SCH₃), 2.93 (1H, dd, J=4.3 Hz, 12.8 Hz, H-3eq), 3.99 (1H, m, H-3')

Example 40

Synthesis of 3α-[N-(5-acetamido-3,5-dideoxy-2-S-hexyl-2-thio-α-D-glycero-D-galacto-2-nonulopyranosonyl) amino] cholestane (the α-isomer of compound No. 256 in Table 2) and 3α-[N-(5-acetamido-3,5-dideoxy-2-S-hexyl-2-thio-β-D-glycero-D-galacto-2-nonulopyranosonyl) amino] cholestane (the α isomer of compound No. 291 in Table 4).

The compound (600 mg, 0.675 mmol) which was synthesized in Synthetic example 1 and n-hexanethiol (239 mg, 2.02 mmol) were dissolved in methylene chloride (6 ml) and powder molecular sieve 4 A was added. The mixture was stirred for 1 hour and boron trifluoride-ether complex (0.25 ml) was added, then stirred at room temperature for 20 hours. The reaction mixture was filtered through celite. The filtrate was washed with saturated aqueous solution of sodium hydrogen carbonate and saturated saline solution, and dried over anhydrous magnesium sulfate. After the solvent was evaporated under reduced pressure, and the resulting syrup was purified by silica gel column chromatography [Merck silica gel 60, eluent: chloroform/methanol (100:1)] to obtain the mixture (ratio: about 1:1) (558 mg, yield=88%) of 3α-[N-(5-acetamido-4,7,8,9-tetra-O-acetyl-3,5-dideoxy-2-S-hexyl-2-thio-α-D-glycero-D-galacto-2-nonulopyranosonyl) amino] cholestane and 3α-[N-(5-acetamido-4,7,8,9-tetra-O-acetyl-3,5-dideoxy-2-S-hexyl-2-thio-β-D-glycero-D-galacto-2-nonulopyranosonyl) amino] cholestane. The mixture (474 mg, 0.500 mmol) was dissolved in methanol (5 ml) and 4.9N solution of sodium methoxide in methanol (0.10 ml, 0.49 mmol) was added, then stirred at room temperature for 2 hours. The reaction mixture was neutralized by addition of Dowex (50 W×8, H+) resin, then concentrated under reduced pressure, and to the residue was added methanol (1 ml). The precipitated solid was filtered off and recrystallized from methanol to obtain one of the title compounds (the α-isomer of compound No. 256 in Table 2) (50 mg, yield=13%).

Further, the filtrate was purified by column chromatography (ODS MCIGEL, eluent: water/methanol), then evaporated under reduced pressure. The resulting solid was triturated with hexane-ether to obtain the other compound of the title compounds (the α-isomer of compound No. 291 in Table 4) (39 mg, yield=11%).

The α-isomer of compound No. 256 in Table 2 m.p. 151°–156° C. (decomposition)

IR (KBr) (cm⁻¹) 3360, 2930, 1635

¹H-NMR (CD₃OD) δ(ppm): 0.74 (3H, s, 18'-CH₃), 0.89–0.98 (15H, 19'-CH₃, 21'-CH₃, 26'-CH₃, 27'-CH₃, SCH₂CH₂ CH₂CH₂CH₂CH₃), 2.03 (3H, s, Ac), 2.68, 2.89 (2H, m×2, SCH₂CH₂CH₂CH₂CH₂CH₃), 2.96 (1H, dd, J=4.4 Hz, 12.5 Hz, H-3eq), 3.97 (1H, m, H-3')

The α-isomer of compound No. 291 in Table 4 m.p. 125°–135° C. (decomposition)

IR (KBr) (cm⁻¹) 3400, 2920, 1660

¹H-NMR (CD₃OD) δ(ppm): 0.74 (3H, s, 18'-CH₃), 0.91–0.98 (15H, 19'-CH₃, 21'-CH₃, 26'-CH₃, 27'-CH₃, SCH₂CH₂ CH₂CH₂CH₂CH₃), 2.07 (3H, s, Ac), 2.47, 2.72 (2H, m×2, SCH₂CH₂ CH₂CH₂CH₂CH₃), 2.50 (1H, dd, J=4.7 Hz, 13.5 Hz, H-3eq), 4.07 (1H, m, H-3') 4.12 (1H, m, H-4), 4.27 (1H, d, J=10.5 Hz, H-6)

Example 41

Synthesis of 3α-[N-(5-acetoamido-4,7,8,9-tetra-O-acetyl-3,5-dideoxy-2-S-phenyl-2-thio-α-D-glycero-D-galacto-2-nonulopyranosonyl) amino] cholestane (the α-isomer of compound No. 259 in Table 2).

The compound (385 mg, 0.44 mmol) which was obtained in Synthetic example 2 was dissolved in dried acetonitrile (10 ml) and powder molecular sieve 4 A (540 mg) was added. The mixture was stirred at room temperature for 20 minutes and subsequently sodium thiophenoxide (70 mg, 0.53 mmol) was added under ice cooling, and then silver carbonate (150 mg, 0.54 mmol) was added under light shading. The resulting mixture was stirred for 2 hours. To the reaction mixture was added chloroform and then filtered through celite. The filtrate was concentrated and the resulting syrup was purified by silica gel column chromatography [Merck silica gel 60, eluent: chloroform/methanol (100:1)] to obtain the title compound (95.0 mg, yield=22.7%).

$^1$H-NMR (CDCl$_3$) δ(ppm): 0.62 (3H, s, 18'-CH$_3$), 0.77–0.92 (12H, 19'-CH$_3$, 21'-CH$_3$, 26'-CH$_3$, 27'-CH$_3$), 1.80, 1.93, 2.07, 2.10, 2.13 (15H, s×5, Ac), 2.74 (1H, dd, J=4.7 Hz, 12.8 Hz, H-3eq), 3.77–4.11 (4H, m, H-3', 5, 6, 9), 4.91 (1H, dd, J=2.4 Hz, 12.2 Hz, H-9), 5.02 (1H, m, H-4), 5.19–5.30 (3H, H-7, 8, AcNH), 6.88 (1H, d, J=6.8 Hz, NH), 7.29–7.57 (5H, m,

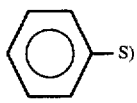

Example 42

Synthesis of 3α-[N-(5-acetamido-3,5-dideoxy-2-S-phenyl-2-thio-α-D-glycero-D-galacto-2-nonulopyranosonyl) amino] cholestane (the α-isomer of compound No. 260 in Table 2).

The title compound (21.3 mg, yield=27.3%) was obtained by using the compound (95 mg, 0.10 mmol) which was made in Example 41, in a procedure similar to that described in Example 9.

m.p. 222°–227° C.

IR (KBr) (cm$^{-1}$) 3400, 2930, 2860, 1640

$^1$H-NMR (CD$_3$OD) δ(ppm): 0.71 (3H, s, 18'-CH$_3$), 0.78 (3H, s, 19'-CH$_3$), 0.91–0.98 (9H, 21'-CH$_3$, 26'-CH$_3$, 27'-CH$_3$), 2.03 (3H, s, Ac), 3.02 (1H, dd, J=4.4 Hz, 12.5 Hz, H-3eq), 7.36–7.69 (5H, m,

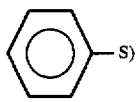

Synthetic Example 8

Synthesis of benzyl 5-acetamido-4,7,8,9-tetra-O-acetyl-3,5-dideoxy-2-O-methyl-β-D-glycero-D-galacto-2-nonulopyranosonate [compound (X-β) wherein R$^3$ is methyl and R$^{4'}$ is acetyl].

To methyl 5-acetamido-3,5-dideoxy-2-O-methyl-β-D-glycero-D-galacto-2-nonulopyranosonate (3.06 g, 9.07 mmol) was added 0.1N aqueous solution of sodium hydroxide (100 ml, 10.0 mmol) under ice cooling and then the mixture was stirred at room temperature for 22 hours. The reaction mixture was neutralized by addition of Dowex (50 W×8, H+) resin. The resin was filtered off and the filtrate was concentrated to obtain sodium 5-acetamido-3,5-dideoxy-2-O-methyl-β-D-glycero-D-galacto-2-nonulopyranosonate as an oil.

The oil was suspended in dried dimethylformamide (50 ml) and benzyl bromide (1.5 ml, 12.6 mmol) was added. The mixture was stirred at room temperature for 13 hours. After the completion of the reaction, the solvent was evaporated under reduced pressure to obtain an oil containing benzyl 5-acetamido-3,5-dideoxy-2-O-methyl-β-D-glycero-D-galacto-2-nonulopyranosonate.

The oil was dissolved in pyridine (30 ml) and acetic anhydride (18 ml, 0.19 mmol) was added under ice cooling.

Subsequently, the resulting mixture was stirred at room temperature for 17 hours. After the completion of the reaction, methanol (10 ml, 0.25 ml) was added under ice cooling and the mixture was stirred for 1 hour. The solvent was evaporated under reduced pressure, and to the resulting syrup was added ethyl acetate. The mixture was washed with 0.5N hydrochloric acid, water, saturated aqueous solution of sodium hydrogen carbonate and water, and dried over anhydrous magnesium sulfate. The solvent was evaporated under reduced pressure and the resulting syrup was purified by silica gel column chromatography [Merck silica gel 60, eluent: chloroform/methanol (100:1 to 500:7.5)] to obtain the title compound (4.91 g, yield=93.0%).

IR (KBr) (cm$^{-1}$) 3380, 3270, 3070, 2970, 1750, 1660

$^1$H-NMR (CDCl$_3$) δ(ppm): 1.84, 1.97, 2.02, 2.11 (15H, s×5, Ac), 2.40 (1H, dd, J=5.0 Hz, 12.9 Hz, H-3eq), 3.20 (3H, s, OCH$_3$), 3.90 (1H, dd, J=2.2 Hz, 10.5 Hz, H-6), 4.02–4.15 (2H, m, H-5, 9), 4.74 (1H, dd, J=2.5 Hz, 12.4 Hz, H-9), 5.14–5.27 (4H, m, H-4, 8,

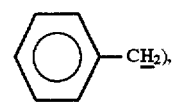

5.37 (1H, m, H-7), 5.48 (1H, d, J=10.1 Hz, AcNH), 7.30–7.35 (5H, m,

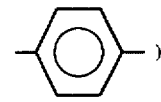

Synthetic Example 9

Synthesis of 5-acetamido-4,7,8,9-tetra-O-acetyl-3,5-dideoxy-2-O-methyl-β-D-glycero-D-galacto-2-nonulopyranosonic acid [compound (XI-β) wherein R$^3$ is methyl and R$^{4'}$ is acetyl].

The compound (626 mg, 1.08 mmol) which was obtained in Synthetic example 8 was dissolved in methanol (10 ml) and 5% palladium-carbon (130 mg) was added. The mixture was stirred in an atmosphere of hydrogen at room temperature for 21 hours. After the completion of the reaction, the catalyst was filtered off and the filtrate was concentrated to obtain the title compound (481 mg, yield=90.9%).

IR (KBr) (cm$^{-1}$) 3370, 3080, 2980, 2630, 1750, 1660

$^1$H-NMR (CD$_3$OD) δ(ppm): 1.82 (1H, dd, J=11.8 Hz, 12.8 Hz, H-3ax), 1.89, 2.01, 2.04, 2.08, 2.15 (15H, s×5, Ac), 2.46 (1H, dd, J=5.0 Hz, 12.9 Hz, H-3eq), 3.33 (3H, s, OCH$_3$), 3.96–4.10 (2H, m, H-5, 6), 4.19 (1H, dd, J=6.7 Hz, 12.5 Hz, H-9), 4.73 (1H, dd, J=2.5 Hz, 12.4 Hz, H-9), 5.23 (1H, m, H-4), 5.35 (1H, m, H-8), 5.45 (1H, m, H-7)

Example 43

Synthesis of 3α-[N-(5-acetamido-4,7,8,9-tetra-O-acetyl-3,5-dideoxy-2-O-methyl-β-D-glycero-D-galacto-2-nonulopyranosonyl) amino] cholestane (the α-isomer of compound No. 265 in Table 3).

The title compound (603 mg, yield=71.5%) was obtained by using the compound (481 mg, 0.98 mmol) which was prepared in Synthetic example 9, and 3α-amino-cholestane hydrochloride (471 mg, 1.11 mmol), in a procedure similar to that described in Synthetic example 1.

$^1$H-NMR (CDCl$_3$) δ(ppm): 0.62 (3H, s, 18'-CH$_3$), 0.79–0.88 (12H, 19'-CH$_3$, 21'-CH$_3$, 26'-CH$_3$, 27'-CH$_3$), 1.89, 1.99, 2.00, 2.07, 2.14 (15H, s×5, Ac), 2.49 (1H, dd, J=4.9 Hz, 13.2 Hz, H-3eq), 3.16 (3H, s, OCH₃), 3.92 (1H, dd, J=1.7 Hz, 10.6 Hz, H-6), 4.02–4.11 (3H, m, H-3', 5, 9), 4.41 (1H, dd, J=2.7 Hz, 12.3 Hz, H-9), 5.17–5.29 (2H, m, H-4, 8), 5.34 (1H, m, H-7), 5.48 (1H, d, J=9.9 Hz, AcNH), 6.99 (1H, d, J=7.9 Hz, NH)

Example 44

Synthesis of 3α-[N-(5-acetamido-3,5-dideoxy-2-O-methyl-β-D-glycero-D-galacto-2-nonulopyranosonyl) amino] cholestane (the α-isomer of compound No. 268 in Table 3).

The title compound (197 mg, yield=81.4%) was obtained by using the compound (301 mg, 0.35 mmol) which was made in Example 43, in a procedure similar to that described in Example 3.

m.p. 244°–248° C.

IR (KBr) (cm⁻¹) 3410, 2930, 2870, 1660

¹H-NMR [CDCl₃—CD₃OD (1:1)] δ(ppm): 0.68 (3H, s, 18'-CH₃), 0.84–0.94 (12H, 19'-CH₃, 21'-CH₃, 26'-CH₃, 27'-CH₃), 2.06 (3H, s, Ac), 2.43 (1H, dd, J=4.8 Hz, 13.0 Hz, H-3eq), 3.23 (3H, s, OCH₃), 4.00–4.05 (2H, m, H-3', 4)

Example 45

Synthesis of 3α-[N-(5-acetamido-3,5-dideoxy-2-O-benzyl-β-D-glycero-D-galacto-2-nonulopyranosonyl) amino] cholestane (the α-isomer of compound No. 281 in Table 3).

The title compound (11.0 mg, yield=40.6%) was obtained by using the α-isomer of compound No. 280 in Table 3 (33.0 mg, 0.035 mmol) which was made in example 10, in a procedure similar to that described in Example 9.

m.p.191°–197° C.

IR (KBr) (cm⁻¹) 3420, 2940, 2860, 1660

¹H-NMR (CD₃OD) δ(ppm): 0.73 (3H, s, 18'-CH₃), 0.90–0.99 (12H, 19'-CH₃, 21'-CH₃, 26'-CH₃, 27'-CH₃), 2.06 (3H, s, Ac), 2.52 (1H, dd, J=4.8 Hz, 12.9 Hz, H-3eq), 7.29–7.49 (5H, m,

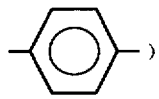

)

Example 46

Synthesis of 3β-[N-(5-acetamido-4,7,8,9-tetra-O-acetyl-3,5-dideoxy-2-O-methyl-β-D-glycero-D-galacto-2-nonulopyranosonyl) amino] cholestane (the β-isomer of compound No. 265 in Table 3).

The title compound (492 mg, yield=53.4%) was obtained by using the compound (526 mg, 1.07 mmol) which was made in Synthetic example 9, and 3β-aminocholestane hydrochloride (460 mg, 1.08 mmol), in a procedure similar to that described in Synthetic example 1.

¹H-NMR (CDCl₃) δ(ppm): 0.62 (3H, s, 18'-CH₃), 0.80–0.89 (12H, 19'-CH₃, 21'-CH₃, 26'-CH₃, 27'-CH₃), 1.86, 1.99, 2.02, 2.07, 2.14 (15H, s×5, Ac), 2.55 (1H, dd, J=4.9 Hz, 13.3 Hz, H-3eq), 3.17 (3H, s, OCH₃), 3.74 (1H, m, H-3'), 3.93–4.15 (3H, m, H-5, 6, 9), 4.43 (1H, m, H-9), 5.15–5.30 (3H, m, H-4, 7, 8), 5.36 (1H, d, J=9.9 Hz, AcN H), 6.63 (1H, d, J=8.4 Hz, NH)

Example 47

Synthesis of 3β-[N-(5-acetamido-3,5-dideoxy-2-O-methyl-β-D-glycero-D-galacto-2-nonulopyranosonyl) amino] cholestane (the β-isomer of compound No. 268 in Table 3).

The title compound (178 mg, yield=44.9%) was obtained by using the compound (492 mg, 0.57 mmol) which was made in Example 46, in a procedure similar to that described in Example 3.

m.p. 222°–240° C. (decomposition)

IR (KBr) (cm⁻¹) 3410, 2930, 2870, 1660

¹H-NMR [CDCl₃—CD₃OD (1:1)] δ(ppm): 0.68 (3H, s, 18'-CH₃), 0.86–0.94 (12H, 19'-CH₃, 21'-CH₃, 26'-CH₃, 27'-CH₃), 2.06 (3H, s, Ac), 2.41 (1H, dd, J=4.9 Hz, 13 Hz, H-3eq), 3.21 (3H, s, OCH₃), 4.02 (1H, m, H-4)

Example 48

Synthesis of 3α-[N-(5-acetamido-3,5-dideoxy-2-S-phenyl-2-thio-β-D-glycero-D-galacto-2-nonulopyranosonyl) amino] cholestane (the α-isomer of compound No. 295 in Table 4).

To a solution of the compound (400 mg, 0.450 mmol) which was synthesized in Synthetic example 1 and thiophenol (148 mg, 1.35 mmol) dissolved in methylene chloride (5 ml), powder molecular sieve 4 A was added and stirred for 1 hour. Boron trifluoride ether complex (0.17 ml) was added and the mixture was stirred at room temperature for 2 hours. The reaction mixture was filtered through Celite and the filtrate was washed with saturated aqueous solution of sodium hydrogen carbonate and saturated saline solution, and dried over anhydrous magnesium sulfate. The solvent was distilled away and the resulting syrup was purified by silica gel column chromatography [Merck silica gel 60, eluent: chloroform/methanol (100:1)] to obtain a mixture (ratio=about 1:1) (303 mg, yield=71%) of 3α-[N-(5-acetamido-4,7,8,9-tetra-O-acetyl-3,5-dideoxy-2-S-phenyl-2-thio-β-D-glycero-D-galacto-2-nonulopyranosonyl)amino] cholestane and the α-anomer of the 2-position of sialic acid. This mixture (261 mg, 0.278 mmol) was dissolved in methanol (3 ml) and 4.9N solution of sodium methoxide in methanol (0.06 ml, 0.29 mmol) was added. The resulting mixture was stirred at room temperature for 1 hour and neutralized with Dowex (50 W×8, H+) resin. The solvent was evaporated under reduced pressure and the resulting syrup was purified by silica gel column chromatography [Merck silica gel, eluent: chloroform/methanol (10:1 to 5:1) and then ODS MCIGEL, eluent: water/methanol] to obtain the title compound (76 mg, yield=35%).

m.p.148°–155° C. (decomposition)

IR (KBr) (cm⁻¹) 3430, 2950, 1660

¹H-NMR (CD₃OD) δ(ppm): 0.71 (3H, s, 18'-CH₃), 0.75 (3H, s, 19'-CH₃), 0.91–1.00 (9H, 21'-CH₃, 26'-CH₃, 27'-CH₃), 1.89 (1H, dd, J=11.7 Hz, 13.5 Hz, H-3ax), 2.10 (3H, s, Ac), 2.75 (1H, dd, J=4.6 Hz, 13.5 Hz, H-3eq), 4.16 (1H, dt, J=11.7 Hz, 4.6 Hz, H-4), 4.57 (1H, d, J=10.5 Hz, H-6), 7.37, 7.74 (5H, m, C₆H₅)

Synthetic Example 10

Synthesis of methyl 5-acetamido-4,7,8,9-tetra-O-acetyl-3,5-dideoxy-2-O-methyl-α-D-glycero-D-galacto-2-nonulopyranosonate [compound (XIX) wherein R³ is methyl, R³' is methyl and R⁴ is acetyl].

The title compound (9.50 g, yield=92.2%) was obtained by using methyl 5-acetamido-4,7,8,9-tetra-O-acetyl-2-chloro-2,3,5-trideoxy-β-D-glycero-D-galacto-2-nonulopyranosonate (10.4 g, 20.4 mmol) and methanol (83 ml, 2.05 mol), in a procedure similar to that described in Example 1.

¹H-NMR (CDCl₃) δ(ppm): 1.86, 2.00, 2.02, 2.11, 2.13 (15H, s×5, Ac), 2.55 (1H, dd, J=4.6 Hz, 12.8 Hz, H-3eq), 3.30 (3H, s, OCH₃), 3.79 (3H, s, COOCH₃), 4.00–4.13 (3H, m, H-5, 6, 9), 4.29 (1H, dd, J=2.7 Hz, 12.4 Hz, H-9), 4.83 (1H, m, H-4), 5.15 (1H, d, J=9.5 Hz, NH), 5.30 (1H, dd, J=1.8 Hz, 8.4 Hz, H-7), 5.41 (1H, m, H-8)

Synthetic Example 11

Synthesis of methyl 5-acetamido-3,5-dideoxy-2-O-methyl-α-D-glycero-D-galacto-2-nonulopyranosonate [compound (XX) wherein R³ is methyl and R³' is methyl].

To a solution of the compound (9.50 g, 18.8 mmol) which was obtained in Synthetic example 10 in methanol (150 ml), 4.9N solution of sodium methoxide in methanol (0.5 ml, 2.45 mmol) was added under ice cooling, and then, the mixture was stirred for 20 hours. The reaction mixture was neutralized by addition of Dowex (50 W×8, H+) resin and filtered. The filtrate was concentrated to obtain the title compound (5.14 g, yield=81.1%).

m.p.161°–167° C.

IR (KBr) (cm⁻¹) 3460, 3235, 3055, 2920, 1730, 1645

¹H-NMR (CD₃OD) δ(ppm): 1.76 (1H, dd, J=11.7 Hz, 12.8 Hz, H-3ax), 2.04 (3H, s, Ac), 2.70 (1H, dd, J=4.6 Hz, 12.8 Hz, H-3eq), 3.38 (3H,s, OCH₃)

Synthetic Example 12

Synthesis of 5-amino-3,5-dideoxy-2-O-methyl-α-D-glycero-D-galacto-2-nonulopyranosonic acid [compound (XXI) wherein R³ is methyl].

The compound (3.02 g, 8.95 mmol) which was made in Synthetic example 11 was dissolved in water (75 ml). Barium hydroxide 8 hydrate (6.22 g, 19.7 mmol) was added and the mixture was stirred at 90° to 95° C. for 20 hours. The reaction mixture was neutralized by addition of Amberlite (IRC-50, H+) resin and filtered. The filtrate was concentrated to obtain the title compound (2.52 g, yield=100%).

¹H-NMR (CD₃OD—D₂O) δ(ppm): 1.65 (1H, m, H-3ax), 2.80 (1H, m, H-3eq)

Synthetic Example 13

Synthesis of 4,7,8,9-tetra-O-acetyl-5-benzyloxyacetamido-3,5-dideoxy-2-O-methyl-α-D-glycero-D-galacto-2-nonulopyranosonic acid [compound (XXIII) wherein R³ is methyl, R⁴' is acetyl and R¹⁵ is benzyloxyacetyl].

The compound (733 mg, 2.61 mmol) which was obtained in Synthetic example 12 was suspended in methanol (25 ml). Triethylamine (0.36 ml, 2.60 mmol) and benzyloxyacetyl chloride (0.44 ml, 2.79 mmol) were added under ice cooling and the mixture was stirred for 1 hour, and for 20 hours at room temperature. After the completion of the reaction, the solvent was evaporated under reduced pressure and the residue was subjected to azeotropic distillation with benzene to obtain 5-benzyloxyacetamido-3,5-dideoxy-2-O-methyl-α-D-glycero-D-galacto-2-nonulopyranosonic acid.

The resulting acid was suspended in pyridine (35 ml), and 4-dimethylaminopyridine (20 mg, 0.16 mmol) and acetic anhydride (4.0 ml, 42.3 mmol) were added under ice cooling. The reacting mixture was stirred for 3 hours under ice cooling, and further stirred for 18 hours at room temperature. After the completion of the reaction, methanol (5 ml, 0.12 mol) was added under ice cooling and the reaction mixture was stirred for 1 hour. The solvent was evaporated under reduced pressure, and to the resulting syrup was dissolved in chloroform, washed with water and dried over anhydrous magnesium sulfate. The solvent was evaporated under reduced pressure to obtain the title compound (1.24 g, yield=79.5%).

¹H-NMR (CDCl₃) δ(ppm): 1.86–2.15 (13H, H-3ax, Ac×4), 2.68 (1H, dd, J=4.6 Hz, 12.5 Hz, H-3eq), 3.40 (3H, s, OCH₃), 3.86 (2H, m, OCH₂CON), 4.54 (2H, m,

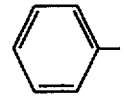

CH₂O), 5.03 (1H, m, H-4), 5.34 (1H, dd, J=2.1 Hz, 8.5 Hz, H-7), 5.47 (1H, m, H-8), 6.39 (1H, d, J=10.5 Hz, NH), 7.28–7.39 (5H, m,

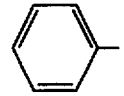

Example 49

Synthesis of 3α-[N-(4,7,8,9-tetra-O-acetyl-5-benzyloxyacetamido-3,5-dideoxy-2-O-methyl-α-D-glycero-D-galacto-2-nonulopyranosonyl) amino] cholestane (the α-isomer of compound No. 382 in Table 5).

The title compound (672 mg, yield=51.7%) was obtained by using the compound (1.24 g, 2.07 mmol), which was made in Synthetic example 13, and 3α-aminocholestane hydrochloride (890 mg, 2.10 mmol), in a procedure similar to that described in Synthetic example 1.

IR (KBr) (cm⁻¹) 3435, 3390 ,2940, 2870, 1750, 1680

¹H-NMR (CDCl₃) δ(ppm): 0.63 (3H, s, 18'-CH₃), 0.77–0.89 (12H, 19'-CH₃, 21'-CH₃, 26'-CH₃, 27'-CH₃), 1.96, 1.99, 2.05, 2.10 (12H, s×4, Ac), 2.23 (1H, dd, J=5.3 Hz, 13.2 Hz, H-3eq), 3.40 (3H, s, OCH₃), 3.85 (2H, m, OCH₂CON), 3.98–4.30 (4H, m, H-3', 5, 9, 9), 4.49–4.64 (3H, m, H-6,

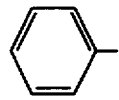

CH₂O), 5.22–5.42 (3H, m, H-4, 7, 8), 6.39 (1H, d, J=10.6 Hz, NH), 6.74 (1H, d, J=7.8 Hz, NH), 7.30–7.40 (5H, m,

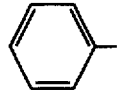

Example 50

Synthesis of 3α-[N-(5-benzyloxyacetamido-3,5-dideoxy-2-O-methyl-α-D-glycero-D-galacto-2-nonulopyronosonyl) amino] cholestane (the α-isomer of compound No. 314 in Table 5).

The title compound (52 mg, yield=30.5%) was obtained by using the compound (206 mg, 0.21 mmol) which was made in Example 49, in a procedure similar to that described in Example 9.

IR (KBr) (cm⁻¹) 3430, 3370, 2935, 2870, 1660

¹H-NMR (CD₃OD) δ(ppm): 0.73 (3H, s, 18'-CH₃), 0.88–0.98 (12H, 19'-CH₃, 21'-CH₃, 26'-CH₃, 27'-CH₃), 2.85 (1H, dd, J=4.3 Hz, 12.8 Hz, H-3eq), 3.39 (3H, s, OCH₃), 4.65 (2H, m,

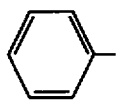

CH₂O), 7.33–7.45 (5H, m,

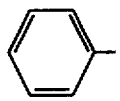

Example 51

Synthesis of 3α-[N-(4,7,8,9-tetra-O-acetyl-3,5-dideoxy-5-hydroxyacetamido-2-O-methyl-α-D-glycero-D-galacto-2-nonulopyranosonyl) amino] cholestane (the α-isomer of compound No. 376 in Table 5).

The compound (410 mg, 0.42 mmol) which was obtained in Example 49 was dissolved in ethanol (20 ml) and palladium black (70 mg) was added. The mixture was stirred in an atmosphere of hydrogen for 10 hours. The catalyst was filtered off and the solvent was evaporated under reduced pressure. The resulting syrup was purified by silica gel column chromatography [Merck silica gel 60, eluent: chloroform/methanol (250:1 to 50:1)] to obtain the title compound (302 mg, yield=81.2%).

IR (KBr) (cm⁻¹) 3385, 2940, 2870, 1750, 1685

¹H-NMR (CDCl₃) δ(ppm): 0.62 (3H, s, 18'-CH₃), 0.77–0.89 (12H, 19'-CH₃, 21'-CH₃, 26'-CH₃, 27'-CH₃), 1.98, 2.00, 2.03, 2.12 (12H, s×4 Ac), 2.22 (1H, dd, J=5.2 Hz, 13.1 Hz, H-3eq), 3.40 (3H, s, OCH₃), 3.95–4.02 (4H, m, HOC$\underline{H}_2$CON, H-3', 9), 4.16 (1H, m, H-5), 4.42 (1H, m, H-9), 4.64 (1H, m, H-6), 5.27–5.30 (2H, m, H-7, 8), 5.40 (1H, m, H-4), 6.80–6.87 (2H, m, NH×2)

Example 52

Synthesis of 3α-[N-(3,5-dideoxy-5-hydroxyacetamido-2-O-methyl-α-D-glycero-D-galacto- 2-nonulopyranosonyl) amino] cholestane (the α-isomer of compound No. 308 in Table 5).

The title compound (86 mg, yield=42.6%) was obtained by using the compound (250 mg, 0.29 mmol), which was given in Example 51, in a procedure similar to that described in Example 3.

IR (KBr) (cm⁻¹) 3425, 3320, 2935, 2870, 1660, 1620

¹H-NMR [CDCl₃—CD₃OD (1:1)] δ(ppm): 0.69 (3H, s, 18'-CH₃), 0.84–0.95 (12H, 19'-CH₃, 21'-CH₃, 26'-CH₃, 27'-CH₃), 2.84 (1H, dd, J=4.4 Hz, 12.9 Hz, H-3eq), 3.39 (3H, s, OCH₃), 4.02 (1H, m, H-3'), 4.07 (2H, s, HOC$\underline{H}_2$CON)

Synthetic Example 14

Synthesis of 4,7,8,9-tetra-O-acetyl-5-benzamido-3,5-dideoxy-2-O-methyl-α-D-glycero-D-galacto-2-nonulopyranosonic acid [compound (XXIII) wherein R³ is methyl, R⁴ is acetyl and R¹⁵ is benzoyl].

The title compound (540 mg, yield=61.0%) was obtained by using the compound (450 mg, 1.60 mmol) which was made in Synthetic example 12 and benzoyl chloride (0.19 ml, 1.64 mmol), in a procedure similar to that described in Synthetic example 13.

¹H-NMR (CDCl₃) δ(ppm): 1.91–2.20 (13H, H-3ax, Ac×4), 2.69 (1H, dd, J=4.6 Hz, 12.5 Hz, H-3eq), 3.43 (3H, s, OCH₃), 5.20 (1H, m, H-4), 5.34 (1H, dd, J=1.8 Hz, 8.0 Hz, H-7), 5.47 (1H, m, H-8), 7.30–7.63 (5H, m,

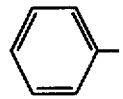

Example 53

Synthesis of 3α-[N-(4,7,8,9-tetra-O-acetyl-5-benzamido-3,5-dideoxy-2-O-methyl-α-D-glycero-D-galacto-2-nonulopyranosonyl) amino] cholestane (the α-isomer of compound 396 in Table 5).

The title compound (351 mg, yield=46.1%) was obtained by using the compound (474 mg, 0.86 mmol) which was made in Synthetic example 14 and 3α-aminocholestane hydrochloride (440 mg, 1.04 mmol), in a procedure similar to that described in Synthetic example 1.

IR (KBr) (cm⁻¹) 3380, 2940, 2870, 1750, 1670

¹H-NMR (CDCl₃) δ(ppm): 0.63 (3H, s, 18'-CH₃), 0.78–0.89 (12H, 19'-CH₃, 21'-CH₃, 26'-CH₃, 27'-CH₃), 1.92, 1.97, 2.03, 2.19 (12H, s×4 Ac), 2.24 (1H, dd, J=5.4 Hz, 13.1 Hz, H-3eq), 3.44 (3H, s, OCH₃), 3.95–4.03 (2H, m, H-3', 9), 4.28–4.41 (2H, m, H-5, 9), 4.64 (1H, m, H-6), 5.23–5.34 (2H, m, H-7, 8), 5.57 (1H, m, H-4), 5.92 (1H, d, J=9.9 Hz, NH), 6.81 (1H, d, J=7.7 Hz, NH), 7.35–7.63(5H, m,

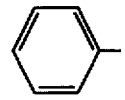

Example 54

Synthesis of 3α-[N-(benzamido-3,5-dideoxy-2-O-methyl-α-D-glycero-D-galacto- 2-nonulopyranosonyl) amino] cholestane (the α-isomer of compound No. 328 in Table 5).

The title compound (156 mg, yield=59.3%) was obtained by using the compound (321 mg, 0.35 mmol) which was made in Example 53, in a procedure similar to that described in Example 3.

m.p. 253°–258° C. (decomposition)

IR (KBr) (cm⁻¹) 3350, 3300, 2950, 2850, 1660, 1630

¹H-NMR [CDCl₃—CD₃OD (1:1)] δ(ppm): 0.69 (3H, s, 18'-CH₃), 0.84–0.94 (12H, 19'-CH₃, 21'-CH₃, 26'-CH₃, 27'-CH₃), 2.87 (1H, dd, J=4.5 HZ, 12.8 Hz, H-3eq), 3.41 (3H, s, OCH₃), 7.43–7.91 (5H, m,

Synthetic Example 15

Synthesis of 4,7,8,9-tetra-O-acetyl-5-tert-butyloxycarbonylamino-3,5-dideoxy-2-O-methyl-α-D-glycero-D-galacto-2-nonulopyranosonic acid [compound (XXIII) wherein R³ is methyl, R⁴ is acetyl and R¹⁵ is tert-butyloxycarbonyl].

The title compound (392 mg, yield=96.6%) was obtained by using the compound (208 mg, 0.74 mmol) which was made in Synthetic example 12 and di-tert-butylcarbonate (200 mg, 0.92 mmol), in a procedure similar to that described in Synthetic example 13.

¹H-NMR (CDCl₃) δ(ppm): 1.32 (9H, s, (CH₃)₃C—), 1.83 (1H, m, H-3ax), 1.96–2.08 (12H, Ac×4), 2.62 (1H, dd, J=4.8 Hz, 12.5 Hz, H-3eq), 3.34 (3H, s, OCH₃), 4.91 (1H, m, H-4), 5.35–5.45 (2H, m, H-7, 8)

Example 55

Synthesis of 3α-[N-(4,7,8,9-tetra-O-acetyl-5-tert-butyloxycarbonylamino-3,5-dideoxy-2-O-methyl-α-D-glycero-D-galacto-2-nonulopyranosonyl) amino] cholestane (the α-isomer of compound No. 392 in Table 5).

The title compound (485 mg, yield=73.9%) was obtained by using the compound (392 mg, 0.71 mmol) which was made in Synthetic example 15 and 3α-aminocholestane hydrochloride (360 mg, 0.85 mmol), in a procedure similar to that described in Synthetic example 1.

IR (KBr) (cm⁻¹) 3435, 3380, 2940, 2870, 1750, 1680

¹H-NMR (CDCl₃) δ(ppm): 0.62 (3H, s, 18'-CH₃), 0.77–0.89 (12H, 19'-CH₃, 21'-CH₃, 26'-CH₃, 27'-CH₃), 1.37 (9H, s, (CH₃)₃C—), 2.00, 2.01, 2.04, 2.11 (12H, s×4 Ac), 2.21 (1H, dd, J=5.4 Hz, 13.1 Hz, H-3eq), 3.38 (3H, s, OCH₃), 5.21–5.38 (3H, m, H-4, 7, 8), 6.74 (1H, d, J=7.5 Hz, NH)

Example 56

Synthesis of 3α-[N-(5-tert-butyloxycarbonylamino-3,5-dideoxy-2-O-methyl-α-D-glycero-D-galacto-2-nonulopyranosonyl) amino] cholestane (the α-isomer of compound No. 324 in Table 5).

The title compound (165 mg, yield 69.0%) was obtained by using the compound (293 mg, 0.32 mmol) which was obtained in Example 55, in a procedure similar to that described in Example 3.

m.p. 228°–232° C.

IR (KBr) (cm⁻¹) 3400, 2950, 2850, 1650

¹H-NMR [CDCl₃—CD₃OD (1:1)] δ(ppm): 0.69 (3H, s, 18'-CH₃), 0.84–0.95 (12H, 19'-CH₃, 21'-CH₃, 26'-CH₃, 27'-CH₃), 1.47 (9H, s, (CH₃)₃C—), 2.79 (1H, s, dd, J=4.2 Hz, 13.0 Hz, H-3eq), 3.37 (3H, s, OCH₃), 4.00 (1H, m, H-3')

Synthetic Example 16

Synthesis of 4,7,8,9-tetra-O-acetyl-5-benzyloxycarbonylamino-3,5-dideoxy-2-O-methyl-α-D-glycero-D-galacto-2-nonulopyranosonic acid [compound (XXIII) wherein R³ is methyl, R⁴ is acetyl and R¹⁵ is benzyloxycarbonyl].

The title compound (1.46 g, yield=84.9%) was obtained by using the compound (830 mg, 2.95 mmol) which was made in Synthetic example 12 and benzyloxycarbonyl chloride (0.52 ml, 3.26 mmol), in a procedure similar to that described in Synthetic example 13.

¹H-NMR (CDCl₃) δ(ppm): 1.99–2.15 (13H, H-3ax, Ac×4), 2.64 (1H, H-3eq), 3.39 (3H, s, OCH₃), 4.95 (1H, m, H-4), 5.40–5.50 (2H, m, H-7, 8), 7.27–7.37 (5H, m,

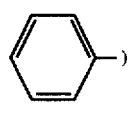
)

Example 57

Synthesis of 3α-[N-(4,6,7,8-tetra-O-acetyl-5-benzyloxycarbonylamino-3,5-dideoxy-2-O-methyl-α-D-glycero-D-galacto-2-nonulopyranosonyl) amino] cholestane (the α-isomer of compound No. 393 in Table 5).

The title compound (892 mg, yield=61.5%) was obtained by using the compound (1.46 g, 2.50 mmol) which was made in Synthetic example 16 and 3α-aminocholestane hydrochloride (1.20 g, 2.83 mmol), in a procedure similar to that described in Synthetic example 1.

IR (KBr) (cm⁻¹) 3430, 3325, 2940, 2870, 1750, 1680

¹H-NMR (CDCl₃) δ(ppm): 0.62 (3H, s, 18'-CH₃), 0.76–0.89 (12H, 19'-CH₃, 21'-CH₃, 26'-CH₃, 27'-CH₃), 1.80, 2.01, 2.04, 2.14 (12H, s×4, Ac), 2.19 (1H, dd, J=5.4 Hz, 13.2 Hz, H-3eq), 3.38 (3H, s, OCH₃), 4.90–5.15 (2H,

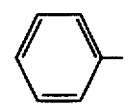

CH₂), 5.22–5.38 (3H, m, H-4, 7, 8), 6.72 (1H, d, J=7.8 Hz, NH), 7.25–7.33 (5H, m,

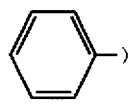
)

Example 58

Synthesis of 3α-[N-(5-benzyloxycarbonylamino-3,5-dideoxy-2-O-methyl-α-D-glycero-D-galacto-2-nonulopyranosonyl) amino] cholestane (the α-isomer of compound No. 325 in Table 5).

The title compound (133 mg, yield=40.5%) was obtained by using the compound (398 mg, 0.42 mmol) which was made in Example 57, in a procedure similar to that described in Example 3.

IR (KBr) (cm⁻¹) 3440, 2940, 2865, 1690, 1645

¹H-NMR [CDCl₃—CD₃OD (1:1)] δ(ppm): 0.69 (3H, s, 18'-CH₃), 0.84–0.95 (12H, 19'-CH₃, 21'-CH₃, 26'-CH₃, 27'-CH₃), 2.79 (1H, dd, J=4.0 Hz, 13.0 Hz, H-3eq), 3.37 (3H, s, OCH₃), 4.00 (1H, m, H-3'), 5.13 (2H, s,

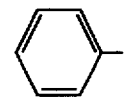

CH₂), 7.30–7.38 (5H, m,

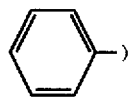
)

Example 59

Synthesis of 3α-[N-(4,6,7,8-tetra-O-acetyl-3,5-dideoxy-2-O-methyl-5-propionamido-α-D-glycero-D-galacto-2-nonulopyranosonyl) amino] cholestane (the α-isomer of compound No. 368 in Table 5).

The compound (533 mg, 0.56 mmol) which obtained in Example 57 was dissolved in ethanol (30 ml), and then 1N hydrochloric acid (0.6 ml, 0.60 mmol) and 5% palladium-carbon (110 g) were added. The mixture was stirred in an atmosphere of hydrogen for 5 hours. The catalyst was filtered off and the solvent was evaporated under reduced pressure to obtain 3α-[N-(5-amino-4,6,7,8-tetra-O-acetyl-3, 5-dideoxy-2-O-methyl-α-D-glycero-D-galacto-2- nonulopyranosonyl) amino] cholestane hydrochloride. The hydrochloride salt was dissolved in dichloromethane (25 ml), and propionyl chloride (0.43 ml, 4.97 mmol) and triethylamine (0.76 ml, 5.48 mmol) were added under ice cooling. The reaction mixture was stirred for 1 hour, washed with water, and dried over anhydrous magnesium sulfate. The solvent was evaporated under reduced pressure and the resulting syrup was purified by silica gel column chromatography [Merck silica gel 60, eluent: chloroform/methanol (200:1)] to obtain the title compound (382 mg, yield= 77.9%).

IR (KBr) (cm$^{-1}$) 3435, 3375, 2940, 2870, 1750, 1685

$^1$H-NMR (CDCl$_3$) δ(ppm): 0.62 (3H, s, 18'-CH$_3$), 0.77–0.89 (12H, 19'-CH$_3$, 21'-CH$_3$, 26'-CH$_3$, 27'-CH$_3$), 1.97, 2.01, 2.04, 2.11 (12H, s×4, Ac), 2.18 (1H, dd, J=5.5 Hz, 13.3 Hz, H-3eq), 3.40 (3H, s, OCH$_3$), 5.19–5.27 (3H, m, H-7, 8, NH), 5.39 (1H, m, H-4), 6.77 (1H, d, J=7.7 Hz, NH)

Example 60

Synthesis of 3α-[N-(3,5-dideoxy-2-O-methyl-5-propionamido-α-D-glycero-D-galacto-2-nonulopyranosonyl) amino] cholestane (the α-isomer of compound No. 300 in Table 5).

The title compound (101 mg, yield=37%) was obtained by using the compound (339 mg, 0.39 mmol) which was made in Example 59, in a procedure similar to that described in Example 9.

IR (KBr) (cm$^{-1}$) 3440, 3321, 2935, 2870, 1655, 1630

$^1$H-NMR [CDCl$_3$—CD$_3$OD (1:1)] δ(ppm): 0.68 (3H, s, 18'-CH$_3$), 0.83–0.94 (12H, 19'-CH$_3$, 21'-CH$_3$, 26'-CH$_3$, 27'-CH$_3$), 2.30 (2H, q, J=7.4 Hz, CH$_3$C$\underline{H}_2$CON), 2.80 (1H, dd, J=4.5 HZ, 12.8 Hz, H-3eq), 3.38 (3H, s, OCH$_3$), 4.01 (1H, m, H-3')

Example 61

Synthesis of 3α-[N-4,6,7,8-tetra-O-acetyl-3,5-dideoxy-5-methanesulfonamido-2-O-methyl-α-D-glycero-D-galacto-2-nonulopyranosonyl) amino] cholestane (the α-isomer of compound No. 419 in Table 5).

The title compound (252 mg, yield=71.6%) was obtained by using the compound (400 mg, 0.42 mmol) which was made in Example 57 and methanesulfonyl chloride (0.04 ml, 0.52 mmol), in a procedure similar to that described in Example 59.

IR (KBr) (cm$^{-1}$) 3435, 3270, 2940, 2870, 1750, 1680

$^1$H-NMR (CDCl$_3$) δ(ppm): 0.62 (3H, s, 18'-CH$_3$), 0.77–0.89 (12H, 19'-CH$_3$, 21'-CH$_3$, 26'-CH$_3$, 27'-CH$_3$), 2.01, 2.05, 2.08, 2.13 (12H, s×4, Ac), 2.20 (1H, J=5.2 Hz, 13.2 Hz, H-3eq), 3.01 (3H, s, CH$_3$SO$_2$), 3.38 (3H, s, OCH$_3$), 5.24–5.44 (3H, m, H-4, 7, 8), 6.75 (1H, d, J=7.8 Hz, NH)

Example 62

Synthesis of 3α-[N-(3,5-dideoxy-5-methanesulfonamido-2-O-methyl-α-D-glycero-D-galacto-2-nonulopyranonsonyl) amino] cholestane (the α-isomer of compound No. 351 in Table 5).

The title compound (110 mg, yield=62.1%) was obtained by using the compound (218 mg, 0.24 mmol) which was obtained in Example 61, in a procedure similar to that described in Example 9.

IR (KBr) (cm$^{-1}$) 3470, 3320, 2950, 2855, 1665

$^1$H-NMR (CD$_3$OD) δ(ppm): 0.73 (3H, s, 18'-CH$_3$), 0.88–0.99 (12H, 19'-CH$_3$, 21'-CH$_3$, 26'-CH$_3$, 27'-CH$_3$), 2.82 (1H, dd, J=4.5 Hz, 12.6 Hz, H-3eq), 3.13 (3H, s, CH$_3$SO$_2$), 3.38 (3H, s, OCH$_3$).

Example 63

Synthesis of 3α-[N-(4, 6, 7, 8-tetra-O-acetyl-5-benzenesulfonamide-3,5-dideoxy-2-O-methyl-α-D-glycero-D-galacto-2-nonulopyranosonyl) amino] cholestane (the α-isomer of compound No. 423 in Table 5).

The title compound (390 mg, yield=76.2%) was obtained by using the compound (509 mg, 0.53 mmol) which was obtained in Example 57 and benzenesulfonyl chloride (0.6 ml, 4.69 mmol), in a procedure similar to that described in Example 59.

$^1$H-NMR (CDCl$_3$) δ(ppm): 0.62 (3H, s, 18'-CH$_3$), 0.76–0.89 (12H, 19'-CH$_3$, 21'-CH$_3$, 26'-CH$_3$, 27'-CH$_3$), 1.72, 2.02, 2.05, 2.19 (12H, s×4, Ac), 3.38 (3H, s, OCH$_3$), 5.27–5.38 (3H, m, H-4, 7, 8), 6.75 (1H, d, J=7.5 Hz, NH), 7.44–7.55 (3H, m,

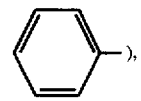

7.85–7.89 (2H, m,

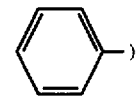

Example 64

Synthesis of 3α-[N-(5-benzenesulfonamido-3,5-dideoxy-2-O-methyl-α-D-glycero-D-galacto-2-nonulopyranosonyl) amino] cholestane (the α-isomer of compound No. 355 in Table 5).

The title compound (139 mg, yield=44.4%) was obtained by using the compound (380 mg, 0.40 mmol) which was made in Example 63, in a procedure similar to that described in Example 9.

IR (KBr) (cm$^{-1}$) 3425, 2935, 2870, 1655

$^1$H-NMR (CD$_3$OD) δ(ppm): 0.73 (3H, s, 18'-CH$_3$), 0.88–0.99 (12H, 19'-CH$_3$, 21'-CH$_3$, 26'-CH$_3$, 27'-CH$_3$), 2.67 (1H, dd, J=4.2 Hz, 13.1 Hz, H-3eq), 3.36 (3H, s, OCH$_3$), 4.02 (1H, m, H-3'), 7.51–7.62 (3H, m,

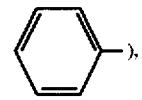

7.91–7.95 (2H, m,

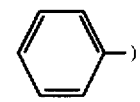

Synthetic Example 17

Synthesis of 3α-[N-(2,4,5,7,8,9-hexa-O-acetyl-3-deoxy-β-D-glycero-D-galacto-2-nonulopyranosonyl) amino] cholestane [compound (XLIV) wherein R$^1$ is 3α-cholestane, R$^2$ is hydrogen, R$^{4'}$ is acetyl and R$^{14'}$ is acetyl].

2,4,5,7,8,9-Hexa-O-acetyl-3-deoxy-β-D-glycero-D-galacto-2-nonulopyranosonic acid (800 mg, 1.54 mmol) was dissolved in tetrahydrofuran (50 ml) and the solution was cooled to −10° C. Isobutyl chloroformate (0.219 ml, 1.69 mmol) and triethylamine (0.236 ml, 1.69 mmol) were added and the mixture was stirred for 30 minutes. 3α-Aminocholestane hydrochloride (784 mg, 1.85 mmol) and triethylamine (0.258 ml, 1.85 mmol) were added, and the mixture was warmed to 0° C. over the period of 30 minutes and stirred at 0° C. for 3 hours and then at room temperature for 12 hours. Ethyl acetate (100 ml) was then added, and the resulting mixture was washed with 0.2N hydrochloric acid, saturated aqueous solution of sodium hydrogen carbonate and saturated saline solution, and dried over anhydrous magnesium sulfate. The solvent was evaporated under reduced pressure and the resulting syrup was purified by silica gel column chromatography [Merck silica gel 60, eluent: hexane/ethyl acetate (2:1)] to obtain the title compound (391 mg, yield=28%).

IR (KBr) (cm$^{-1}$) 3390, 2950, 2870, 1765, 1700

$^1$H-NMR (CDCl$_3$) δ(ppm): 0.65 (3H, s, 18'-CH$_3$), 0.80–0.91 (12H, 19'-CH$_3$, 21'-CH$_3$, 26'-CH$_3$, 27'-CH$_3$), 1.88 (1H, dd, J=11.7 Hz, 13.6 Hz, H-3ax), 2.01, 2.04, 2.06, 2.07, 2.13, 2.14 (18H, s×6, Ac), 2.68 (1H, dd, J=5.1 Hz, 13.6 Hz, H-3eq), 4.08 (1H, m, H-3'), 4.12 (1H, dd, J=1.9 Hz, 10.0 Hz, H-6), 4.20 (1H, dd, J=5.4 Hz, 12.5 Hz, H-9), 4.34 (1H, dd, J=2.6 Hz, 12.5 Hz, H-9), 4.92 (1H, t, J=10.0 Hz, H-5), 5.17 (1H, m, H-8), 5.33 (1H, m, H-4), 5.40 (1H, dd, J=1.9 Hz, 7.6 Hz, H-7), 6.87 (1H, d, J=8.0 Hz, NH)

Example 65

Synthesis of 3α-[N-(4,5,7,8,9-penta-O-acetyl-3-deoxy-2-O-methyl-α-D-glycero-D-galacto-2-nonulopyranosonyl) amino] cholestane (the α-isomer of compound No. 435 in Table 5).

The compound (352 mg, 0.395 mmol) which was synthesized in Synthetic example 17 was dissolved in acetyl chloride (15 ml) saturated with hydrogen chloride gas. The vessel in which the above solution was placed was tightly stoppered and allowed to stand at room temperature for 15 hours. The solvent was evaporated under reduced pressure and the residue was dissolved in benzene (5 ml). Calcium sulfate (500 mg) was added and the mixture was stirred for 1 hour. A solution of silver trifluoromethanesulfonate (142 mg, 0.553 mmol) and 2,4,6-trimethylpyridine (62 mg, 0.474 mmol) in nitromethane (1 ml)-ether (1.5 ml), and methanol (0.96 ml) were added under ice cooling. The resulting mixture was stirred for 15 hours at room temperature. To the reaction mixture was added chloroform (30 ml) and the mixture was filtered through celite. The filtrate was washed with 0.2N sodium thiosulfate, 0.2N hydrochloric acid, saturated aqueous solution of sodium hydrogen carbonate and saturated saline solution, and dried over anhydrous magnesium sulfate. The solvent was evaporated under reduced pressure and the resulting syrup was purified by slica gel column chromatography [Merck silica gel 60, eluent: hexane/ethyl acetate (2:1)] to obtain the title compound (257 mg, yield=75%).

IR (KBr) (cm$^{-1}$) 3440, 2940, 2870, 1750, 1680

$^1$H-NMR (CDCl$_3$) δ(ppm): 0.65 (3H, s, 18'-CH$_3$), 0.80 (3H, s, 19'-CH$_3$), 0.85–0.91 (9H, 21'-CH$_3$, 26'-CH$_3$, 27'-CH$_3$), 2.00, 2.02, 2.04, 2.10, 2.11 (15H, s×5, Ac), 2.32 (1H, dd, J=5.8 Hz, 13.4 Hz, H-3eq), 3.40 (3H, s, OCH$_3$), 4.06 (1H, m, H-3'), 4.09 (1H, dd, J=5.6 Hz, 12.4 Hz, H-9), 4.31 (1H, dd, J=2.3 Hz, 12.4 Hz, H-9), 4.64 (1H, dd, J=1.9 Hz, 10.4 Hz, H-6), 4.97 (1H, t, J=10.4 Hz, H-5), 5.29 (1H, dd, J=1.9 Hz, 8.4 Hz, H-7), 5.30–5.45 (2H, m, H-4, H-8), 6.75 (1H, d, J=7.5 Hz, NH)

Example 66

Synthesis of 3α-[N-(3-deoxy-2-O-methyl-α-D-glycero-D-galacto-2-nonulopyranosonyl) amino] cholestane (the α-isomer of compound No. 367 in Table 5).

The title compound (60 mg, yield=48%) was obtained by using the compound (164 mg, 0.190 mmol) which was synthesized in Example 65, in a procedure similar to that described in Example 3.

m.p. 228°–233° C. (decomposition)

IR (KBr) (cm$^{-1}$) 3420, 2935, 2870, 1660

$^1$H-NMR [CDCl$_3$—CD$_3$OD (1:1)] δ(ppm): 0.67 (3H, s, 18'-CH$_3$), 0.83–0.93 (12H, 19'-CH$_3$, 21'-CH$_3$, 26'-CH$_3$, 27'-CH$_3$), 2.74 (1H, dd, J=4.3 Hz, 12.9 Hz, H-3eq), 3.48 (3H, s, OCH$_3$), 4.37 (1H, m, H-3')

Synthetic Example 18

Synthesis of benzyl 4,5,7,8,9-penta-O-acetyl-3-deoxy-2-O-methyl-α-D-glycero-D-galacto-2-nonulopyranosonate [compound (XLI-α)] wherein R$^3$ is methyl, R$^4$ is acetyl and R$^{14'}$ is acetyl].

Benzyl 2,4,5,7,8,9-hexa-O-acetyl-3-deoxy-β-D-glycero-D-galacto-2-nonulopyranosonate (6.18 g, 10.12 mmol) was dissolved in acetyl chloride (75 ml) saturated with hydrogen chloride gas. The vessel in which the above solution was placed was tightly stoppered and allowed to stand at room temperature for 18 hours. The solvent was evaporated under reduced pressure and the residue was subjected to azeotropic distillation with toluene completely to remove the solvent. The residue was dissolved in methanol (100 ml), and silver carbonate (4.19 g, 15.18 mmol) and calcium sulfate (6.5 g) were added under ice cooling. The resulting mixture was stirred under ice cooling for 1 hour and then at room temperature for 3 hours. The reaction solution was filtered through celite and the solvent in the filtrate was evaporated under reduced pressure. The residue was dissolved in chloroform (200 ml) and the solution was washed with 2N sodium thiosulfate and saturated saline solution, and dried over anhydrous sodium sulfate. The solvent was evaporated under reduced pressure and the resulting syrup was purified by silica gel column chromatography [Merck silica gel 60, eluent: hexane/ethyl acetate (2:1)] to obtain the title compound (2.27 g, yield=38%).

IR (KBr) (cm$^{-1}$) 3480, 2980, 1750

$^1$H-NMR (CDCl$_3$) δ(ppm): 2.01, 2.01, 2.04, 2.11, 2.18 (15H, s×5, Ac), 2.72 (1H, dd, J=3.6 Hz, 12.6 Hz, H-3eq), 3.25 (3H, s, OCH$_3$), 4.05–4.20 (2H, m, H-6, H-9), 4.27 (1H, dd, J=2.3 Hz, 12.5 Hz, H-9), 4.80–4.95 (2H, m, H-4, H-5)

Synthetic Example 19

Synthesis of 4,5,7,8,9-penta-O-acetyl-3-deoxy-2-O-methyl-α-D-glycero-D-galacto-nonulopyranosonic acid [Compound (XLII-α) wherein R$^3$ is methyl, R$^4$ is acetyl and R$^{14'}$ is acetyl].

The compound (1.034 g, 1.78 mmol) which was synthesized in Synthetic example 18 was dissolved in ethanol (50 ml) and 5% palladium-carbon (100 mg) was added. The mixture was stirred in an atmosphere of hydrogen for 3 hours. The catalyst was filtered off and the solvent was evaporated under reduced pressure to obtain the title compound (845 mg, yield=96%).

IR (KBr) (cm$^{-1}$) 3490, 2980, 1750

$^1$H-NMR (CDCl$_3$) δ(ppm): 1.96 (1H, dd, J=12.8 Hz, 13.2 Hz, H=3ax), 2.02, 2.03, 2.06, 2.12, 2.16 (15H, s×5, Ac), 2.66 (1H, dd, J=5.0 Hz, 13.2 Hz, H-3eq), 3.40 (3H, s, OCH$_3$), 4.13 (1H, dd, J=5.1 Hz, 12.7 Hz, H-9), 4.21 (1H, dd, J=2.0 Hz, 10.0 Hz, H-6), 4.31 (1H, dd, J=2.5 Hz, 12.7 Hz, H-9), 4.91 (1H, t, J=10.0 Hz, H-5), 5.07 (1H, m, H-4), 5.35 (1H, dd, J=2.0 Hz, 9.0 Hz, H-7), 5.45 (1H, m, H-8)

Example 67

Synthesis of 3β-[N-(4,5,7,8,9-penta-O-acetyl-3-deoxy-2-O-methyl-α-D-glycero-D-galacto-2-nonulopyranosonyl) amino] cholestane (the β-isomer of compound No. 435 in Table 5).

The title compound (268 mg, yield=43%) was obtained by using the compound (358 mg, 0.727 mmol) which was synthesized in Synthetic example 19 and 3β-aminocholestane (310 mg, 0.800 mmol), in a procedure similar to that described in Example 2.

IR (KBr) (cm⁻¹) 3390, 2940, 2870, 1750, 1680

¹H-NMR (CDCl₃) δ(ppm): 0.64 (3H, s, 18'-CH₃), 0.82–0.91 (12H, 19'-CH₃, 21'-CH₃, 26'-CH₃, 27'-CH₃), 2.00, 2.00, 2.05, 2.11, 2.11 (15H, s×5, Ac), 2.39 (1H, dd, J=6.3 Hz, 13.8 Hz, H-3eq), 3.36 (3H, s, OCH₃), 3.77 (1H, m, H-3'), 4.02 (1H, dd, J=6.7 Hz, 12.4 Hz, H-9), 4.25 (1H, dd, J=1.8 Hz, 10.4 Hz, H-6), 4.51 (1H, dd, J=2.3 Hz, 12.4 Hz, H-9), 5.09 (1H, dd, J=9.0 Hz, 10.4 Hz, H-5), 5.24–5.31 (2H, m, H-4, H-7), 5.40 (1H, m, H-8), 6.74 (1H, d, J=8.6 Hz, NH)

Example 68

Synthesis of 3β-[N-(3-deoxy-2-O-methyl-α-D-glycero-D-galacto-2-nonulopyranosonyl) amino] cholestane (the β-isomer of compound No. 367 in Table 5).

The title compound (71 mg, yield=42%) was obtained by using the compound (225 mg, 0.261 mmol) which was synthesized in Example 67, in a procedure similar to that described in Example 3.

m.p. 239°–240° C. (decomposition)

IR (KBr) (cm⁻¹) 3420, 2940, 2870, 1750, 1670

¹H-NMR [CDCl₃—CD₃OD (1:1)] δ(ppm): 0.68 (3H, s, 18'-CH₃), 0.84–0.93 (12H, 19'-CH₃, 21'-CH₃, 26'-CH₃, 27'-CH₃), 2.77 (1H, dd, J=3.9 Hz, 12.4 Hz, H-3eq), 3.30 (3H, s, OCH₃)

Example 69

Synthesis of 3α-[N-(4,5,7,8,9-penta-O-acetyl-3-deoxy-2-O-methyl-α-D-glycero-D-galacto-2-nonulopyranosonyl) amino]-5-cholestene (the α-isomer of compound No. 575 in Table 7).

The title compound (301 mg, yield=53%) was obtained by using the compound (294 mg, 0.597 mmol) which was synthesized in Synthetic example 19 and 3α-amino-5-cholestene (253 mg, 0.657 mmol), in a procedure similar to that described in Example 2.

IR (KBr) (cm⁻¹) 2940, 1750, 1685

¹H-NMR (CDCl₃) δ(ppm): 0.68 (3H, s, 18'-CH₃), 0.85–0.93 (12H, 19'-CH₃, 21'-CH₃, 26'-CH₃, 27'-CH₃), 2.00, 2.02, 2.04, 2.10, 2.11 (15H, s×5, Ac), 2.25 (1H, dd, J=5.4 Hz, 13.2 Hz, H-3eq), 2.58 (1H, d, J=3.2 Hz, H-7'), 3.34 (3H, s, OCH₃), 4.08 (1H, brs, H-3'), 4.12 (1H, dd, J=5.3 Hz, 12.5 Hz, H-9), 4.24 (1H, dd, J=2.3 Hz, 12.5 Hz, H-9), 4.82–4.96 (2H, m, H-5, H-6), 5.25–5.41 (4H, m, H-4, H-7, H-8, H-6'), 6.43 (1H, d, J=7.5 Hz, NH)

Example 70

Synthesis of 3α-[N-(3-deoxy-2-O-methyl-α-D-glycero-D-galacto-2-nonulopyranosonyl) amino] cholestene (the α-isomer of compound No. 507 in Table 7).

The title compound (138 mg, yield=70%) was obtained by using the compound (258 mg, 0.300 mmol) which was synthesized in Example 69, in a procedure similar to that described in Example 3.

m.p. 216°–219° C. (decomposition)

IR (KBr) (cm⁻¹) 3440, 3330, 2950, 2870, 1665

¹H-NMR [CDCl₃—CD₃OD (1:1)] δ(ppm): 0.71 (3H, s, 18'-CH₃), 0.86–0.95 (12H, 19'-CH₃, 21'-CH₃, 26'-CH₃, 27'-CH₃), 2.29 (1H, d, J=14.5 Hz, H-7'), 2.55 (1H, d, J=14.5 Hz, H-7'), 2.67 (1H, dd, J=3.7 Hz, 12.3 Hz, H-3eq), 3.32 (3H, s, OCH₃), 4.05 (1H, brs, H-3'), 5.35 (1H, brs, H-6')

Synthetic Example 20

Synthesis of benzyl 4,5,7,8,9-penta-O-acetyl-3-deoxy-2-O-methyl-β-D-glycero-D-galacto-2-nonulopyranonsonate [Compound (XLI-β) wherein R³ is methyl, R⁴' is acetyl and R¹⁴' is acetyl].

Methyl 3-deoxy-2-O-methyl-β-D-glycero-D-galacto-2-nonulopyranosonate (2.43 g, 8.20 mmol) was dissolved in water (100 ml) and 1N sodium hydroxide (12.36 ml, 12.36 mmol) was added under ice cooling. The mixture was stirred for 1 hour and then the solvent was evaporated under reduced pressure. The residue was triturated with methanol and filtered. The resulting solid was suspended in dimethylformamide (50 ml), and benzyl bromide (0.97 ml, 8.20 mmol) was added. The mixture was stirred for 12 hours. The solvent of the reaction solution was evaporated under reduced pressure. The residue was dissolved in pyridine (50 ml), and 4-dimethylaminopyridine (100 mg, 0.82 mmol), and acetic anhydride (5.81 ml, 61.5 mmol) was added under ice cooling. The mixture was stirred for 12 hours. The reaction mixture was again cooled with ice, and methanol (5 ml) was added. After stirring for 30 minutes, the solvent was evaporated under reduced pressure. The residue was dissolved in ethyl acetate (100 ml), washed successively with 0.1N hydrochloric acid, saturated aqueous solution of sodium hydrogen carbonate and saturated saline solution, and then dried over anhydrous magnesium sulfate. The solvent was evaporated under reduced pressure and the resulting syrup was purified by silica gel column chromatography [Merck silica gel 60, developing solvent: haxane/ethyl acetate (3:2)] to obtain the title compound (2.14 g, yield=45%).

IR (KBr) (cm⁻¹) 2980, 1750, 1240

¹H-NMR (CDCl₃) δ(ppm): 1.84 (1H, dd, J=11.7 Hz, 13.0 Hz, H-3ax), 1.98, 2.01, 2.01, 2.05, 2.07 (15H, s×5, Ac), 2.52 (1H, dd, J=5.2 Hz, 13.0 Hz, H-3eq), 3.22 (3H, s, OCH₃), 4.05 (1H, dd, J=2.1 Hz, 10.0 Hz, H-6), 4.15 (1H, dd, J=6.8 Hz, 12.5 Hz, H-9), 4.68 (1H, dd, J=2.4 Hz, 12.5 Hz, H-9), 4.88 (1H, t, J=10.0 Hz, H-5), 5.23 (2H, s, CH₂C₆H₅), 5.18–5.36 (2H, m, H-4, H-8), 5.41 (1H, dd, J=2.1 Hz, 5.4 Hz, H-7), 7.36 (5H, brs, C₆H₅)

Synthetic Example 21

Synthesis of 4,5,7,8,9-penta-O-acetyl-3-deoxy-2-O-methyl-β-D-glycero-D-galacto-2-nonulopyrasonic acid [compound (XLII-β) wherein R³ is methyl, R⁴' is acetyl and R¹⁴' is acetyl].

The title compound (1.71 g, quantitative yield) was obtained by using the compound (1.956 g, 3.36 mmol) which was synthesized in Synthetic example 20, in a procedure similar to that described in Synthetic example 19.

IR (KBr) (cm⁻¹) 3480, 2980, 1750

¹H-NMR (CDCl₃) δ(ppm): 1.89 (1H, dd, J=11.7 Hz, 13.4 Hz, H-3ax), 2.01, 2.03, 2.06, 2.10, 2.11 (15H, s×5, Ac), 2.66 (1H, dd, J=5.0 Hz, 13.4 Hz, H-3eq), 3.32 (3H, s, OCH₃), 4.06–4.14 (2H, m, H-6, 9), 4.55 (1H, dd, J=2.2 Hz, 12.7 Hz, H-9), 4.93 (1H, t, J=10.0 Hz, H-5), 5.21–5.41 (3H, m, H-4, 7, 8)

Example 71

Synthesis of 3α-[N-(4,5,7,8,9-penta-O-acetyl-3-deoxy-2-O-methyl-β-D-glycero-D-galacto- 2-nonulopyranosonyl) amino] cholestane (the α-isomer of compound No. 439 in Table 6).

The title compound (327 mg. yield=43%) was obtained by using the compound (426 mg. 0.865 mmol) which was synthesized in Synthetic example 21 and 3α-aminocholestane (369 mg. 0.952 mmol), in a procedure similar to that described in Example 2.

IR (KBr) (cm$^{-1}$) 3390, 2950, 2870, 1765, 1700

$^1$H-NMR (CDCl$_3$) δ(ppm): 0.65 (3H, s, 18'-CH$_3$), 0.81–0.90 (12H, 19'-CH$_3$, 21'-CH$_3$, 26'-CH$_3$, 27'-CH$_3$), 1.99, 2.04, 2.06, 2.11, 2.12 (15H, s×5, Ac), 2.60 (1H, dd, J=5.2 Hz, 13.5 Hz, H-3eq), 3.19 (3H, s, OCH$_3$), 4.09–4.19 (3H, m, H-6, H-9, H-3'), 4.37 (1H, dd, J=2.4 Hz, 12.5 Hz, H-9), 4.87 (1H, t, J=10.0 Hz, H-5), 5.27–5.36 (2H, m, H-4, H-8), 5.41 (1H, dd, J=1.7 Hz, 8.2 Hz, H-7), 6.99 (1H, d, J=7.9 Hz, NH)

Example 72

Synthesis of 3α-[N-(3-deoxy-2-O-methyl-β-D-glycero-D-galacto-2-nonulopyranosonyl) amino] cholestane (the α-isomer of compound No. 438 in Table 6).

The title compound (100 mg. yield=67%) was obtained by using the compound (197 mg. 0.229 mmol) which was synthesized in Example 71, in a procedure similar to that described in Example 3.

m.p. 168°–183° C. (decomposition)

IR(KBr) (cm$^{-1}$) 3420, 2930, 2870, 1670

$^1$H-NMR (CD$_3$OD) δ(ppm): 0.74 (3H, s, 18'-CH$_3$), 0.89–0.99 (12H, 19'-CH$_3$, 21'-CH$_3$, 26'-CH$_3$, 27'-CH$_3$), 2.35 (1H, dd, J=5.0 Hz, 12.9 Hz, H-3eq), 3.25 (3H, s, OCH$_3$), 3.58 (1H, t, J=9.3 Hz, H-5)

Example 73

Synthesis of 3β-[N-(4,5,7,8,9-penta-O-acetyl-3-deoxy-2-O-methyl-β-D-glycero-D-galacto-2-nonulopyranosonyl) amino] cholestane (the β-isomer of compound No. 439 in Table 6).

The title compound (319 mg. yield=42%) was obtained by using the compound (433 mg. 0.879 mmol), which was synthesized in synthetic example 21, and 3β-aminocholestane (375 mg. 0.967 mmol), in a procedure similar to that described in Example 2.

IR (KBr) (cm$^{-1}$) 3400, 2940, 2870, 1750, 1685

$^1$H-NMR (CDCl$_3$) δ(ppm): 0.65 (3H, s, 18'-CH$_3$), 0.84–0.91 (12H, 19'-CH$_3$, 21'-CH$_3$, 26'-CH$_3$, 27'-CH$_3$), 1.99, 2.02, 2.06, 2.11, 2.13 (15H, s×5, Ac), 2.66 (1H, dd, J=5.2 Hz, 13.6 Hz, H-3eq), 3.37 (3H, s, OCH$_3$), 3.76 (1H, brs, H-3'), 4.07 (1H, dd, J=5.7 Hz, 12.5 Hz, H-9), 4.15 (1H, dd, J=2.0 Hz, 10.0 Hz, H-6), 4.39 (1H, dd, J=2.2 Hz, 12.5 Hz, H-9), 4.90 (1H, t, J=10.0 Hz, H-5), 5.20–5.40 (3H, m, H-4, 7, 8), 6.58 (1H, d, J=8.4 Hz, NH).

Example 74

Synthesis of 3β-[N-(3-deoxy-2-O-methyl-β-D-glycero-D-galacto-2-nonulopyranosonyl) amino] cholestane (the β-isomer of compound No. 438 in Table 6).

The title compound (137 mg. yield=65%) was obtained by using the compound (279 mg. 0.324 mmol) which was synthesized in Example 73, in a procedure similar to that described in Example 3.

m.p. 203°–212° C. (decomposition)

IR (KBr) (cm$^{-1}$) 3400, 2940, 2870, 1660

$^1$H-NMR (CD$_3$OD) δ(ppm): 0.74 (3H, s, 18'-CH$_3$), 0.91–0.98 (12H, 19'-CH$_3$, 21'-CH$_3$, 26'-CH$_3$, 27'-CH$_3$), 2.32 (1H, dd, J=5.1 Hz, 13.2 Hz, H-3eq), 3.23 (3H, s, OCH$_3$), 3.52 (1H, t, J=9.3 Hz, H-5).

Example 75

Synthesis of 3α-[N-(4,5,7,8,9-penta-O-acetyl-3-deoxy-2-O-methyl-β-D-glycero-D-galacto-2-nonulopyranosonyl) amino]-5-cholestene (the α-isomer of compound No. 579 in Table 8).

The title compound (188 mg. yield=26%) was obtained by using the compound (417 mg. 0.846 mmol) which was synthesized in Synthetic example 21 and 3α-amino-5-cholestene (359 mg. 0.931 mmol), in a procedure similar to that described in Example 2.

IR (KBr) (cm$^{-1}$) 3410, 2940, 2870, 1750, 1690

$^1$H-NMR (CDCl$_3$) δ(ppm): 0.68 (3H, s, 18'-CH$_3$), 0.84–1.09 (12H, 19'-CH$_3$, 21'-CH$_3$, 26'-CH$_3$, 27'-CH$_3$), 1.98, 2.05, 2.06, 2.11, 2.12 (15H, s×5, Ac), 2.57 (1H, dd, J=5.2 Hz, 13.3 Hz, H-3eq), 3.12 (3H, s, OCH$_3$), 4.09 (1H, dd, J=1.7 Hz, 10.0 Hz, H-6), 4.16 (1H, brs, H-3'), 4.19 (1H, dd, J=4.1 Hz, 12.7 Hz, H-9), 4.29 (1H, dd, J=2.4 Hz, 12.7 Hz, H-9), 4.82 (1H, t, J=10.0 Hz, H-5), 5.20 (1H, m, H-8), 5.33 (1H, m, H-4), 5.43 (1H, brs, H-6'), 5.45 (1H, dd, J=1.7 Hz, 9.0 Hz, H-7), 6.83 (1H, d, J=8.0 Hz, NH)

Example 76

Synthesis of 3α-[N-(3-deoxy-2-O-methyl-β-D-glycero-D-galacto-2-nonulopyranosonyl) amino]-5-cholestene (the α-isomer of compound No. 578 in Table 8).

The title compound (116 mg. yield=93%) was obtained by using the compound (164 mg. 0.191 mmol) which was synthesized in Example 75, in a procedure similar to the described in Example 3.

m.p. 191°–194° C. (decomposition)

IR (KBr) (cm$^{-1}$) 3400, 2940, 2870, 1670

$^1$H-NMR (CD$_3$OD) δ(ppm): 0.77 (3H, s, 18'-CH$_3$), 0.91–1.10 (12H, 19'-CH$_3$, 21'-CH$_3$, 26'-CH$_3$, 27'-CH$_3$), 2.34 (1H, dd, J=5.1 Hz, 13.0 Hz, H-3eq), 3.23 (3H, s, OCH$_3$), 3.55 (1H, t, J=10.0 Hz, H-5), 5.51 (1H, d, J=4.6 Hz, H-6')

Experiment 1

The effect of cultured cholinergic neurons in septum derived from neonatal rat to acetyl choline-synthesizing enzyme (choline acetyltransferase: ChAT).

The primary cultures of septal neurons from neonatal rat were prepared as described by Hatanaka et al [H. Hatanaka et al., Dev. Brain Res. 39, 85–95 (1988)]. Namely, septums were removed from a 14-day-old rat and chopped, and dissected fragments were well triturated by an enzymatic treatment (with papain in the presence of DNase I) and a mechanical treatment (pipetting). The dissociated cells were plated at a density of about 5×10$^5$ cells/cm$^2$ on a 48-well plate in which astroglia cells had been previously plated as a feeder layer, and then cultured in DF medium containing 5% precolostrum new born calf serum and 5% inactivated bovine serum (a mixture of equal amounts of Dulbecco's modified Eagle medium and Ham's F12 medium). Astroglia cells were prepared from cerebral cortex of 20-day-old embryonic rat and used after several generations of growth. The culture medium was changed to the same medium on the next day and 4th day from the culture started. The compound to be examined was added in a given concentration for 1-day to 7-day. After the culture for 1 week, the cells were washed and ultrasonically disrupted in 5 mM Tris-HCl buffer containing 0.1% Triton X-100. To the resulting crude enzyme preparation was added [$^{14}$C] acetyl-coenzyme A (0.3 KBq) and the mixture was incubated at 37° C. for 1 hour. After the reaction was stopped, the produced [$^{14}$C]

acetylcholine was extracted into a toluene scintillator and determined by a liquid scintillation counter. The value of ChAT activity of the control group is usually about 1.5 pmol/min/well, and the ChAT activity of the compounds to be examined was expressed as the ratio (%) to the value of ChAT activity of the control group, which was regarded as 100. The test results are shown in Table 9.

TABLE 9

| Compound No. | Concentration (µM) | | |
|---|---|---|---|
| | 3 | 10 | 30 |
| α-Isomer of No. 4 in Table 1 | 142** | 196** | 230** |
| α-Isomer of No. 19 in Table 1 | 149 | 123 | 157* |
| α-Isomer of No. 21 in Table 1 | 163** | 116 | 106 |
| α-Isomer of No. 234 in Table 1 | 116 | 177* | 220** |
| α-Isomer of No. 260 in Table 2 | 170** | 183* | 208* |
| α-Isomer of No. 268 in Table 3 | 106 | 110* | 136* |
| α-Isomer of No. 281 in Table 3 | 101 | 135* | 171* |
| α-Isomer of No. 367 in Table 5 | 245** | 259** | 257** |
| α-Isomer of No. 507 in Table 7 | 129** | 133** | — |

*P < 0.05
**P < 0.01

Experiment 2

Effect of the compound of the invention on neuronal death caused by glutamic acid.

Glutamic acid is associated with neuronal death, and nerve cell culture has been used as a model system of neuronal death in the studies of toxicity of glutamic acid [Akinori Akaike: Neurotoxicity of glutamic acid and nerve-protecting factors. Nippon Yakurigaku Zasshi 103, 198–201 (1994)].

Inhibition of glutamate-induced neuronal death by the compound of the invention was evaluated using the following method:

That is, brain of 18-day-old fetuses of Wistar rat was removed. The hippocampal region was cut out under ice-cold conditions and minced with a scalpel. The minced tissue was digested with papain (Worthington) at 37° C. for 20 minutes, and then, the reaction was stopped by addition of horse serum (Sigma). The minced tissue was then washed with DMEM medium (Gibco) twice, and triturated by pipetting. Finally, the cell suspension was filtered through a double layer of lens paper filter.

After counting the number of the cells using a hematocytometer chamber, the cells were suspended in DMEM medium supplemented with 5% semi-fetal calf serum (Mitsubishi Chemical Co.) and 5% horse serum, and inoculated into 48-well culture plates (Costa) that were pre-coated with polyethyleneimine at a concentration of 5×105 cells per well. The plates were incubated at 37° C. in a 5% $CO_2$ atmosphere. On the third day of culture, the culture medium was replaced by the same medium to which 5-FdU (Sigma) was added.

On the seventh day, toxicological effect of glutamic acid on nerve cells was tested: cells were washed with serum-free DMEM medium twice and exposed to 1 mM glutamic acid (final) for 15 minutes. After washing with serum-free DMEM medium three times, cells were incubated for 24 hours and the amount of released LDH was measured with a LDH kit (Kyokuto Pharmaceutical). The test drug, the compound of this invention (compound in Example 3), was dissolved in DMEM medium containing 1% DMSO at a concentration of 1 mM, and added to each well to make the final concentrations shown in FIG. 1 before exposure to glutamic acid. Thereafter, the cells were cultured in the presence of the test drug, and LDH was measured.

Figure 1:
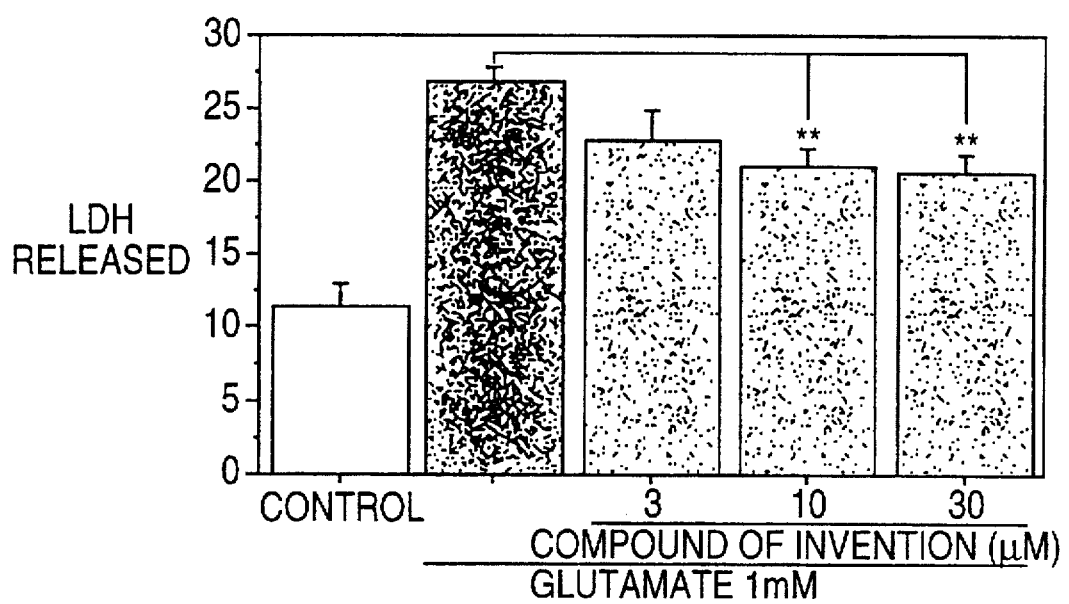
FIG. 1 shows the effect of the compound synthesized by the process shown in Example 3 on the death of nerve cells caused by glutamic acid.

The results are shown in FIG. 1.

FIG. 1 shows that the compound of the invention has a protective effect on neuronal death caused by glutamic acid. This fact suggests that the compound of the invention can be used for the treatment of disorder of the central nervous system as a drug to prevent neuronal death.

Experiment 3

Effect of the compound of the invention on peripheral neuropathy in rats suffering from streptozotocin-induced diabetes.

To rats weighing about 250 g, 50 mg/kg of streptozotocin (STZ) was injected intravenously. After one week, the animals were grouped according to their blood glucose levels. The compound of the invention (compound shown in Example 3) was orally administered daily at a dose of 0.1, 0.3 or 1.0 mg/kg, and sensory nerve conduction velocity (SCV) was measured. Measurement of nerve conduction velocity was performed according to the method by Miyoshi et al. [Fukuokaishi 62 (7), 588–603 (1971)], and the method by Stanley [Experimental Neurology 71, 497–506 (1981)]. Namely, a recording electrode was placed at the end of tail and two stimulating electrodes were set in more proximal regions. The distance between these two electrodes was measured beforehand. On the basis of difference of the latent time of peak hights of H-wave induced by stimulation via two electrodes, and the distance between the two stimulation electrodes, conduction velocity was calculated.

The results are shown in FIG. 2.

FIG. 2 shows that the compound of the invention has a protective effect on decreased peripheral nerve conduction velocity in diabetes. This fact suggests that the compound of the invention can be used for the treatment of neuropathy.

The compounds of the present invention are expected to have preventive and therapeutic effects to dementia, amnesia, diabetic neuropathy or accompanied disorder, because they increase ChAT activity in cholinergic neurons, they have a glutamate antagonistic action, and they improve decreased nerve conduction velocity in STZ rat.

Specially, they are expected to be useful for the prevention and therapy of senile dementia including Alzheimer's disease; cerebrovascular dementia accompanying apoplexy; cerebral hemorrhage, cerebral infarction and the like; and amnesia, aprosexia, allophasis, hypobulia, emotional instability, hallucination, paranoia, behavioral abnormality and the like accompanying head trauma, cerebritis sequela, cerebral palsy, Huntington's disease, Pick's disease, Down's disease, Parkinson's disease and the like. Further, they are expected to be useful for the prevention and therapy of late-onset motor neuron diseases; glaucoma; somnipathy; peripheral neuropathies of motor nerve, sensory nerve, autonomic nerve and the like, based on trauma or inflammation; metabolic neuropathies such as alcoholic neuropathy, neuropathy based on medicines such as carcinostatics, diabetic neuropathy and the like, or spontaneous neuropathies; facial palsy; sciatic palsy; spinal amyotrophy; myodystrophy; myasthenia gravis; multiple sclerosis; amyotrophic lateral sclerosis; acute sporadic encephalomyelitis; Guillain-Barré syndrome; postvaccinal encephalitis; SMON and the like.

What is claimed is:

1. A method for the treatment of senile dementia, which comprises administering to a patient who requires such treatment, an effective amount of a sialic acid derivative represented by the general formula (1):

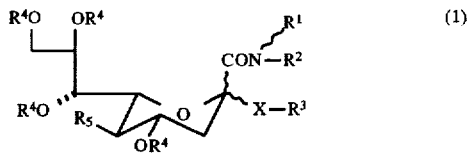

wherein
$R^1$ represents a steroidal compound residue:
$R^2$ represents hydrogen or $C_1-C_4$ alkyl;
$R^3$ represents
  (1) $C_1-C_{15}$ alkyl

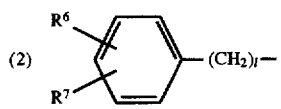

wherein each of $R^6$ and $R^7$ independently represents
  (a) hydrogen,
  (b) halogen,
  (c) $C_1-C_4$ alkyl,
  (d) hydroxyl,
  (e) $R^8O$—,
    wherein $R^8$ represents $C_1-C_4$ alkyl, phenyl or phenyl-$(C_1-C_3)$alkyl,
  (f) nitro,
  (g) amino,
  (h) $C_1-C_4$ alkylamino,
  (i) $C_2-C_8$ dialkylamino, or

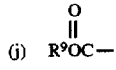

wherein $R^9$ represents hydrogen, $C_1-C_4$ alkyl, phenyl or phenyl-$(C_1-C_3)$ alkyl, and
l represents an integer of 0–6,
  (3) $R^{10}O(CH_2)_m$—
    wherein $R^{10}$ represents
      (a) hydrogen,
      (b) $C_1-C_4$ alkyl,
      (c) phenyl which is unsubstituted or is substituted by at least one member of the group consisting of $C_1-C_4$ alkyl, halogen, hydroxyl, nitro, amino and carboxyl, or
      (d) phenyl-$(C_1-C_3)$alkyl which is unsubstituted or is substituted by at least one member of the group consisting of $C_1-C_4$ alkyl, halogen, hydroxyl, nitro, amino and carboxyl, and
    m is an integer of 2–6, or

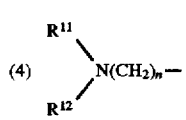

wherein
  $R^{11}$ represents hydrogen or $C_1-C_4$ alkyl,
  $R^{12}$ represents
    (a) hydrogen,
    (b) $C_1-C_4$ alkyl,
    (c) $C_2-C_7$ acyl,
    (d) $C_1-C_4$ alkylsulfonyl,
    (e) phenylsulfonyl which is unsubstituted or is substituted by at least one member selected from the group consisting of $C_1-C_4$ alkyl, halogen, hydroxyl, nitro, amino and carboxyl, or

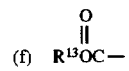

wherein $R^{13}$ represents $C_1-C_4$ alkyl, phenyl, or phenyl-$(C_1-C_3)$alkyl, and
  n is an integer of 2–6,
$R_4$ represents hydrogen or $C_2-C_7$ acyl,
$R_5$ represents
  (1) $R^{14}O$—
    wherein $R^{14}$ is hydrogen or $C_2-C_7$ acyl, or
  (2) $R^{15}NH$—
    wherein $R^{15}$ represents
      (a) $C_2-C_7$ acyl,
      (b) $R^{16}O(CH_2)_pCO$—
        wherein $R^{16}$ represents hydrogen, $C_1-C_6$ alkyl, phenyl or phenyl-$(C_1-C_3)$alkyl, and p represents an integer of 0 to 4,
      (c) $C_7-C_{11}$ aroyl which is unsubstituted or is substituted by at least one member of the group consisting of $C_1-C_4$ alkyl, halogen, hydroxyl, nitro, amino and carboxyl,
      (d) phenyl-$(C_1-C_3)$alkylcarbonyl which is unsubstituted or is substituted by at least one member of the group consisting of $C_1-C_4$ alkyl, halogen, hydroxyl, nitro, amino and carboxyl,
      (e) $C_1-C_4$ alkylsulfonyl, or
      (f) phenylsulfonyl which is unsubstituted or is substituted by at least one member of the group consisting of $C_1-C_4$ alkyl, halogen, hydroxyl, nitro, amino and carboxyl,
X represents O or S,
or a pharmaceutically acceptable salt, hydrate or solvate thereof.

2. A method for the treatment of Alzheimer's disease, which comprises administering to a patient who requires such treatment, an effective amount of a sialic acid derivative represented by the general formula (1):

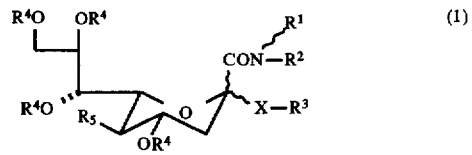

wherein
$R^1$ represents a steroidal compound residue:
$R^2$ represents hydrogen or $C_1-C_4$ alkyl;
$R^3$ represents
  (1) $C_1-C_{15}$ alkyl

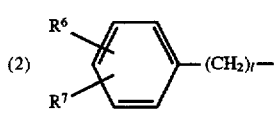

wherein each of $R^6$ and $R^7$ independently represents
  (a) hydrogen, (b) halogen,
(c) $C_1-C_4$ alkyl,
(d) hydroxyl,
(e) $R^8O-$,
wherein $R^8$ represents $C_1-C_4$ alkyl, phenyl or phenyl-$(C_1-C_3)$alkyl,
(f) nitro,
(g) amino,
(h) $C_1-C_4$ alkylamino,
(i) $C_2-C_8$ dialkylamino, or (j) 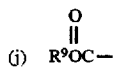

wherein $R^9$ represents hydrogen, $C_1-C_4$ alkyl, phenyl or phenyl-$(C_1-C_3)$ alkyl, and l represents an integer of 0–6, (3) $R^{10}O(CH_2)_m-$
wherein $R^{10}$ represents
(a) hydrogen,
(b) $C_1-C_4$ alkyl,
(c) phenyl which is unsubstituted or is substituted by at least one member of the group consisting of $C_1-C_4$ alkyl, halogen, hydroxyl, nitro, amino and carboxyl, or
(d) phenyl-$(C_1-C_3)$alkyl which is unsubstituted or is substituted by at least one member of the group consisting of $C_1-C_4$ alkyl, halogen, hydroxyl, nitro, amino and carboxyl, and m is an integer of 2–6, or (4) 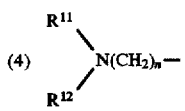

wherein
$R^{11}$ represents hydrogen or $C_1-C_4$ alkyl,
$R^{12}$ represents
(a) hydrogen,
(b) $C_1-C_4$ alkyl,
(c) $C_2-C_7$ acyl,
(d) $C_1-C_4$ alkylsulfonyl,
(e) phenylsulfonyl which is unsubstituted or is substituted by at least one member selected from the group consisting of $C_1-C_4$ alkyl, halogen, hydroxyl, nitro, amino and carboxyl, or (f) 

wherein $R^{13}$ represents $C_1-C_4$ alkyl, phenyl, or phenyl-$(C_1-C_3)$alkyl, and
n is an integer of 2–6,
$R_4$ represents hydrogen or $C_2-C_7$ acyl,
$R_5$ represents
(1) $R^{14}O-$
wherein $R^{14}$ is hydrogen or $C_2-C_7$ acyl, or
(2) $R^{15}NH-$
wherein $R^{15}$ represents
(a) $C_2-C_7$ acyl,
(b) $R^{16}O(CH_2)_pCO-$
wherein $R^{16}$ represents hydrogen, $C_1-C_6$ alkyl, phenyl or phenyl-$(C_1-C_3)$alkyl, and p represents an integer of 0 to 4, (c) $C_7-C_{11}$ aroyl which is unsubstituted or is substituted by at least one member of the group consisting of $C_1-C_4$ alkyl, halogen, hydroxyl, nitro, amino and carboxyl,
(d) phenyl-$(C_1-C_3)$alkylcarbonyl which is unsubstituted or is substituted by at least one member of the group consisting of $C_1-C_4$ alkyl, halogen, hydroxyl, nitro, amino and carboxyl,
(e) $C_1-C_4$ alkylsulfonyl, or
(f) phenylsulfonyl which is unsubstituted or is substituted by at least one member of the group consisting of $C_1-C_4$ alkyl, halogen, hydroxyl, nitro, amino and carboxyl, X represents O or S, or a pharmaceutically acceptable salt, hydrate or solvate thereof.

3. A method for the treatment of stroke, cerebral hemorrhage, or cerebral infarction, which comprises administering to a patient who requires such treatment, an effective amount of a sialic acid derivative represented by the general formula (1):

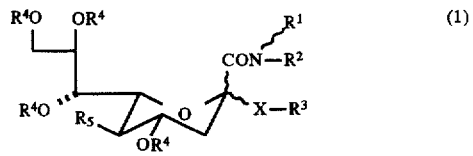

wherein
$R^1$ represents a steroidal compound residue;
$R^2$ represents hydrogen or $C_1-C_4$ alkyl;
$R^3$ represents
(1) $C_1-C_{15}$ alkyl (2) 

wherein each of $R^6$ and $R^7$ independently represents
(a) hydrogen,
(b) halogen,
(c) $C_1-C_4$ alkyl,
(d) hydroxyl,
(e) $R^8O-$,
wherein $R^8$ represents $C_1-C_4$ alkyl, phenyl or phenyl-$(C_1-C_3)$alkyl,
(f) nitro,
(g) amino,
(h) $C_1-C_4$ alkylamino,
(i) $C_2-C_8$ dialkylamino, or (j) 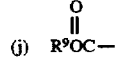

wherein $R^9$ represents hydrogen, $C_1-C_4$ alkyl, phenyl or phenyl-$(C_1-C_3)$ alkyl, and l represents an integer of 0–6, (3) $R^{10}O(CH_2)_m-$
wherein $R^{10}$ represents
(a) hydrogen,
(b) $C_1-C_4$ alkyl,
(c) phenyl which is unsubstituted or is substituted by at least one member of the group consisting of $C_1-C_4$ alkyl, halogen, hydroxyl, nitro, amino and carboxyl, or

161

(d) phenyl-($C_1$-$C_3$)alkyl which is unsubstituted or is substituted by at least one member of the group consisting of $C_1$-$C_4$ alkyl, halogen, hydroxyl, nitro, amino and carboxyl, and m is an integer of 2–6, or (4) $\begin{array}{c}R^{11}\\\diagdown\\ \phantom{R}\diagup\\ R^{12}\end{array}$ N(CH$_2$)$_n$— wherein $R^{11}$ represents hydrogen or $C_1$-$C_4$ alkyl,
$R^{12}$ represents
  (a) hydrogen,
  (b) $C_1$-$C_4$ alkyl,
  (c) $C_2$-$C_7$ acyl,
  (d) $C_1$-$C_4$ alkylsulfonyl,
  (e) phenylsulfonyl which is unsubstituted or is substituted by at least one member selected from the group consisting of $C_1$-$C_4$ alkyl, halogen, hydroxyl, nitro, amino and carboxyl, or (f) $R^{13}$OC—
$\phantom{(f)\ R^{13}}\overset{\displaystyle O}{\overset{\|}{}}$ wherein $R^{13}$ represents $C_1$-$C_4$ alkyl, phenyl, or phenyl-($C_1$-$C_3$)alkyl, and
n is an integer of 2–6, $R_4$ represents hydrogen or $C_2$-$C_7$ acyl,
$R_5$ represents,
  (1) $R^{14}$O—
    wherein $R^{14}$ is hydrogen or $C_2$-$C_7$ acyl, or
  (2) $R^{15}$NH—
    wherein $R^{15}$ represents
    (a) $C_2$-$C_7$ acyl,
    (b) $R^{16}$O(CH$_2$)$_p$CO—
      wherein $R^{16}$ represents hydrogen, $C_1$-$C_6$ alkyl, phenyl or phenyl-($C_1$-$C_3$)alkyl, and p represents an integer of to 4,
    (c) $C_7$-$C_{11}$ aroyl which is unsubstituted or is substituted by at least one member of the group consisting of $C_1$-$C_4$ alkyl, halogen, hydroxyl, nitro, amino and carboxyl,
    (d) phenyl-($C_1$-$C_3$)alkylcarbonyl which is unsubstituted or is substituted by at least one member of the group consisting of $C_1$-$C_4$ alkyl, halogen, hydroxyl, nitro, amino and carboxyl,
    (e) $C_1$-$C_4$ alkylsulfonyl, or
    (f) phenylsulfonyl which is unsubstituted or is substituted by at least one member of the group consisting of $C_1$-$C_4$ alkyl, halogen, hydroxyl, nitro, amino and carboxyl, X represents O or S, or a pharmaceutically acceptable salt, hydrate or solvate thereof.

4. A method for the treatment of amnesia, attention deficit, allophasis, hypobulia, emotional instability, hallucination, paranoia, or behavioral abnormality associated with trauma, cerebritis sequela, cerebral paralysis, Huntington's disease, Pick's disease, Down's disease, or Parkinson's disease, which comprises administering to a patient who requires such treatment, an effective amount of a sialic acid derivative represented by the general formula (I):

162

(1)

wherein $R^1$ represents a steroidal compound residue:
$R^2$ represents hydrogen or $C_1$-$C_4$ alkyl;
$R^3$ represents
  (1) $C_1$-$C_{15}$ alkyl (2) [structure with $R^6$, $R^7$ on phenyl ring]—(CH$_2$)$_l$— wherein each of $R^6$ and $R^7$ independently represents
  (a) hydrogen,
  (b) halogen,
  (c) $C_1$-$C_4$ alkyl,
  (d) hydroxyl,
  (e) $R^8$O—,
    wherein $R^8$ represents $C_1$-$C_4$ alkyl, phenyl or phenyl-($C_1$-$C_3$)alkyl,
  (f) nitro,
  (g) amino,
  (h) $C_1$-$C_4$ alkylamino,
  (i) $C_2$-$C_8$ dialkylamino, or (j) $R^9$OC—
$\phantom{(j)\ R^9}\overset{\displaystyle O}{\overset{\|}{}}$ wherein $R^9$ represents hydrogen, $C_1$-$C_4$ alkyl, phenyl or phenyl-($C_1$-$C_3$) alkyl, and l represents an integer of 0–6, (3) $R^{10}$O(CH$_2$)$_m$—
  wherein $R^{10}$ represents
  (a) hydrogen,
  (b) $C_1$-$C_4$ alkyl,
  (c) phenyl which is unsubstituted or is substituted by at least one member of the group consisting of $C_1$-$C_4$ alkyl, halogen, hydroxyl, nitro, amino and carboxyl, or
  (d) phenyl-($C_1$-$C_3$)alkyl which is unsubstituted or is substituted by at least one member of the group consisting of $C_1$-$C_4$ alkyl, halogen, hydroxyl, nitro, amino and carboxyl, and m is an integer of 2–6, or (4) $\begin{array}{c}R^{11}\\\diagdown\\ \phantom{R}\diagup\\ R^{12}\end{array}$ N(CH$_2$)$_n$— wherein $R^{11}$ represents hydrogen or $C_1$-$C_4$ alkyl,
$R^{12}$ represents
  (a) hydrogen,
  (b) $C_1$-$C_4$ alkyl,
  (C) $C_2$-$C_7$ acyl,
  (d) $C_1$-$C_4$ alkylsulfonyl, (e) phenylsulfonyl which is unsubstituted or is substituted by at least one member selected from the group consisting of $C_1$-$C_4$ alkyl, halogen, hydroxyl, nitro, amino and carboxyl, or (f) 

wherein $R^{13}$ represents $C_1$-$C_4$ alkyl, phenyl, or phenyl-($C_1$-$C_3$)alkyl, and n is an integer of 2–6.

$R_4$ represents hydrogen or $C_2$-$C_7$ acyl, $R_5$ represents (1) $R^{14}O$—
  wherein $R^{14}$ is hydrogen or $C_2$-$C_7$ acyl, or (2) $R^{15}NH$—
  wherein $R^{15}$ represents
  (a) $C_2$-$C_7$ acyl,
  (b) $R^{16}O(CH_2)_pCO$—
    wherein $R^{16}$ represents hydrogen, $C_1$-$C_6$ alkyl, phenyl or phenyl-($C_1$-$C_3$)alkyl, and p represents an integer of 0 to 4,
  (c) $C_7$-$C_{11}$ aroyl which is unsubstituted or is substituted by at least one member of the group consisting of $C_1$-$C_4$ alkyl, halogen, hydroxyl, nitro, amino and carboxyl,
  (d) phenyl-($C_1$-$C_3$)alkylcarbonyl which is unsubstituted or is substituted by at least one member of the group consisting of $C_1$-$C_4$ alkyl, halogen, hydroxyl, nitro, amino and carboxyl,
  (e) $C_1$-$C_4$ alkylsulfonyl, or
  (f) phenylsulfonyl which is unsubstituted or is substituted by at least one member of the group consisting of $C_1$-$C_4$ alkyl, halogen, hydroxyl, nitro, amino and carboxyl, X represents O or S, or a pharmaceutically acceptable salt, hydrate or solvate thereof.

5. A method for the treatment of metabolic neurophathies caused by diabetes, which comprises administering to a patient who requires such treatment, an effective amount of a sialic acid derivative represented by the general formula (1):

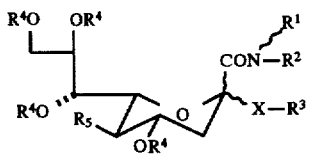

wherein $R^1$ represents a steroidal compound residue:

$R^2$ represents hydrogen or $C_1$-$C_4$ alkyl;

$R^3$ represents (1) $C_1$-$C_{15}$ alkyl (2) 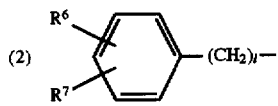

wherein each of $R^6$ and $R^7$ independently represents
(a) hydrogen,
(b) halogen,
(c) $C_1$-$C_4$ alkyl,
(d) hydroxyl,
(e) $R^8O$—,
  wherein $R^8$ represents $C_1$-$C_4$ alkyl, phenyl or phenyl-($C_1$-$C_3$) alkyl,
(f) nitro,
(g) amino,
(h) $C_1$-$C_4$ alkylamino,
(i) $C_2$-$C_8$ dialkylamino, or (j) 

wherein $R^9$ represents hydrogen, $C_1$-$C_4$ alkyl, phenyl or phenyl-($C_1$-$C_3$) alkyl, and l represents an integer of 0–6, (3) $R^{10}O(CH_2)_m$—
  wherein $R^{10}$ represents
  (a) hydrogen,
  (b) $C_1$-$C_4$ alkyl,
  (c) phenyl which is unsubstituted or is substituted by at least one member of the group consisting of $C_1$-$C_4$ alkyl, halogen, hydroxyl, nitro, amino and carboxyl, or
  (d) phenyl-($C_1$-$C_3$)alkyl which is unsubstituted or is substituted by at least one member of the group consisting of $C_1$-$C_4$ alkyl, halogen, hydroxyl, nitro, amino and carboxyl, and m is an integer of 2–6, or (4) 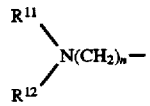

wherein
$R^{11}$ represents hydrogen or $C_1$-$C_4$ alkyl,
$R^{12}$ represents
  (a) hydrogen,
  (b) $C_1$-$C_4$ alkyl,
  (C) $C_2$-$C_7$ acyl,
  (d) $C_1$-$C_4$ alkylsulfonyl, or
  (e) phenylsulfonyl which is unsubstituted or is substituted by at least one member selected from the group consisting of $C_1$-$C_4$ alkyl, halogen, hydroxyl, nitro, amino and carboxyl, or (f) 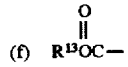

wherein $R^{13}$ represents $C_1$-$C_4$ alkyl, phenyl, or phenyl-($C_1$-$C_3$)alkyl, and n is an integer of 2–6.

$R_4$ represents hydrogen or $C_2$-$C_7$ acyl, $R_5$ represents (1) $R^{14}O$—
  wherein $R^{14}$ is hydrogen or $C_2$-$C_7$ acyl, or (2) $R^{15}NH$—
  wherein $R^{15}$ represents
  (a) $C_2$-$C_7$ acyl,
  (b) $R^{16}O(CH_2)_pCO$— wherein $R^{16}$ represents hydrogen, $C_1$-$C_6$ alkyl, phenyl or phenyl-($C_1$-$C_3$) alkyl, and p represents an integer of 0 to 4,
  (c) $C_7$-$C_{11}$ aroyl which is unsubstituted or is substituted by at least one member of the group consisting of $C_1$-$C_4$ alkyl, halogen, hydroxyl, nitro, amino and carboxyl, (d) phenyl-($C_1$–$C_3$)alkylcarbonyl which is unsubstituted or is substituted by at least one member of the group consisting of $C_1$–$C_4$ alkyl, halogen, hydroxyl, nitro, amino and carboxyl,
(e) $C_1$–$C_4$ alkylsulfonyl, or
(f) phenylsulfonyl which is unsubstituted or is substituted by at least one member of the group consisting of $C_1$–$C_4$ alkyl, halogen, hydroxyl, nitro, amino and carboxyl, X represents O or S, or a pharmaceutically acceptable salt, hydrate or solvate thereof.

* * * * *